(12) United States Patent
Nakatani et al.

(10) Patent No.: US 6,841,519 B1
(45) Date of Patent: Jan. 11, 2005

(54) ISOXAZOLINE DERIVATIVES AND HERBICIDES CONTAINING THE SAME AS THE ACTIVE INGREDIENT

(75) Inventors: Masao Nakatani, Shizuoka (JP);
Kouichirou Kaku, Shizuoka (JP);
Takumi Yoshimura, Shizuoka (JP);
Masatoshi Tamaru, Shizuoka (JP);
Hiroshi Kawasaki, Shizuoka (JP);
Kazunori Kobayashi, Shizuoka (JP);
Takeshige Miyazawa, Shizuoka (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/049,039

(22) PCT Filed: Aug. 9, 2000

(86) PCT No.: PCT/JP00/05325

§ 371 (c)(1),
(2), (4) Date: Feb. 8, 2002

(87) PCT Pub. No.: WO01/12613

PCT Pub. Date: Feb. 22, 2001

(30) Foreign Application Priority Data

Aug. 10, 1999 (JP) .......................................... 11-225878

(51) Int. Cl.[7] ........................ A01N 43/80; C07D 261/04
(52) U.S. Cl. ........................ 504/271; 548/243; 514/378
(58) Field of Search ...................... 504/271; 548/243; 514/378

(56) References Cited

FOREIGN PATENT DOCUMENTS

| JP | 8-225548 | A | 9/1996 |
| JP | 8-225548 | * | 9/1996 |
| WO | 00/50410 | A | 8/2000 |

OTHER PUBLICATIONS

EP Application No. 00 951 908 Office Action dated Feb. 19, 2003. (EP counterpart).
Shimizu, T., et al; "Synthesis of [1]Benzopyrano[4, 3–c] pyrazoles and –[3,4–d]isoxazoles"; *Buletin of the Chemical Society of Japan*; vol. 54, No. 1, pp. 217–222; 1981.
Kazuo Tomita et al.: "Studies on Isoxazoles. IX. Synthesis of 3–Phenoxy–, 3–Phenylthio– and 3–Alkylthioisoxazoles", Chemical & Pharmaceutical Bulletin, vol. 27, No. 10, pp. 215–2423, (1979).

* cited by examiner

*Primary Examiner*—Rita Desai
*Assistant Examiner*—Ebenezer Sackey
(74) *Attorney, Agent, or Firm*—Kubovcik & Kubovcik

(57) ABSTRACT

The isoxazoline derivative of the present invention is represented by the following general formula [I]:

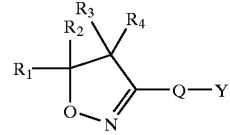

[I]

[wherein Q is a group represented by $-S(O)_n-(CR_5R_6)_m-$ (wherein n is an integer of 0 to 2, m is an integer of 1 to 3, and $R_5$ and $R_6$ are a hydrogen atom, a cyano group, an alkoxycarbonyl group, if an alkyl group or the like); $R_1$ and $R_2$ are a hydrogen atom, all optionally substituted alkyl group, an alkoxycarbonyl group, an optionally substituted phenyl group or the like; $R_3$ and $R_4$ are a hydrogen atom, an optionally substituted alkyl group, a cycloalkyl group or the like; Y is a hydrogen atom, an alkoxycarbonyl group, a carboxyl group, an alkenyl group, an optionally substituted alkyl group or an optionally substituted phenyl group]. The herbicide of the present invention contains the above isoxazoline derivative as the active ingredient.

27 Claims, No Drawings

ISOXAZOLINE DERIVATIVES AND HERBICIDES CONTAINING THE SAME AS THE ACTIVE INGREDIENT

This application is a 371 of PCT/JP00/05325 filed Aug. 9, 2000.

TECHNICAL FIELD

The present invention relates to a novel isoxazoline derivative and a herbicide containing it as the active ingredient.

BACKGROUND ART

The herbicidal activities of isoxazoline derivatives are reported in, for example, JP-A-8-225548, JP-A-9-328477 and JP-A-9-328483. The compounds described in these literatures have a chloromethyl group mainly at the 5-position of the isoxazoline ring, and the isoxazoline derivative of the present invention has been unknown.

Herbicides used for useful crops are desired to be applied to soil or foliage, show a sufficient herbicidal effect at a low amount, and exhibit high selectivity between crop and weeds. The compounds described in the above literatures are not fully satisfactory in these respects.

DISCLOSURE OF THE INVENTION

In view of the above situation, the present inventors made a study on herbicidal effect and selectivity between crop and weeds. As a result, the present inventors found out that a novel isoxazoline derivative is superior in herbicidal effect and selectivity between crop and weeds. The present invention has been completed based on the finding.

The present invention provides:

(1) an isoxazoline derivative represented by the following general formula [I] or a salt thereof:

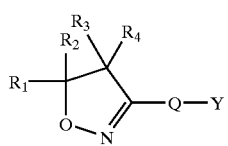

[I]

(wherein Q is a group represented by —S(O)$_n$—(CR$_5$R$_6$)$_m$— (wherein n is an integer of 0 to 2, m is an integer of 1 to 3, and R$_5$ and R$_6$ are each independently a hydrogen atom, a cyano group, an alkoxycarbonyl group or a C$_1$ to C$_6$ alkyl group);

R1 and R$_2$ are a hydrogen atom, a C$_1$ to C$_8$ alkyl group, [which may be substituted with C$_3$ to C$_8$ cycloalkyl group, C$_1$ to C$_6$ alkoxy group, C$_1$ to C$_6$ alkylcarbonyl group, C$_1$ to C$_6$ alkylthio group, C$_1$ to C$_6$ alkylsulfinyl group, C$_1$ to C$_6$ alkylsulfonyl group, C$_1$ to C$_6$ alkylamino group, di(C$_1$ to C$_6$ alkyl)amino group, hydroxyl group, cyano group, C$_1$ to C$_6$ alkoxycarbonyl group, C$_1$ to C$_6$ alkylaminocarbonyl group, di(C$_1$ to C$_6$ alkyl)aminocarbonyl group, (C$_1$ to C$_6$ alkylthio)carbonyl group, carboxyl group, optionally substituted benzyloxy group, optionally substituted phenoxy group, or optionally substituted phenyl group], a C$_3$ to C$_8$ cycloalkyl group, a C$_1$ to C$_6$ alkoxycarbonyl group, a C$_1$ to C$_6$ alkylaminocarbonyl group, a di(C$_1$ to C$_6$ alkyl)aminocarbonyl group, or a (C$_1$ to C$_6$ alkylthiocarbonyl group, carboxyl group or optionally substituted) phenyl group, or, R$_1$ and R$_2$ may form a C$_3$ to C$_7$ spiro ring together with the carbon atom to which they bond;

R$_3$ and R$_4$ are a hydrogen atom, a C$_1$ to C$_8$ alkyl group (which may be substituted with 1 to 3 same or different halogen atoms, C$_3$ to C$_8$ cycloalkyl groups or C$_1$ to C$_6$ alkoxy groups) or a C$_3$ to C$_8$ cycloalkyl group, and R$_3$ and R$_4$ may form a C$_3$ to C$_7$ spiro ring together with the carbon atom to which they bond, or, R$_1$, R$_2$, R$_3$ and R$_4$ may form a 5- to 8-membered ring together with the carbon atoms to which they bond;

Y is a hydrogen atom, a C$_1$ to C$_6$ alkoxycarbonyl group, a carboxyl group, a C$_2$ to C$_6$ alkenyl group, a C$_1$ to C$_{10}$ alkyl group [which may be substituted with 1 to 3 same or different halogen atoms, C$_1$ to C$_6$ alkoxy groups, C$_2$ to C$_6$ alkenyloxy groups, C$_2$ to C$_6$ alkynyloxy groups, optionally substituted benzyloxy gorups, C$_1$ to C$_6$ alkoxycarbonyl groups, carboxyl groups, hydroxyl groups or formyl groups], or a phenyl group substituted with 1 to 5 same or different R$_7$s;

each R$_7$ is a hydrogen atom, a C$_1$ to C$_6$ alkyl group [which may be substituted with 1 to 3 same or different halogen atoms, C$_1$ to C$_6$ alkoxy groups, hydroxyl groups, C$_1$ to C$_6$ alkylthio groups, C$_1$ to C$_6$ alkylsulfinyl groups, C$_1$ to C$_6$ alkylsulfonyl groups, C$_1$ to C$_6$ alkylamino groups, di(C$_1$ to C$_6$)alkylamino groups, cyano groups or optionally substituted phenoxy groups], a C$_1$ to C$_6$ alkoxy group (which may be substituted with 1 to 3 same or different halogen atoms, C$_1$ to C$_6$ alkoxy groups, C$_2$ to C$_6$ alkenyl groups, C$_2$ to C$_6$ alkynyl groups, C$_1$ to C$_6$ alkoxycarbonyl groups, C$_1$ to C$_6$ alkylcarbonyl groups or C$_3$ to C$_8$ cycloalkyl groups), a C$_2$ to C$_6$ alkenyl group, a C$_3$ to C$_8$ cycloalkyloxy group, a C$_1$ to C$_6$ alkylthio group (which may be substituted with 1 to 3 same or different halogen atoms or C$_1$ to C$_6$ alkoxy groups), a C$_1$ to C$_6$ alkylsulfinyl group (which may be substituted with 1 to 3 same or different halogen atoms or C$_1$ to C$_6$ alkoxy groups), a C$_1$ to C$_6$ alkylsulfonyl group (which may be substituted with 1 to 3 same or different halogen atoms or C$_1$ to C$_6$ alkoxy groups), an optionally substituted benzyloxy group, an amino group [which may be substituted with C$_1$ to C$_6$ alkyl group, C$_1$ to C$_6$ alkylsulfonyl group, C$_1$ to C$_6$ alkylcarbonyl (C$_1$ to C$_6$ alkyl) group or C$_1$ to C$_6$ alkylsulfonyl (C$_1$ to C$_6$ alkyl) group], a di(C$_1$ to C$_6$ alkyl) amino group, a halogen atom, a cyano group, a nitro group, a C$_1$ to C$_6$ alkoxycarbonyl group, a C$_3$ to C$_8$ cycloalkyloxycarbonyl group, a carboxyl group, a C$_2$ to C$_6$ alkenyloxycarbonyl group, a C$_2$ to C$_6$ alkynyloxycarbonyl group, an optionally substituted benzyloxycarbonyl group, an optionally substituted phenoxycarbonyl group or a C$_1$ to C$_6$ alkylcarbonyloxy group).

(2) a herbicide containing, as the active ingredient, an isoxazoline derivative or its salt set forth in the above (1).

BEST MODE FOR CARRYING OUT THE INVENTION

The definitions of the terms used in the present specification are given below.

"Halogen atom" refers to a fluorine atom, a chlorine atom, a bromine atom or an iodine atom.

"Alkyl group" refers to a C$_1$ to C$_{10}$ straight or branched chain alkyl group unless other wise specified; and there can be mentioned, for example, methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, 3,3-dimethylbutyl group, heptyl group and octyl group.

"Cycloalkyl group" refers to a $C_3$ to $C_8$ cycloalkyl group; and there can be mentioned, for example, cyclopropyl group, cyclobutyl group, cyclopentyl group and cyclohexyl group.

"Alkoxy group" refers to an (alkyl)-O- group wherein the alkyl moiety has the above definition; and there can be mentioned, for example, methoxy group and ethoxy group.

"Alkylthio group", "alkylsulfinyl group" and "alkylsulfonyl group" refer, respectively, to an (alkyl)-S— group, an (alkyl)-SO— group and an (alkyl)-$SO_2$— group, in each of which the alkyl moiety has the above definition; and there can be mentioned, for example, methylthio group, ethylthio group, methylsulfinyl group, methylsulfonyl group and ethylsulfonyl group.

"Alkenyl group" refers to a $C_2$ to $C_6$ straight or branched chain alkenyl group; and there can be mentioned, for example, ethenyl group, 1-propenyl group, 2-propenyl group, isopropenyl group, 1-butenyl group, 2-butenyl group, 3-butenyl group and 2-pentenyl group.

"Alkynyl group" refers to a $C_2$ to $C_6$ straight or branched chain alkynyl group; and there can be mentioned, for example, ethinyl group, 2-propynyl group, 2-butinyl group and 3-butinyl group.

"Alkenyloxy group" and "alkynyloxy group" refer, respectively, to an (alkenyl)-O— group and an (alkynyl)-O— group, in each of which the alkenyl or alkynyl moiety has the above definition; and there can be mentioned, for example, 2-propenyloxy group and 2-propynyloxy group.

"Alkylamino group" and "dialkylamino group" refer, respectively, to an (alkyl)-NH— group and an $(alkyl)_2$—N— group, in each of which the alkyl moiety has the above definition; and there can be mentioned, for example, methylamino group, ethylamino group and dimethylamino group.

"Alkylcarbonyl group", "(alkylthio)carbonyl group", "alkoxycarbonyl group", "alkylaminocarbonyl group" and "dialkylaminocarbonyl group" refer, respectively, to an (alkyl)-CO— group, an (alkylthio)-CO— group, an (alkoxy)-CO— group, an (alkylamino)-CO— group and a (dialkylamino)-CO— group, in each of which the alkyl, alkylthio, alkoxy, alkylamino or dialkylamino moiety has the above definition; and there can be mentioned, for example, acetyl group, methylthiocarbonyl group, ethoxycarbonyl group, methoxycarbonyl group, methylaminocarbonyl group and dimethylaminocarbonyl group.

"Alkylaminocarbonylamino group", "dialkylaminocarbonylamino group" and "alkoxycarbonylamino group" refer, respectively, to an (alkylaminocarbonyl)-NH— group, a (dialkylaminocarbonyl)-NH— group and an (alkxoycarbonyl)-NH— group, in each of which the alkylaminocarbonyl, dialkylaminocarbonyl or alkoxycarbonyl moiety has the above definition; and there can be mentioned, for example, methylaminocarbonylamino group, dimethylaminocarbonylamino group and methoxycarbonylamino group.

"Optionally substituted phenyl group" includes phenyl groups each having, on the phenyl ring, 1 to 5 substituents such as halogen atom(s), $C_1$ to $C_6$ alkyl group(s), $C_1$ to $C_6$ alkoxy group(s) and the like.

"Optionally substituted phenoxy group" includes phenoxy groups each having, on the phenyl ring, 1 to 5 substituents such as halogen atom (s), $C_1$ to $C_6$ alkyl group(s), $C_1$ to $C_6$ alkoxy group(s) and the like.

"Optionally substituted benzyloxy group" includes benzyloxy groups each having, on the phenyl ring and at the benzylic position, 1 to 7 substituents such as halogen atom (s), $C_1$ to $C_6$ alkyl group(s), $C_1$ to $C_6$ alkoxy group(s) and the like.

"Optionally substituted phenoxycarbonyl group" includes phenoxycarbonyl groups each having, on the phenyl ring, 1 to 5 substituents such as halogen atom(s), $C_1$ to $C_6$ alkyl group(s), $C_1$ to $C_6$ alkoxy group(s) and the like.

"Salt" refers to a salt between the carboxyl group, sulfonyl group, hydroxyl group, amino group or other group present in the compound of the general formula [1] and a metal, an organic base, an organic acid or an inorganic acid. As the metal, there can be mentioned alkali metals such as sodium, potassium and the like, and alkaline earth metals such as magnesium, calcium and the like. As the organic base, there can be mentioned triethylamine, diisopropylamine, etc. As the organic acid, there can be mentioned acetic acid, oxalic acid, maleic acid, p-toluenesulfonic acid, etc. As the inorganic acid, there can be mentioned hydrochloric acid, sulfuric acid, nitric acid, etc.

Preferable examples of the compound of the general formula [I] are those compounds wherein $R_1$ and $R_2$ are a $C_1$ to $C_3$ alkyl group or a $C_1$ to $C_3$ alkoxyalkyl group, $R_3$ and $R_4$ are a hydrogen atom or a $C_1$ to $C_3$ alkyl group, Q is a group represented by —$S(O)_n$-$(CR_5R_6)_m$-, $R_5$ and $R_6$ are a hydrogen atom or a $C_1$ to $C_3$ alkyl group, n is 2, m is 1, and Y is an optionally substituted phenyl group or a $C_2$ to $C_{10}$ alkyl group.

Next, representative examples of the present compound of the general formula [I] are shown in Tables 1 to 24. However, the present compound is not restricted to these. Incidentally, the No. of each compound is used also in the later description.

The following abbreviations used in the following tables indicate the following groups.

| Me: | methyl group | Et: | ethyl group |
|---|---|---|---|
| Pr: | n-propyl group | Pr-i: | isopropyl group |
| Pr-c: | cyclopropyl group | Bu: | n-butyl group |
| Bu-i: | isobutyl group | Bu-s: | sec-butyl group |
| Bu-t: | tert-butyl group | Bu-c: | cyclobutyl group |
| Pen: | n-pentyl group | Hex: | n-hexyl group |
| Pen-c: | cyclopentyl group | Hex-c: | cyclohexyl group |
| Ph: | phenyl group | Bn: | benzyl group |

TABLE 1

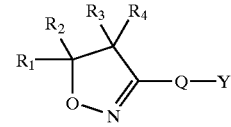

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-1 | Me | Me | H | H | $SO_2CH_2$ | Ph | 108.5–110 |
| 1-2 | Me | Me | H | H | $SO_2CH_2$ | Ph(2-Cl) | 71–72 |
| 1-3 | Me | Me | H | H | $SO_2CH_2$ | Ph(3-Cl) | 91.5–92 |
| 1-4 | Me | Me | H | H | $SO_2CH_2$ | Ph(4-Cl) | 138–138.5 |
| 1-5 | Me | Me | H | H | $SO_2CH_2$ | Ph(2-Me) | 96–97 |
| 1-6 | Me | Me | H | H | $SO_2CH_2$ | Ph(3-Me) | 78–79 |
| 1-7 | Me | Me | H | H | $SO_2CH_2$ | Ph(4-Me) | 97–98 |
| 1-8 | Me | Me | H | H | $SO_2CH_2$ | Ph(2-Et) | 1.5390 |
| 1-9 | Me | Me | H | H | $SO_2CH_2$ | Ph(3-Et) | |
| 1-10 | Me | Me | H | H | $SO_2CH_2$ | Ph(4-Et) | |
| 1-11 | Me | Me | H | H | $SO_2CH_2$ | Ph(2-Pr) | |
| 1-12 | Me | Me | H | H | $SO_2CH_2$ | Ph(3-Pr) | |
| 1-13 | Me | Me | H | H | $SO_2CH_2$ | Ph(4-Pr) | |
| 1-14 | Me | Me | H | H | $SO_2CH_2$ | Ph(2-Pr-i) | |
| 1-15 | Me | Me | H | H | $SO_2CH_2$ | Ph(3-Pr-i) | |
| 1-16 | Me | Me | H | H | $SO_2CH_2$ | Ph(4-Pr-i) | |

TABLE 1-continued $$\begin{array}{c}\phantom{R_1}R_2\phantom{R_3}R_3\phantom{R_4}R_4\\ R_1\diagdown\phantom{xxxx}\diagup\\ \diagup\phantom{xx}\diagdown\phantom{x}Q\text{—}Y\\ O\phantom{xxxx}N\end{array}$$

| Compound No. | R₁ | R₂ | R₃ | R₄ | Q | Y | Melting point (° C.) or refractive index ($n_D^{20}$) |
|---|---|---|---|---|---|---|---|
| 1-17 | Me | Me | H | H | SO₂CH₂ | Ph(2-Bu) | |
| 1-18 | Me | Me | H | H | SO₂CH₂ | Ph(3-Bu) | |
| 1-19 | Me | Me | H | H | SO₂CH₂ | Ph(4-Bu) | |
| 1-20 | Me | Me | H | H | SO₂CH₂ | Ph(2-Bu-i) | |

TABLE 2

| Compound No. | R₁ | R₂ | R₃ | R₄ | Q | Y | Melting point (° C.) or refractive index ($n_D^{20}$) |
|---|---|---|---|---|---|---|---|
| 1-21 | Me | Me | H | H | SO₂CH₂ | Ph(3-Bu-i) | |
| 1-22 | Me | Me | H | H | SO₂CH₂ | Ph(4-Bu-i) | |
| 1-23 | Me | Me | H | H | SO₂CH₂ | Ph(2-Bu-s) | |
| 1-24 | Me | Me | H | H | SO₂CH₂ | Ph(3-Bu-s) | |
| 1-25 | Me | Me | H | H | SO₂CH₂ | Ph(4-Bu-s) | |
| 1-26 | Me | Me | H | H | SO₂CH₂ | Ph(2-Bu-t) | |
| 1-27 | Me | Me | H | H | SO₂CH₂ | Ph(3-Bu-t) | |
| 1-28 | Me | Me | H | H | SO₂CH₂ | Ph(4-Bu-t) | |
| 1-29 | Me | Me | H | H | SO₂CH₂ | Ph(2-Hex) | |
| 1-30 | Me | Me | H | H | SO₂CH₂ | Ph(3-Hex) | |
| 1-31 | Me | Me | H | H | SO₂CH₂ | Ph(4-Hex) | |
| 1-32 | Me | Me | H | H | SO₂CH₂ | Ph(2-F) | 102–103 |
| 1-33 | Me | Me | H | H | SO₂CH₂ | Ph(3-F) | 105–105.5 |
| 1-34 | Me | Me | H | H | SO₂CH₂ | Ph(4-F) | 138–138.5 |
| 1-35 | Me | Me | H | H | SO₂CH₂ | Ph(2-Br) | 77–78 |
| 1-36 | Me | Me | H | H | SO₂CH₂ | Ph(3-Br) | |
| 1-37 | Me | Me | H | H | SO₂CH₂ | Ph(4-Br) | |
| 1-38 | Me | Me | H | H | SCH₂ | Ph(2,6-F₂) | 77–80 |
| 1-39 | Me | Me | H | H | SO₂CH₂ | Ph(2,6-F₂) | 110–111 |
| 1-40 | Me | Me | H | H | SO₂CH₂ | Ph(2-OMe) | 94–95 |
| 1-41 | Me | Me | H | H | SO₂CH₂ | Ph(3-OMe) | 89–90 |
| 1-42 | Me | Me | H | H | SO₂CH₂ | Ph(4-OMe) | 122–124 |
| 1-43 | Me | Me | H | H | SO₂CH₂ | Ph(2-OEt) | 76–79 |
| 1-44 | Me | Me | H | H | SO₂CH₂ | Ph(3-OEt) | |
| 1-45 | Me | Me | H | H | SO₂CH₂ | Ph(4-OEt) | |

TABLE 3

| Compound No. | R₁ | R₂ | R₃ | R₄ | Q | Y | Melting point (° C.) or refractive index ($n_D^{20}$) |
|---|---|---|---|---|---|---|---|
| 1-46 | Me | Me | H | H | SO₂CH₂ | Ph(2-OPr) | 67–68 |
| 1-47 | Me | Me | H | H | SO₂CH₂ | Ph(3-OPr) | |
| 1-48 | Me | Me | H | H | SO₂CH₂ | Ph(4-OPr) | |
| 1-49 | Me | Me | H | H | SO₂CH₂ | Ph(2-OPr-i) | 73–74 |
| 1-50 | Me | Me | H | H | SO₂CH₂ | Ph(3-OPr-i) | |
| 1-51 | Me | Me | H | H | SO₂CH₂ | Ph(4-OPr-i) | |
| 1-52 | Me | Me | H | H | SO₂CH₂ | Ph(2-OHex) | |
| 1-53 | Me | Me | H | H | SO₂CH₂ | Ph(3-OHex) | |
| 1-54 | Me | Me | H | H | SO₂CH₂ | Ph(4-OHex) | |
| 1-55 | Me | Me | H | H | SO₂CH₂ | Ph(2-OCHF₂) | 80–81 |
| 1-56 | Me | Me | H | H | SO₂CH₂ | Ph(3-OCHF₂) | 51–53 |
| 1-57 | Me | Me | H | H | SO₂CH₂ | Ph(4-OCHF₂) | |
| 1-58 | Me | Me | H | H | SO₂CH₂ | Ph(2-OCF₃) | 1.492 |
| 1-59 | Me | Me | H | H | SO₂CH₂ | Ph(3-OCF₃) | 82–84 |
| 1-60 | Me | Me | H | H | SO₂CH₂ | Ph(4-OCF₃) | |
| 1-61 | Me | Me | H | H | SO₂CH₂ | Ph(2-OCH₂CH₂OMe) | |
| 1-62 | Me | Me | H | H | SO₂CH₂ | Ph(3-OCH₂CH₂OMe) | |
| 1-63 | Me | Me | H | H | SO₂CH₂ | Ph(4-OCH₂CH₂OMe) | |
| 1-64 | Me | Me | H | H | SO₂CH₂ | Ph(2-SMe) | |
| 1-65 | Me | Me | H | H | SO₂CH₂ | Ph(3-SMe) | |
| 1-66 | Me | Me | H | H | SO₂CH₂ | Ph(4-SMe) | |
| 1-67 | Me | Me | H | H | SO₂CH₂ | Ph(2-SEt) | |
| 1-68 | Me | Me | H | H | SO₂CH₂ | Ph(3-SEt) | |
| 1-69 | Me | Me | H | H | SO₂CH₂ | Ph(4-SEt) | |
| 1-70 | Me | Me | H | H | SO₂CH₂ | Ph(2-SPr) | |

TABLE 4

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-71 | Me | Me | H | H | $SO_2CH_2$ | Ph(3-SPr) | |
| 1-72 | Me | Me | H | H | $SO_2CH_2$ | Ph(4-SPr) | |
| 1-73 | Me | Me | H | H | $SO_2CH_2$ | Ph(2-SBu) | |
| 1-74 | Me | Me | H | H | $SO_2CH_2$ | Ph(3-SBu) | |
| 1-75 | Me | Me | H | H | $SO_2CH_2$ | Ph(4-SBu) | |
| 1-76 | Me | Me | H | H | $SO_2CH_2$ | Ph(2-SHex) | |
| 1-77 | Me | Me | H | H | $SO_2CH_2$ | Ph(3-SHex) | |
| 1-78 | Me | Me | H | H | $SO_2CH_2$ | Ph(4-SHex) | |
| 1-79 | Me | Me | H | H | $SO_2CH_2$ | Ph(2-SCHF_2) | |
| 1-80 | Me | Me | H | H | $SO_2CH_2$ | Ph(3-SCHF_2) | |
| 1-81 | Me | Me | H | H | $SO_2CH_2$ | Ph(4-SCHF_2) | |
| 1-82 | Me | Me | H | H | $SO_2CH_2$ | Ph(2-SCH_2CH_2OMe) | |
| 1-83 | Me | Me | H | H | $SO_2CH_2$ | Ph(3-SCH_2CH_2OMe) | |
| 1-84 | Me | Me | H | H | $SO_2CH_2$ | Ph(4-SCH_2CH_2OMe) | |
| 1-85 | Me | Me | H | H | $SO_2CH_2$ | Ph(2-SOMe) | |
| 1-86 | Me | Me | H | H | $SO_2CH_2$ | Ph(3-SOMe) | |
| 1-87 | Me | Me | H | H | $SO_2CH_2$ | Ph(4-SOMe) | |
| 1-88 | Me | Me | H | H | $SO_2CH_2$ | Ph(2-SOEt) | |
| 1-89 | Me | Me | H | H | $SO_2CH_2$ | Ph(3-SOEt) | |
| 1-90 | Me | Me | H | H | $SO_2CH_2$ | Ph(4-SOEt) | |
| 1-91 | Me | Me | H | H | $SO_2CH_2$ | Ph(2-SOPr) | |
| 1-92 | Me | Me | H | H | $SO_2CH_2$ | Ph(3-SOPr) | |
| 1-93 | Me | Me | H | H | $SO_2CH_2$ | Ph(4-SOPr) | |
| 1-94 | Me | Me | H | H | $SO_2CH_2$ | Ph(2-SOBu) | |
| 1-95 | Me | Me | H | H | $SO_2CH_2$ | Ph(3-SOBu) | |

TABLE 5

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-96 | Me | Me | H | H | $SO_2CH_2$ | Ph(4-SOBu) | |
| 1-97 | Me | Me | H | H | $SO_2CH_2$ | Ph(2-SOHex) | |
| 1-98 | Me | Me | H | H | $SO_2CH_2$ | Ph(3-SOHex) | |
| 1-99 | Me | Me | H | H | $SO_2CH_2$ | Ph(4-SOHex) | |
| 1-100 | Me | Me | H | H | $SO_2CH_2$ | Ph(2-SOCH_2CF_3) | |
| 1-101 | Me | Me | H | H | $SO_2CH_2$ | Ph(3-SOCH_2CF_3) | |
| 1-102 | Me | Me | H | H | $SO_2CH_2$ | Ph(4-SOCH_2CF_3) | |
| 1-103 | Me | Me | H | H | $SO_2CH_2$ | Ph(2-SOCH_2CH_2OMe) | |
| 1-104 | Me | Me | H | H | $SO_2CH_2$ | Ph(3-SOCH_2CH_2OMe) | |
| 1-105 | Me | Me | H | H | $SO_2CH_2$ | Ph(4-SOCH_2CH_2OMe) | |
| 1-106 | Me | Me | H | H | $SO_2CH_2$ | Ph(2-SO_2Me) | 97–98 |
| 1-107 | Me | Me | H | H | $SO_2CH_2$ | Ph(3-SO_2Me) | |
| 1-108 | Me | Me | H | H | $SO_2CH_2$ | Ph(4-SO_2Me) | |
| 1-109 | Me | Me | H | H | $SO_2CH_2$ | Ph(2-SO_2Et) | |
| 1-110 | Me | Me | H | H | $SO_2CH_2$ | Ph(3-SO_2Et) | |
| 1-111 | Me | Me | H | H | $SO_2CH_2$ | Ph(4-SO_2Et) | |
| 1-112 | Me | Me | H | H | $SO_2CH_2$ | Ph(2-SO_2Pr) | |
| 1-113 | Me | Me | H | H | $SO_2CH_2$ | Ph(3-SO_2Pr) | |
| 1-114 | Me | Me | H | H | $SO_2CH_2$ | Ph(4-SO_2Pr) | |
| 1-115 | Me | Me | H | H | $SO_2CH_2$ | Ph(2-SO_2Bu) | |
| 1-116 | Me | Me | H | H | $SO_2CH_2$ | Ph(3-SO_2Bu) | |
| 1-117 | Me | Me | H | H | $SO_2CH_2$ | Ph(4-SO_2Bu) | |
| 1-118 | Me | Me | H | H | $SO_2CH_2$ | Ph(2-SO_2Hex) | |
| 1-119 | Me | Me | H | H | $SO_2CH_2$ | Ph(3-SO_2Hex) | |
| 1-120 | Me | Me | H | H | $SO_2CH_2$ | Ph(4-SO_2Hex) | |

TABLE 6

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-121 | Me | Me | H | H | $SO_2CH_2$ | Ph(2-SO_2CH_2CH_2OMe) | |
| 1-122 | Me | Me | H | H | $SO_2CH_2$ | Ph(3-SO_2CH_2CH_2OMe) | |
| 1-123 | Me | Me | H | H | $SO_2CH_2$ | Ph(4-SO_2CH_2CH_2OMe) | |

TABLE 6-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-124 | Me | Me | H | H | $SO_2CH_2$ | $Ph(2-SO_2CH_2CF_3)$ | |
| 1-125 | Me | Me | H | H | $SO_2CH_2$ | $Ph(3-SO_2CH_2CF_3)$ | |
| 1-126 | Me | Me | H | H | $SO_2CH_2$ | $Ph(4-SO_2CH_2CF_3)$ | |
| 1-127 | Me | Me | H | H | $SO_2CH_2$ | $Ph(2-CH_2OPh)$ | |
| 1-128 | Me | Me | H | H | $SO_2CH_2$ | $Ph(3-CH_2OPh)$ | |
| 1-129 | Me | Me | H | H | $SO_2CH_2$ | $Ph(4-CH_2OPh)$ | |
| 1-130 | Me | Me | H | H | $SO_2CH_2$ | $Ph(2-CH_2OPh(2-Cl))$ | |
| 1-131 | Me | Me | H | H | $SO_2CH_2$ | $Ph(3-CH_2OPh(3-Me))$ | |
| 1-132 | Me | Me | H | H | $SO_2CH_2$ | $Ph(4-CH_2OPh(4-OMe))$ | |
| 1-133 | Me | Me | H | H | $SO_2CH_2$ | $Ph(2-NHMe)$ | |
| 1-134 | Me | Me | H | H | $SO_2CH_2$ | $Ph(3-NHMe)$ | |
| 1-135 | Me | Me | H | H | $SO_2CH_2$ | $Ph(4-NHMe)$ | |
| 1-136 | Me | Me | H | H | $SO_2CH_2$ | $Ph(2-N(Me)_2)$ | |
| 1-137 | Me | Me | H | H | $SO_2CH_2$ | $Ph(3-N(Me)_2)$ | |
| 1-138 | Me | Me | H | H | $SO_2CH_2$ | $Ph(4-N(Me)_2)$ | |
| 1-139 | Me | Me | H | H | $SO_2CH_2$ | $Ph(2-CN)$ | 120–122 |
| 1-140 | Me | Me | H | H | $SO_2CH_2$ | $Ph(3-CN)$ | |
| 1-141 | Me | Me | H | H | $SO_2CH_2$ | $Ph(4-CN)$ | |
| 1-142 | Me | Me | H | H | $SO_2CH_2$ | $Ph(2-NO_2)$ | 102–103 |
| 1-143 | Me | Me | H | H | $SO_2CH_2$ | $Ph(3-NO_2)$ | |
| 1-144 | Me | Me | H | H | $SO_2CH_2$ | $Ph(4-NO_2)$ | |
| 1-145 | Me | Me | H | H | $SO_2CH_2$ | $Ph(2-CO_2Me)$ | 97–98 |

TABLE 7

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-146 | Me | Me | H | H | $SO_2CH_2$ | $Ph(3-CO_2Me)$ | |
| 1-147 | Me | Me | H | H | $SO_2CH_2$ | $Ph(4-CO_2Me)$ | |
| 1-148 | Me | Me | H | H | $SO_2CH_2$ | $Ph(2-NHSO_2Me)$ | |
| 1-149 | Me | Me | H | H | $SO_2CH_2$ | $Ph(3-NHSO_2Me)$ | |
| 1-150 | Me | Me | H | H | $SO_2CH_2$ | $Ph(4-NHSO_2Me)$ | |
| 1-151 | Me | Me | H | H | $SO_2CH_2$ | $Ph(2-NHCH_2COMe)$ | |
| 1-152 | Me | Me | H | H | $SO_2CH_2$ | $Ph(3-NHCH_2COMe)$ | |
| 1-153 | Me | Me | H | H | $SO_2CH_2$ | $Ph(4-NHCH_2COMe)$ | |
| 1-154 | Me | Me | H | H | $SO_2CH_2$ | $Ph(2-NHCH_2SO_2Me)$ | |
| 1-155 | Me | Me | H | H | $SO_2CH_2$ | $Ph(3-NHCH_2SO_2Me)$ | |
| 1-156 | Me | Me | H | H | $SO_2CH_2$ | $Ph(4-NHCH_2SO_2Me)$ | |
| 1-157 | Me | Me | H | H | $SO_2CH_2$ | $Ph(2-CF_3)$ | 1.5009 |
| 1-158 | Me | Me | H | H | $SO_2CH_2$ | $Ph(3-CF_3)$ | 103–104 |
| 1-159 | Me | Me | H | H | $SO_2CH_2$ | $Ph(4-CF_3)$ | |
| 1-160 | Me | Me | H | H | $SO_2CH_2$ | $Ph(2-CH_2OMe)$ | 1.5352 |
| 1-161 | Me | Me | H | H | $SO_2CH_2$ | $Ph(3-CH_2OMe)$ | |
| 1-162 | Me | Me | H | H | $SO_2CH_2$ | $Ph(4-CH_2OMe)$ | |
| 1-163 | Me | Me | H | H | $SO_2CH_2$ | $Ph(2-CH_2OH)$ | |
| 1-164 | Me | Me | H | H | $SO_2CH_2$ | $Ph(3-CH_2OH)$ | |
| 1-165 | Me | Me | H | H | $SO_2CH_2$ | $Ph(4-CH_2OH)$ | |
| 1-166 | Me | Me | H | H | $SO_2CH_2$ | $Ph(2-CH_2SMe)$ | |
| 1-167 | Me | Me | H | H | $SO_2CH_2$ | $Ph(3-CH_2SMe)$ | |
| 1-168 | Me | Me | H | H | $SO_2CH_2$ | $Ph(4-CH_2SMe)$ | |
| 1-169 | Me | Me | H | H | $SO_2CH_2$ | $Ph(2-CH_2SOMe)$ | |
| 1-170 | Me | Me | H | H | $SO_2CH_2$ | $Ph(3-CH_2SOMe)$ | |

TABLE 8

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-171 | Me | Me | H | H | $SO_2CH_2$ | $Ph(4-CH_2SOMe)$ | |
| 1-172 | Me | Me | H | H | $SO_2CH_2$ | $Ph(2-CH_2SO_2Me)$ | |
| 1-173 | Me | Me | H | H | $SO_2CH_2$ | $Ph(3-CH_2SO_2Me)$ | |
| 1-174 | Me | Me | H | H | $SO_2CH_2$ | $Ph(4-CH_2SO_2Me)$ | |
| 1-175 | Me | Me | H | H | $SO_2CH_2$ | $Ph(2-CH_2NHMe)$ | |
| 1-176 | Me | Me | H | H | $SO_2CH_2$ | $Ph(3-CH_2NHMe)$ | |

TABLE 8-continued

| Compound No. | R₁ | R₂ | R₃ | R₄ | Q | Y | Melting point (° C.) or refractive index ($n_D^{20}$) |
|---|---|---|---|---|---|---|---|
| 1-177 | Me | Me | H | H | SO₂CH₂ | Ph(4-CH₂NHMe) | |
| 1-178 | Me | Me | H | H | SO₂CH₂ | Ph(2-CH₂N(Me)₂) | |
| 1-179 | Me | Me | H | H | SO₂CH₂ | Ph(3-CH₂N(Me)₂) | |
| 1-180 | Me | Me | H | H | SO₂CH₂ | Ph(4-CH₂N(Me)₂) | |
| 1-181 | Me | Me | H | H | SO₂CH₂ | Ph(2-CH₂CN) | |
| 1-182 | Me | Me | H | H | SO₂CH₂ | Ph(3-CH₂CN) | |
| 1-183 | Me | Me | H | H | SO₂CH₂ | Ph(4-CH₂CN) | |
| 1-184 | Me | Me | H | H | SO₂CH₂ | Ph(2-F, 3-Cl) | 128–130 |
| 1-185 | Me | Me | H | H | SO₂CH₂ | Ph(2,6-Me₂) | 110–112 |
| 1-186 | Me | Me | H | H | SO₂CH₂ | Ph(2-OEt, 3-Me) | 1.5231 |
| 1-187 | Me | Me | H | H | SO₂CH₂ | Ph(2-F, 3-Me) | 91–92 |
| 1-188 | Me | Et | H | H | SO₂CH₂ | Ph | 38–39 |
| 1-189 | Me | Et | H | H | SO₂CH₂ | Ph(2-F) | 65–67 |
| 1-190 | Me | Et | H | H | SO₂CH₂ | Ph(3-F) | 58–59 |
| 1-191 | Me | Et | H | H | SO₂CH₂ | Ph(4-F) | 75–78 |
| 1-192 | Me | Et | H | H | SO₂CH₂ | Ph(2-Cl) | 1.5472 |
| 1-193 | Me | Et | H | H | SO₂CH₂ | Ph(3-Cl) | 67–68 |
| 1-194 | Me | Et | H | H | SO₂CH₂ | Ph(4-Cl) | 93–94 |
| 1-195 | Me | Et | H | H | SO₂CH₂ | Ph(2-Br) | 1.5289 |

TABLE 9

| Compound No. | R₁ | R₂ | R₃ | R₄ | Q | Y | Melting point (° C.) or refractive index ($n_D^{20}$) |
|---|---|---|---|---|---|---|---|
| 1-196 | Me | Et | H | H | SO₂CH₂ | Ph(3-Br) | |
| 1-197 | Me | Et | H | H | SO₂CH₂ | Ph(4-Br) | |
| 1-198 | Me | Et | H | H | SCH₂ | Ph(2,6-F₂) | 51–52 |
| 1-199 | Me | Et | H | H | SOCH₂ | Ph(2,6-F₂) | <30 |
| 1-200 | Me | Et | H | H | SO₂CH₂ | Ph(2,6-F₂) | 64–65 |
| 1-201 | Me | Et | H | H | SO₂CH₂ | Ph(2-Me) | 1.5371 |
| 1-202 | Me | Et | H | H | SO₂CH₂ | Ph(3-Me) | 41–42 |
| 1-203 | Me | Et | H | H | SO₂CH₂ | Ph(4-Me) | 43–44 |
| 1-204 | Me | Et | H | H | SO₂CH₂ | Ph(2-Et) | |
| 1-205 | Me | Et | H | H | SO₂CH₂ | Ph(3-Et) | |
| 1-206 | Me | EL | H | H | SO₂CH₂ | Ph(4-Et) | |
| 1-207 | Me | Et | H | H | SO₂CH₂ | Ph(2-Pr) | |
| 1-208 | Me | Et | H | H | SO₂CH₂ | Ph(3-Pr) | |
| 1-209 | Me | Et | H | H | SO₂CH₂ | Ph(4-Pr) | |
| 1-210 | Me | Et | H | H | SO₂CH₂ | Ph(2-Pr-i) | |
| 1-211 | Me | Et | H | H | SO₂CH₂ | Ph(3-Pr-i) | |
| 1-212 | Me | Et | H | H | SO₂CH₂ | Ph(4-Pr-i) | |
| 1-213 | Me | Et | H | H | SO₂CH₂ | Ph(2-Bu) | |
| 1-214 | Me | Et | H | H | SO₂CH₂ | Ph(3-Bu) | |
| 1-215 | Me | Et | H | H | SO₂CH₂ | Ph(4-Bu) | |
| 1-216 | Me | Et | H | H | SO₂CH₂ | Ph(2-Bu-i) | |
| 1-217 | Me | Et | H | H | SO₂CH₂ | Ph(3-Bu-i) | |
| 1-218 | Me | Et | H | H | SO₂CH₂ | Ph(4-Bu-i) | |
| 1-219 | Me | Et | H | H | SO₂CH₂ | Ph(2-Bu-s) | |
| 1-220 | Me | Et | H | H | SO₂CH₂ | Ph(3-Bu-s) | |

TABLE 10

| Compound No. | R₁ | R₂ | R₃ | R₄ | Q | Y | Melting point (° C.) or refractive index ($n_D^{20}$) |
|---|---|---|---|---|---|---|---|
| 1-221 | Me | Et | H | H | SO₂CH₂ | Ph(4-Bu-s) | |
| 1-222 | Me | Et | H | H | SO₂CH₂ | Ph(2-Bu-t) | |
| 1-223 | Me | Et | H | H | SO₂CH₂ | Ph(3-Bu-t) | |
| 1-224 | Me | Et | H | H | SO₂CH₂ | Ph(4-Bu-t) | |
| 1-225 | Me | Et | H | H | SO₂CH₂ | Ph(2-Hex) | |
| 1-226 | Me | Et | H | H | SO₂CH₂ | Ph(3-Hex) | |
| 1-227 | Me | Et | H | H | SO₂CH₂ | Ph(4-Hex) | |
| 1-228 | Me | Et | H | H | SO₂CH₂ | Ph(2-OMe) | Unable to measure |
| 1-229 | Me | Et | H | H | SO₂CH₂ | Ph(3-OMe) | 1.5219 |
| 1-230 | Me | Et | H | H | SO₂CH₂ | Ph(4-OMe) | 72–74 |
| 1-231 | Me | Et | H | H | SO₂CH₂ | Ph(2-OEt) | |
| 1-232 | Me | Et | H | H | SO₂CH₂ | Ph(3-OEt) | |
| 1-233 | Me | Et | H | H | SO₂CH₂ | Ph(4-OEt) | |
| 1-234 | Me | Et | H | H | SO₂CH₂ | Ph(2-OPr) | |
| 1-235 | Me | Et | H | H | SO₂CH₂ | Ph(3-OPr) | |
| 1-236 | Me | Et | H | H | SO₂CH₂ | Ph(4-OPr) | |
| 1-237 | Me | Et | H | H | SO₂CH₂ | Ph(2-OPr-i) | |
| 1-238 | Me | Et | H | H | SO₂CH₂ | Ph(3-OPr-i) | |
| 1-239 | Me | Et | H | H | SO₂CH₂ | Ph(4-OPr-i) | |
| 1-240 | Me | Et | H | H | SO₂CH₂ | Ph(2-OHex) | |
| 1-241 | Me | Et | H | H | SO₂CH₂ | Ph(3-OHex) | |
| 1-242 | Me | Et | H | H | SO₂CH₂ | Ph(4-OHex) | |
| 1-243 | Me | Et | H | H | SO₂CH₂ | Ph(2-OCHF₂) | |
| 1-244 | Me | Et | H | H | SO₂CH₂ | Ph(3-OCHF₂) | |
| 1-245 | Me | Et | H | H | SO₂CH₂ | Ph(4-OCHF₂) | |

TABLE 11

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-246 | Me | Et | H | H | $SO_2CH_2$ | Ph(2-$OCF_3$) | |
| 1-247 | Me | Et | H | H | $SO_2CH_2$ | Ph(3-$OCF_3$) | |
| 1-248 | Me | Et | H | H | $SO_2CH_2$ | Ph(4-$OCF_3$) | |
| 1-249 | Me | Et | H | H | $SO_2CH_2$ | Ph(2-$OCH_2CH_2OMe$) | |
| 1-250 | Me | Et | H | H | $SO_2CH_2$ | Ph(3-$OCH_2CH_2OMe$) | |
| 1-251 | Me | Et | H | H | $SO_2CH_2$ | Ph(4-$OCH_2CH_2OMe$) | |
| 1-252 | Me | Et | H | H | $SO_2CH_2$ | Ph(2-SMe) | |
| 1-253 | Me | Et | H | H | $SO_2CH_2$ | Ph(3-SMe) | |
| 1-254 | Me | Et | H | H | $SO_2CH_2$ | Ph(4-SMe) | |
| 1-255 | Me | Et | H | H | $SO_2CH_2$ | Ph(2-SEt) | |
| 1-256 | Me | Et | H | H | $SO_2CH_2$ | Ph(3-SEt) | |
| 1-257 | Me | Et | H | H | $SO_2CH_2$ | Ph(4-SEt) | |
| 1-258 | Me | Et | H | H | $SO_2CH_2$ | Ph(2-SPr) | |
| 1-259 | Me | Et | H | H | $SO_2CH_2$ | Ph(3-SPr) | |
| 1-260 | Me | Et | H | H | $SO_2CH_2$ | Ph(4-SPr) | |
| 1-261 | Me | Et | H | H | $SO_2CH_2$ | Ph(2-SBu) | |
| 1-262 | Me | Et | H | H | $SO_2CH_2$ | Ph(3-SBu) | |
| 1-263 | Me | Et | H | H | $SO_2CH_2$ | Ph(4-SBu) | |
| 1-264 | Me | Et | H | H | $SO_2CH_2$ | Ph(2-SHex) | |
| 1-265 | Me | Et | H | H | $SO_2CH_2$ | Ph(3-SHex) | |
| 1-266 | Me | Et | H | H | $SO_2CH_2$ | Ph(4-SHex) | |
| 1-267 | Me | Et | H | H | $SO_2CH_2$ | Ph(2-$SCHF_2$) | |
| 1-268 | Me | Et | H | H | $SO_2CH_2$ | Ph(3-$SCHF_2$) | |
| 1-269 | Me | Et | H | H | $SO_2CH_2$ | Ph(4-$SCHF_2$) | |
| 1-270 | Me | Et | H | H | $SO_2CH_2$ | Ph(2-$SCH_2CH_2OMe$) | |

TABLE 12

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-271 | Me | Et | H | H | $SO_2CH_2$ | Ph(3-$SCH_2CH_2OMe$) | |
| 1-272 | Me | Et | H | H | $SO_2CH_2$ | Ph(4-$SCH_2CH_2OMe$) | |
| 1-273 | Me | Et | H | H | $SO_2CH_2$ | Ph(2-SOMe) | |
| 1-274 | Me | Et | H | H | $SO_2CH_2$ | Ph(3-SOMe) | |
| 1-275 | Me | Et | H | H | $SO_2CH_2$ | Ph(4-SOMe) | |
| 1-276 | Me | Et | H | H | $SO_2CH_2$ | Ph(2-SOEt) | |
| 1-277 | Me | Et | H | H | $SO_2CH_2$ | Ph(3-SOEt) | |
| 1-278 | Me | Et | H | H | $SO_2CH_2$ | Ph(4-SOEt) | |
| 1-279 | Me | Et | H | H | $SO_2CH_2$ | Ph(2-SOPr) | |
| 1-280 | Me | Et | H | H | $SO_2CH_2$ | Ph(3-SOPr) | |
| 1-281 | Me | Et | H | H | $SO_2CH_2$ | Ph(4-SOPr) | |
| 1-282 | Me | Et | H | H | $SO_2CH_2$ | Ph(2-SOBu) | |
| 1-283 | Me | Et | H | H | $SO_2CH_2$ | Ph(3-SOBu) | |
| 1-284 | Me | Et | H | H | $SO_2CH_2$ | Ph(4-SOBu) | |
| 1-285 | Me | Et | H | H | $SO_2CH_2$ | Ph(2-SOHex) | |
| 1-286 | Me | Et | H | H | $SO_2CH_2$ | Ph(3-SOHex) | |
| 1-287 | Me | Et | H | H | $SO_2CH_2$ | Ph(4-SOHex) | |
| 1-288 | Me | Et | H | H | $SO_2CH_2$ | Ph(2-$SOCH_2CF_3$) | |
| 1-289 | Me | Et | H | H | $SO_2CH_2$ | Ph(3-$SOCH_2CF_3$) | |
| 1-290 | Me | Et | H | H | $SO_2CH_2$ | Ph(4-$SOCH_2CF_3$) | |
| 1-291 | Me | Et | H | H | $SO_2CH_2$ | Ph(2-$SOCH_2CH_2OMe$) | |
| 1-292 | Me | Et | H | H | $SO_2CH_2$ | Ph(3-$SOCH_2CH_2OMe$) | |
| 1-293 | Me | Et | H | H | $SO_2CH_2$ | Ph(4-$SOCH_2CH_2OMe$) | |
| 1-294 | Me | Et | H | H | $SO_2CH_2$ | Ph(2-$SO_2Me$) | |
| 1-295 | Me | Et | H | H | $SO_2CH_2$ | Ph(3-$SO_2Me$) | |

TABLE 13

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-296 | Me | Et | H | H | $SO_2CH_2$ | Ph(4-$SO_2Me$) | |
| 1-297 | Me | Et | H | H | $SO_2CH_2$ | Ph(2-$SO_2Et$) | |
| 1-298 | Me | Et | H | H | $SO_2CH_2$ | Ph(3-$SO_2Et$) | |

TABLE 13-continued

| Compound No. | R₁ | R₂ | R₃ | R₄ | Q | Y | Melting point (° C.) or refractive index ($n_D^{20}$) |
|---|---|---|---|---|---|---|---|
| 1-299 | Me | Et | H | H | SO₂CH₂ | Ph(4-SO₂Et) | |
| 1-300 | Me | Et | H | H | SO₂CH₂ | Ph(2-SO₂Pr) | |
| 1-301 | Me | Et | H | H | SO₂CH₂ | Ph(3-SO₂Pr) | |
| 1-302 | Me | Et | H | H | SO₂CH₂ | Ph(4-SO₂Pr) | |
| 1-303 | Me | Et | H | H | SO₂CH₂ | Ph(2-SO₂Bu) | |
| 1-304 | Me | Et | H | H | SO₂CH₂ | Ph(3-SO₂Bu) | |
| 1-305 | Me | Et | H | H | SO₂CH₂ | Ph(4-SO₂Bu) | |
| 1-306 | Me | Et | H | H | SO₂CH₂ | Ph(2-SO₂Hex) | |
| 1-307 | Me | Et | H | H | SO₂CH₂ | Ph(3-SO₂Hex) | |
| 1-308 | Me | Et | H | H | SO₂CH₂ | Ph(4-SO₂Hex) | |
| 1-309 | Me | Et | H | H | SO₂CH₂ | Ph(2-SO₂CH₂CF₃) | |
| 1-310 | Me | Et | H | H | SO₂CH₂ | Ph(3-SO₂CH₂CF₃) | |
| 1-311 | Me | Et | H | H | SO₂CH₂ | Ph(4-SO₂CH₂CF₃) | |
| 1-312 | Me | Et | H | H | SO₂CH₂ | Ph(2-SO₂CH₂CH₂OMe) | |
| 1-313 | Me | Et | H | H | SO₂CH₂ | Ph(3-SO₂CH₂CH₂OMe) | |
| 1-314 | Me | Et | H | H | SO₂CH₂ | Ph(4-SO₂CH₂CH₂OMe) | |
| 1-315 | Me | Et | H | H | SO₂CH₂ | Ph(2-OBn) | |
| 1-316 | Me | Et | H | H | SO₂CH₂ | Ph(3-OBn) | |
| 1-317 | Me | Et | H | H | SO₂CH₂ | Ph(4-OBn) | |
| 1-318 | Me | Et | H | H | SO₂CH₂ | Ph(2-OBn(2-Cl)) | |
| 1-319 | Me | Et | H | H | SO₂CH₂ | Ph(2-OBn(3-Me)) | |
| 1-320 | Me | Et | H | H | SO₂CH₂ | Ph(2-OBn(4-OMe)) | |

TABLE 14

| Compound No. | R₁ | R₂ | R₃ | R₄ | Q | Y | Melting point (° C.) or refractive index ($n_D^{20}$) |
|---|---|---|---|---|---|---|---|
| 1-321 | Me | Et | H | H | SO₂CH₂ | Ph(2-NHMe) | |
| 1-322 | Me | Et | H | H | SO₂CH₂ | Ph(3-NHMe) | |
| 1-323 | Me | Et | H | H | SO₂CH₂ | Ph(4-NHMe) | |
| 1-324 | Me | Et | H | H | SO₂CH₂ | Ph(2-N(Me)₂) | |
| 1-325 | Me | Et | H | H | SO₂CH₂ | Ph(3-N(Me)₂) | |
| 1-326 | Me | Et | H | H | SO₂CH₂ | Ph(4-N(Me)₂) | |
| 1-327 | Me | Et | H | H | SO₂CH₂ | Ph(2-CN) | |
| 1-328 | Me | Et | H | H | SO₂CH₂ | Ph(3-CN) | 83–84 |
| 1-329 | Me | Et | H | H | SO₂CH₂ | Ph(4-CN) | 87–89 |
| 1-330 | Me | Et | H | H | SO₂CH₂ | Ph(2-NO₂) | |
| 1-331 | Me | Et | H | H | SO₂CH₂ | Ph(3-NO₂) | 115–117 |
| 1-332 | Me | Et | H | H | SO₂CH₂ | Ph(4-NO₂) | |
| 1-333 | Me | Et | H | H | SO₂CH₂ | Ph(2-CO₂Me) | |
| 1-334 | Me | Et | H | H | SO₂CH₂ | Ph(3-CO₂Me) | 1.5152 |
| 1-335 | Me | Et | H | H | SO₂CH₂ | Ph(4-CO₂Me) | |
| 1-336 | Me | Et | H | H | SO₂CH₂ | Ph(2-CF₃) | 1.5021 |
| 1-337 | Me | Et | H | H | SO₂CH₂ | Ph(3-CF₃) | |
| 1-338 | Me | Et | H | H | SO₂CH₂ | Ph(4-CF₃) | |
| 1-339 | Me | Et | H | H | SO₂CH₂ | Ph(2-CH₂OMe) | |
| 1-340 | Me | Et | H | H | SO₂CH₂ | Ph(3-CH₂OMe) | |
| 1-341 | Me | Et | H | H | SO₂CH₂ | Ph(4-CH₂OMe) | |
| 1-342 | Me | Et | H | H | SO₂CH₂ | Ph(2-CH₂OH) | |
| 1-343 | Me | Et | H | H | SO₂CH₂ | Ph(3-CH₂OH) | |
| 1-344 | Me | Et | H | H | SO₂CH₂ | Ph(4-CH₂OH) | |
| 1-345 | Me | Et | H | H | SO₂CH₂ | Ph(2-CH₂SMe) | |

TABLE 15

| Compound No. | R₁ | R₂ | R₃ | R₄ | Q | Y | Melting point (° C.) or refractive index ($n_D^{20}$) |
|---|---|---|---|---|---|---|---|
| 1-346 | Me | Et | H | H | SO₂CH₂ | Ph(3-CH₂SMe) | |
| 1-347 | Me | Et | H | H | SO₂CH₂ | Ph(4-CH₂SMe) | |
| 1-348 | Me | Et | H | H | SO₂CH₂ | Ph(2-CH₂SOMe) | |
| 1-349 | Me | Et | H | H | SO₂CH₂ | Ph(3-CH₂SOMe) | |
| 1-350 | Me | Et | H | H | SO₂CH₂ | Ph(4-CH₂SOMe) | |
| 1-351 | Me | Et | H | H | SO₂CH₂ | Ph(2-CH₂SO₂Me) | |
| 1-352 | Me | Et | H | H | SO₂CH₂ | Ph(3-CH₂SO₂Me) | |
| 1-353 | Me | Et | H | H | SO₂CH₂ | Ph(4-CH₂SO₂Me) | |
| 1-354 | Me | Et | H | H | SO₂CH₂ | Ph(2-CH₂NHMe) | |

TABLE 15-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-355 | Me | Et | H | H | $SO_2CH_2$ | $Ph(3-CH_2NHMe)$ | |
| 1-356 | Me | Et | H | H | $SO_2CH_2$ | $Ph(4-CH_2NHMe)$ | |
| 1-357 | Me | Et | H | H | $SO_2CH_2$ | $Ph(2-CH_2N(Me)_2)$ | |
| 1-358 | Me | Et | H | H | $SO_2CH_2$ | $Ph(3-CH_2N(Me)_2)$ | |
| 1-359 | Me | Et | H | H | $SO_2CH_2$ | $Ph(4-CH_2N(Me)_2)$ | |
| 1-360 | Me | Et | H | H | $SO_2CH_2$ | $Ph(2-CH_2CN)$ | |
| 1-361 | Me | Et | H | H | $SO_2CH_2$ | $Ph(3-CH_2CN)$ | |
| 1-362 | Me | Et | H | H | $SO_2CH_2$ | $Ph(4-CH_2CN)$ | |
| 1-363 | Et | Et | H | H | $SOCH_2$ | $Ph(2,6-F_2)$ | 63–65 |
| 1-364 | Et | Et | H | H | $SO_2CH_2$ | $Ph(2,6-F_2)$ | 87–89 |
| 1-365 | Me | Pr | H | H | SOCH2 | $Ph(2,6-F_2)$ | 44–47 |
| 1-366 | Me | Pr | H | H | $SO_2CH_2$ | $Ph(2,6-F_2)$ | 61–63 |
| 1-367 | Me | Pr-i | H | H | $SOCH_2$ | $Ph(2,6-F_2)$ | 1.5319 |
| 1-368 | Me | Pr-i | H | H | $SO_2CH_2$ | $Ph(2,6-F_2)$ | 62–63 |
| 1-369 | Me | Me | H | H | $SO_2CH(Me)$ | Ph | |
| 1-370 | Me | Me | H | H | $SO_2CH(Me)$ | $Ph(2,6-F_2)$ | |

TABLE 16

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-371 | Me | Et | H | H | $SO_2CH(Me)$ | Ph | |
| 1-372 | Me | Et | H | H | $SO_2CH(Me)$ | $Ph(2,6-F_2)$ | |
| 1-373 | Me | Me | H | H | $SO_2C(Me)_2$ | Ph | |
| 1-374 | Me | Me | H | H | $SO_2C(Me)_2$ | $Ph(2,6-F_2)$ | |
| 1-375 | Me | Et | H | H | $SO_2C(Me)_2$ | Ph | |
| 1-376 | Me | Et | H | H | $SO_2C(Me)_2$ | $Ph(2,6-F_2)$ | |
| 1-377 | Me | Bn | H | H | $SO_2CH_2$ | $Ph(2,6-F_2)$ | 111–113 |
| 1-378 | Me | Pr-c | H | H | $SO_2CH_2$ | $Ph(2,6-F_2)$ | 49–51 |
| 1-379 | Me | $CH_2Pr$-c | H | H | $SO_2CH_2$ | $Ph(2,6-F_2)$ | |
| 1-380 | —$(CH_2)_2$— | | H | H | $SO_2CH_2$ | $Ph(2,6-F_2)$ | 137–138 |
| 1-381 | —$(CH_2)_3$— | | H | H | $SCH_2$ | $Ph(2,6-F_2)$ | 93–95 |
| 1-382 | —$(CH_2)_3$— | | H | H | $SO_2CH_2$ | $Ph(2,6-F_2)$ | 115–115.5 |
| 1-383 | —$(CH_2)_4$— | | H | H | $SO_2CH_2$ | $Ph(2,6-F_2)$ | 113–114 |
| 1-384 | —$(CH_2)_5$— | | H | H | $SO_2CH_2$ | $Ph(2,6-F_2)$ | 118–120 |
| 1-385 | H | —$(CH_2)_3$— | | H | $SO_2CH_2$ | $Ph(2,6-F_2)$ | |
| 1-386 | H | —$(CH_2)_4$— | | H | $SCH_2$ | $Ph(2,6-F_2)$ | 1.5529 |
| 1-387 | H | —$(CH_2)_4$— | | H | $SO_2CH_2$ | $Ph(2,6-F_2)$ | 1.5342 |
| 1-388 | H | —$(CH_2)_5$— | | H | $SO_2CH_2$ | $Ph(2,6-F_2)$ | 138–139 |
| 1-389 | Me | $CH_2CO_2Me$ | H | H | $SO_2CH_2$ | $Ph(2,6-F_2)$ | |
| 1-390 | Me | $CH_2CO_2Et$ | H | H | $SO_2CH_2$ | $Ph(2,6-F_2)$ | 1.516 |
| 1-391 | Me | $CH_2CN$ | H | H | $SO_2CH_2$ | $Ph(2,6-F_2)$ | |
| 1-392 | Me | $CH_2OH$ | H | H | $SCH_2$ | $Ph(2,6-F_2)$ | 73–75 |
| 1-393 | Me | $CH_2OH$ | H | H | $SOCH_2$ | $Ph(2,6-F_2)$ | 80–84 |
| 1-394 | Me | $CH_2OH$ | H | H | $SO_2CH_2$ | $Ph(2,6-F_2)$ | 129–131 |
| 1-395 | Me | $CH_2OMe$ | H | H | $SCH_2$ | $Ph(2,6-F_2)$ | 1.5279 |

TABLE 17

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-396 | Me | $CH_2OMe$ | H | H | $SOCH_2$ | $Ph(2,6-F_2)$ | 1.5293 |
| 1-397 | Me | $CH_2OMe$ | H | H | $SO_2CH_2$ | $Ph(2,6-F_2)$ | 105–106 |
| 1-398 | Me | $CH_2OPh(2,6-Cl_2)$ | H | H | $SCH_2$ | $Ph(2,6-F_2)$ | 1.5715 |
| 1-399 | Me | $CH_2OPh(2,6-Cl_2)$ | H | H | $SOCH_2$ | $Ph(2,6-F_2)$ | 1.5674 |
| 1-400 | Me | $CH_2OPh(2,6-Cl_2)$ | H | H | $SO_2CH_2$ | $Ph(2,6-F_2)$ | 1.5461 |
| 1-401 | Me | $CH_2OBn(2,6-F_2)$ | H | H | $SO_2CH_2$ | $Ph(2,6-F_2)$ | 1.5257 |
| 1-402 | Me | $CH_2SMe$ | H | H | $SO_2CH_2$ | $Ph(2,6-F_2)$ | |
| 1-403 | Me | $CH_2SEt$ | H | H | $SO_2CH_2$ | $Ph(2,6-F_2)$ | |
| 1-404 | Me | $CH_2SPr$ | H | H | $SO_2CH_2$ | $Ph(2,6-F_2)$ | |
| 1-405 | Me | $CH_2SPr$-i | H | H | $SO_2CH_2$ | $Ph(2,6-F_2)$ | |
| 1-406 | Me | $CH_2SOMe$ | H | H | $SO_2CH_2$ | $Ph(2,6-F_2)$ | |
| 1-407 | Me | $CH_2SOEt$ | H | H | $SO_2CH_2$ | $Ph(2,6-F_2)$ | |

TABLE 17-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-408 | Me | CH$_2$SOPr | H | H | SO$_2$CH$_2$ | Ph(2,6-F$_2$) | |
| 1-409 | Me | CH$_2$SOPr-i | H | H | SO$_2$CH$_2$ | Ph(2,6-F$_2$) | |
| 1-410 | Me | CH$_2$NHMe | H | H | SO$_2$CH$_2$ | Ph(2,6-F$_2$) | |
| 1-411 | Me | CH$_2$NHEt | H | H | SCH$_2$ | Ph(2,6-F$_2$) | 1.5268 |
| 1-412 | Me | CH$_2$NHEt | H | H | SO$_2$CH$_2$ | Ph(2,6-F$_2$) | |
| 1-413 | Me | CH$_2$NHPr | H | H | SO$_2$CH$_2$ | Ph(2,6-F$_2$) | |
| 1-414 | Me | CH$_2$NHPr-i | H | H | SO$_2$CH$_2$ | Ph(2,6-F$_2$) | |
| 1-415 | Me | CH$_2$N(Me)$_2$ | H | H | SO$_2$CH$_2$ | Ph(2,6-F$_2$) | |
| 1-416 | Me | Bn(2-Me) | H | H | SO$_2$CH$_2$ | Ph(2,6-F$_2$) | |
| 1-417 | Me | Bn(3-OMe) | H | H | SO$_2$CH$_2$ | Ph(2,6-F$_2$) | |
| 1-418 | Me | Bn(4-Cl) | H | H | SO$_2$CH$_2$ | Ph(2,6-F$_2$) | |
| 1-419 | Me | CO$_2$H | H | H | SCH$_2$ | Ph(2,6-F$_2$) | 107–108 |
| 1-420 | Me | CO$_2$Me | H | H | SCH$_2$ | Ph(2,6-F$_2$) | 75–76 |

TABLE 18

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-421 | Me | CO$_2$Me | H | H | SOCH$_2$ | Ph(2,6-F$_2$) | 56–59 |
| 1-422 | Me | CO$_2$Me | H | H | SO$_2$CH$_2$ | Ph(2,6-F$_2$) | 115–116 |
| 1-423 | Me | CO$_2$Et | H | H | SO$_2$CH$_2$ | Ph(2,6-F$_2$) | |
| 1-424 | Me | CO$_2$Pr | H | H | SO$_2$CH$_2$ | Ph(2,6-F$_2$) | |
| 1-425 | Me | CO$_2$Pr-i | H | H | SO$_2$CH$_2$ | Ph(2,6-F$_2$) | |
| 1-426 | Me | COSMe | H | H | SO$_2$CH$_2$ | Ph(2,6-F$_2$) | |
| 1-427 | Me | COSEt | H | H | SO$_2$CH$_2$ | Ph(2,6-F$_2$) | |
| 1-428 | Me | COSPr | H | H | SO$_2$CH$_2$ | Ph(2,6-F$_2$) | |
| 1-429 | Me | COSPr-i | H | H | SO$_2$CH$_2$ | Ph(2,6-F$_2$) | |
| 1-430 | Me | CONHMe | H | H | SO$_2$CH$_2$ | Ph(2,6-F$_2$) | |
| 1-431 | Me | CONHEt | H | H | SO$_2$CH$_2$ | Ph(2,6-F$_2$) | |
| 1-432 | Me | CONHPr | H | H | SO$_2$CH$_2$ | Ph(2,6-F$_2$) | |
| 1-433 | Me | CONHPr-i | H | H | SO$_2$CH$_2$ | Ph(2,6-F$_2$) | |
| 1-434 | Me | CON(Me)$_2$ | H | H | SCH$_2$ | Ph(2,6-F$_2$) | 1.5423 |
| 1-435 | Me | CON(Me)$_2$ | H | H | SOCH$_2$ | Ph(2,6-F$_2$) | 1.5409 |
| 1-436 | Me | CON(Me)$_2$ | H | H | SO$_2$CH$_2$ | Ph(2,6-F$_2$) | 1.5236 |
| 1-437 | Me | CON(Et)(Me) | H | H | SO$_2$CH$_2$ | Ph(2,6-F$_2$) | |
| 1-438 | Me | CON(Et)$_2$ | H | H | SO$_2$CH$_2$ | Ph(2,6-F$_2$) | |
| 1-439 | Me | CON(Pr)$_2$ | H | H | SO$_2$CH$_2$ | Ph(2,6-F$_2$) | |
| 1-440 | Me | Ph | H | H | SO$_2$CH$_2$ | Ph(2,6-F$_2$) | |
| 1-441 | Me | Ph(2-Me) | H | H | SO$_2$CH$_2$ | Ph(2,6-F$_2$) | |
| 1-442 | Me | Ph(3-OMe) | H | H | SO$_2$CH$_2$ | Ph(2,6-F$_2$) | |
| 1-443 | Me | Ph(4-Cl) | H | H | SOCH$_2$ | Ph(2,6-F$_2$) | 1.5788 |
| 1-444 | Me | Ph(4-Cl) | H | H | SO$_2$CH$_2$ | Ph(2,6-F$_2$) | 100–101 |
| 1-445 | Me | Me | Me | Me | SOCH$_2$ | Ph(2,6-F$_2$) | |

TABLE 19

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-446 | Me | Me | Me | Me | SO$_2$CH$_2$ | Ph(2,6-F$_2$) | |
| 1-447 | H | H | Me | Me | SOCH$_2$ | Ph(2,6-F$_2$) | |
| 1-448 | H | H | Me | Me | SO$_2$CH$_2$ | Ph(2,6-F$_2$) | |
| 1-449 | Me | Me | H | H | SO$_2$CH(CO$_2$Me) | Ph(2,6-F$_2$) | |
| 1-450 | Me | Me | H | H | SO$_2$CH(CN) | Ph(2,6-F$_2$) | |
| 1-451 | Me | Me | H | H | SO$_2$(CH$_2$)$_2$ | Ph(2,6-F$_2$) | |
| 1-452 | Me | Me | H | H | SO$_2$(CH$_2$)$_3$ | Ph(2,6-F$_2$) | |
| 1-453 | Me | Et | H | H | SO$_2$CH(CO$_2$Me) | Ph(2,6-F$_2$) | |
| 1-454 | Me | Et | H | H | SO$_2$CH(CN) | Ph(2,6-F$_2$) | |
| 1-455 | Me | Et | H | H | SO$_2$(CH$_2$)$_2$ | Ph(2,6-F$_2$) | |
| 1-456 | Me | Et | H | H | SO$_2$(CH$_2$)$_2$ | Ph | 63–64 |
| 1-457 | Me | Et | H | H | SO$_2$(CH$_2$)$_3$ | Ph | 1.5161 |
| 1-458 | Me | Et | H | H | SO$_2$(CH$_2$)$_3$ | Ph(2,6-F$_2$) | |
| 1-459 | Me | Me | H | H | SO$_2$CH$_2$ | CF$_3$ | |
| 1-460 | Me | Me | H | H | SO$_2$CH$_2$ | CH$_2$CF$_3$ | |

TABLE 19-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-461 | Me | Me | H | H | $SO_2CH_2$ | $CH_2OH$ | |
| 1-462 | Me | Me | H | H | $SCH_2$ | $CH_2OH$ | |
| 1-463 | Me | Me | H | H | $SO_2CH_2$ | $CH_2OMe$ | |
| 1-464 | Me | Me | H | H | $SO_2CH_2$ | $CH_2OHex$ | |
| 1-465 | Me | Me | H | H | $SO_2CH_2$ | $CH_2OCH_2CH=CH_2$ | |
| 1-466 | Me | Me | H | H | $SO_2CH_2$ | $CH_2OBn$ | |
| 1-467 | Me | Et | H | H | $SCH_2$ | $CO_2H$ | 1.5088 |
| 1-468 | Me | Et | H | H | $SO_2CH_2$ | $CH_2CO_2Me$ | 1.4852 |
| 1-469 | Me | Et | H | H | $SCH_2$ | $CH_2CO_2Me$ | 1.4919 |
| 1-470 | Me | Me | H | H | $SO_2CH_2$ | $CH_2CO_2Me$ | |

TABLE 20

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-471 | Me | Me | H | H | $SO_2CH_2$ | $CH_2CO_2H$ | |
| 1-472 | Me | Me | H | H | $SO_2CH_2$ | $CH_2OH$ | |
| 1-473 | Me | Me | H | H | $SO_2CH_2$ | $CH_2CHO$ | |
| 1-474 | Me | Me | H | H | $SO_2CH_2$ | $CH=CH_2$ | |
| 1-475 | Me | Et | H | H | $SO_2CH_2$ | $CF_3$ | |
| 1-476 | Me | Et | H | H | $SO_2CH_2$ | $CH_2CF_3$ | |
| 1-477 | Me | Et | H | H | $SCH_2$ | $CH_2OH$ | 1.5088 |
| 1-478 | Me | Et | H | H | $SO_2CH_2$ | $CH_2OH$ | |
| 1-479 | Me | Et | H | H | $SO_2CH_2$ | $CH_2OMe$ | |
| 1-480 | Me | Et | H | H | $SO_2CH_2$ | $CH_2OHex$ | |
| 1-481 | Me | Et | H | H | $SO_2CH_2$ | $CH_2OCH_2CH=CH_2$ | |
| 1-482 | Me | Et | H | H | $SO_2CH_2$ | $CH_2OBn$ | |
| 1-483 | Me | Et | H | H | $SO_2CH_2$ | $CH_2CO_2Me$ | |
| 1-484 | Me | Et | H | H | $SO_2CH_2$ | $CH_2CO_2Hex$ | |
| 1-485 | Me | Et | H | H | $SO_2CH_2$ | $CH_2OH$ | |
| 1-486 | Me | Et | H | H | $SO_2CH_2$ | $CH_2CHO$ | |
| 1-487 | Me | Me | H | H | $SO_2CH_2$ | $Ph(2,3-Cl_2)$ | 128–129 |
| 1-488 | Me | Me | H | H | $SO_2CH_2$ | $Ph(2,4-Cl_2)$ | 122–123 |
| 1-489 | Me | Me | H | H | $SO_2CH_2$ | $Ph(2,5-Cl_2)$ | 123–124 |
| 1-490 | Me | Me | H | H | $SO_2CH_2$ | $Ph(2,6-Cl_2)$ | 153–154 |
| 1-491 | Me | Me | H | H | $SO_2CH_2$ | $Ph(3,4-Cl_2)$ | 121–122 |
| 1-492 | Me | Me | H | H | $SO_2CH_2$ | $Ph(3,5-Cl_2)$ | 103–104 |
| 1-493 | Me | —$(CH_2)_4$— | H | $SO_2CH_2$ | $Ph(2,6-F_2)$ | 95–97 | |
| 1-494 | Me | Me | H | H | $SO_2CH_2$ | $Ph(2-Cl, 6-P)$ | 108–109 |
| 1-495 | Me | Me | Me | H | $SO_2CH_2$ | $Ph(2,6-F_2)$ | 1.5183 |

TABLE 21

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-496 | Me | H | Me | H | $SO_2CH_2$ | $Ph(2,6-F_2)$ | 64–65 |
| 1-497 | Me | Me | H | H | $SO_2CH_2$ | $Ph(3,4-F_2)$ | 109–110 |
| 1-498 | Me | Me | H | H | $SO_2CH_2$ | $Ph(2,5-F_2)$ | 107–108 |
| 1-499 | Me | Me | H | H | $SO_2CH_2$ | $Ph(2-F,6-NO_2)$ | 146–147 |
| 1-500 | Me | Me | H | H | $SO_2CH_2$ | $Ph(2,4,6-F3)$ | 87–88 |
| 1-501 | Me | Me | H | H | $SO_2CH_2$ | $Ph(2,3,6-F3)$ | 136–138 |
| 1-502 | Me | Me | H | H | $SO_2CH_2$ | $Ph(2,6-Et_2)$ | 50–53 |
| 1-503 | Me | Me | H | H | $SO_2CH_2$ | $Ph(2-NO_2, 3-CO_2Me)$ | 112–114 |
| 1-504 | Me | Me | H | H | $SO_2CH_2$ | $Ph(2,3-F_2)$ | 124–125 |
| 1-505 | Me | Me | H | H | $SO_2CH_2$ | $Ph(2,4-F_2)$ | 104–105 |
| 1-506 | Me | Me | H | H | $SO_2CH_2$ | $Ph(3,5-F_2)$ | 139–140 |
| 1-507 | Me | Me | H | H | $SO_2CH_2$ | $Ph(2,3,4-F_3)$ | 100–103 |
| 1-508 | Me | Me | H | H | $SO_2CH_2$ | $Ph(2,3,5-F_3)$ | 105–107 |
| 1-509 | Me | Me | H | H | $SO_2CH_2$ | $Ph(3,4,5-F_3)$ | 150–151 |
| 1-510 | Me | Me | H | H | $SO_2CH_2$ | $Ph(2,4,5-F_3)$ | 121–126 |
| 1-511 | Me | Me | H | H | $SO_2CH_2$ | $Ph(2,4-Me_2)$ | 1.5421 |
| 1-512 | Me | Me | H | H | $SO_2CH_2$ | $Ph(2,5-Me_2)$ | 65–66 |
| 1-513 | Me | Me | H | H | $SO_2CH_2$ | $Ph(3,4-Me_2)$ | 62–65 |

TABLE 21-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-514 | Me | Me | H | H | $SO_2CH_2$ | Ph(2-F, 5-$CF_3$) | 95–97 |
| 1-515 | Me | Me | H | H | $SO_2CH_2$ | Ph(2-F, 3-$CF_3$) | 109–111 |
| 1-516 | Me | Me | H | H | $SO_2CH_2$ | Ph(2-F, 4-Br) | 123–125 |
| 1-517 | Me | Me | H | H | $SO_2CH_2$ | Ph(2-$SO_2CF_3$) | 80–81 |
| 1-518 | H | —$(CH_2)_5$— | | H | $SO_2CH_2$ | Ph(2,6-$F_2$) | 65–66 |
| 1-519 | H | —$(CH_2)_6$— | | H | $SO_2CH_2$ | Ph(2,6-$F_2$) | 97–99 |
| 1-520 | Pr-c | Pr-c | H | H | $SO_2CH_2$ | Ph(2,6-$F_2$) | 95–96 |

TABLE 22

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-521 | Me | Me | H | H | $SO_2CH_2$ | Ph(2-I) | 70–72 |
| 1-522 | Me | Me | H | H | $SO_2CH_2$ | Ph(2,3-$Me_2$) | 123–124 |
| 1-523 | Me | Me | H | H | $SO_2CH_2$ | Ph(3,5-$Me_2$) | 97–98 |
| 1-524 | Me | Me | H | H | $SO_2CH_2$ | Ph(3,5-$OMe_2$) | 125–126 |
| 1-525 | Me | Me | H | H | $SO_2CH_2$ | Ph(2-Et, 6-Me) | 1.5414 |
| 1-526 | Me | Me | H | H | $SO_2CH_2$ | Ph(2-OEt, 6-F) | 1.5251 |
| 1-527 | Me | Me | H | H | $SO_2CH_2$ | Ph(2-F, 6-$CF_3$) | 69–90 |
| 1-528 | Me | Me | H | H | $SO_2CH_2$ | Ph(2-F, 4-$CF_3$) | 124–125 |
| 1-529 | Me | Me | H | H | $SO_2CH_2$ | Ph(2,4,6-$Me_3$) | 119–120 |
| 1-530 | Me | Me | H | H | $SO_2CH_2$ | Ph(2-OMe, 5-$NO_2$) | 125–126 |
| 1-531 | Me | Me | H | H | $SO_2CH_2$ | Ph(2,3,4,5,6-$F_2$) | 113–114 |

TABLE 22-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-532 | Me | H | H | H | $SO_2CH_2$ | Ph(2,6-$F_2$) | 126–127 |
| 1-533 | H | H | H | H | $SO_2CH_2$ | Ph(2,6-$F_2$) | 125–126 |
| 1-534 | Me | Me | H | H | $SO_2CH_2$ | Ph(2-F, 6-OMe) | 125–127 |
| 1-535 | Me | Me | H | H | $SO_2CH_2$ | Ph(2,6-$OMe_2$) | 165–167 |
| 1-536 | Me | Me | H | H | $SO_2CH_2$ | Ph(2,6-$OEt_2$) | 85–88 |
| 1-537 | Me | Me | H | H | $SO_2CH_2$ | Ph(2-Me, 3-$NO_2$) | 109–111 |
| 1-538 | Me | Me | H | H | $SO_2CH_2$ | Ph(2-Cl, 4-F) | 92–93 |
| 1-539 | Me | Me | H | H | $SO_2CH_2$ | Ph(4-Cl, 2-$NO_2$) | 136–137 |
| 1-540 | Me | Me | H | H | $SO_2CH_2$ | Ph(5-Me, 2-$NO_2$) | 124–125 |
| 1-541 | Me | Me | H | H | $SO_2CH_2$ | Ph(4-F, 3-$CF_3$) | 99–101 |
| 1-542 | Me | Me | H | H | $SO_2CH_2$ | Ph(3-F, 5-$CF_3$) | 87–89 |
| 1-543 | Me | Me | H | H | $SO_2CH_2$ | Ph(3,5-$(CF_3)_2$) | 130–132 |
| 1-544 | Me | Me | H | H | $SO_2CH_2$ | Ph(2,5-$(CF_2)_2$) | 100–103 |
| 1-545 | Me | Me | H | H | $SO_2CH_2$ | Ph(3,5-$Br_2$) | 115–116 |

TABLE 23

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-546 | Me | Me | H | H | $SO_2CH_2$ | Ph(3,5-$(NO_2)_2$) | 162–163 |
| 1-547 | Me | Me | H | H | $SO_2CH_2$ | Ph(2,3,5,6-$(Me)_4$) | 128–130 |
| 1-548 | Me | Me | H | H | $SO_2CH_2$ | Ph(2-F, 6-I) | 137–138 |
| 1-549 | Me | Me | H | H | $SO_2CH_2$ | Ph(2-$NH_2$, 6-F) | 118–121 |
| 1-550 | Me | Me | H | H | $SO_2CH_2$ | Ph(2,6-$F_2$, 3-Me) | 118–119 |
| 1-551 | Me | Me | H | H | $SO_2CH_2$ | Ph(4-F, 2-$CF_3$) | 50–51 |
| 1-552 | Me | Me | H | H | $SO_2CH_2$ | Ph(2-$NH_2$) | 107–109 |
| 1-553 | Me | Me | H | H | $SO_2CH_2$ | Ph(2-Pr, 6-F) | 126–127 |
| 1-554 | Me | Me | H | H | $SO_2CH_2$ | Ph(2,6-$Br_2$) | 158–160 |
| 1-555 | Me | Me | H | H | $SO_2CH_2$ | Ph(2-F, 6-$CO_2Me$) | 103–105 |
| 1-556 | Me | —$(CH_2)_5$— | | H | $SO_2CH_2$ | Ph(2,6-$F_2$) | 86–87 |
| 1-557 | Me | Me | H | H | $SO_2CH_2$ | Ph(2-F, 6-$NMe_2$) | 108–110 |
| 1-558 | Me | Me | H | H | $SO_2CH_2$ | Ph(2-F, 6-$NEt_2$) | 90–92 |
| 1-559 | Me | Me | H | H | $SO_2CH_2$ | Ph(2-$OCH_2C\equiv CH$) | 110–113 |
| 1-560 | Me | Me | H | H | $SO_2CH_2$ | Ph(2-Cl, 6-Me) | 98–100 |
| 1-561 | Me | Me | H | H | $SO_2CH_2$ | Ph(2-Cl, 6-$OCHF_2$) | 83–84 |
| 1-562 | Me | Pr-c | H | H | $SO_2CH_2$ | Ph(2-$OCHF_2$) | 1.5215 |
| 1-563 | Me | Me | H | H | $SO_2CH_2$ | Ph(2-Cl, 6-OMe) | 128–129 |
| 1-564 | Me | Me | H | H | $SO_2CH_2$ | Ph(2-Cl, 6-OEt) | 65–67 |
| 1-565 | Me | Me | H | H | $SO_2CH_2$ | Ph(2-Cl, 6-OPr-n) | 66–68 |
| 1-566 | Me | Me | H | H | $SO_2CH_2$ | Ph(2-Cl, 6-OPr-i) | 1.5402 |
| 1-567 | Me | Me | H | H | $SO_2CH_2$ | Ph(2-Cl, 6-$OCH_2CF_3$) | 92–95 |
| 1-568 | Me | Me | H | H | $SO_2CH_2$ | Ph(2-OBu-n) | 50–51 |

TABLE 23-continued

| Compound No. | R$_1$ | R$_2$ | R$_3$ | R$_4$ | Q | Y | Melting point (° C.) or refractive index (n$_D^{20}$) |
|---|---|---|---|---|---|---|---|
| 1-569 | Me | Me | H | H | SO$_2$CH$_2$ | Ph(2-F, 6-OPr-n) | 74–76.5 |
| 1-570 | Me | Me | H | H | SO$_2$CH$_2$ | Ph(2-F, 6-OPr-i) | 1.5139 |

TABLE 24

| Compound No. | R$_1$ | R$_2$ | R$_3$ | R$_4$ | Q | Y | Melting point (° C.) or refractive index (n$_D^{20}$) |
|---|---|---|---|---|---|---|---|
| 1-571 | Me | Me | H | H | SO$_2$CH$_2$ | Ph(2-F, 6-OBu-n) | 74–75 |
| 1-572 | Me | Me | H | H | SO$_2$CH$_2$ | Ph(2-Cl, 6-OBu-i) | 92–94 |
| 1-573 | Me | Me | H | H | SO$_2$CH$_2$ | Ph(2-F, 6-OCHF$_2$) | 1.4961 |
| 1-574 | Me | Me | H | H | SO$_2$CH$_2$ | Ph(2-Cl, 6-OBu-n) | 65–67 |
| 1-575 | Me | Me | H | H | SO$_2$CH(Me) | Ph(2-CF$_3$) | 1.4965 |
| 1-576 | Me | Me | H | H | SO$_2$CH$_2$ | Ph(2-F, 6-OCH$_2$C≡CH) | 102–105 |
| 1-577 | Me | Me | H | H | SO$_2$CH$_2$ | Pb(2-OCH$_2$CO$_2$Me) | 110–111 |
| 1-578 | Me | Me | H | H | SO$_2$CH$_2$ | Ph(2-OCH$_2$CO$_2$Et) | 92–93 |
| 1-579 | Me | Me | H | H | SO$_2$CH$_2$ | Ph(2-O(CH$_2$)$_2$OMe) | 1.5089 |
| 1-580 | Me | Me | H | H | SO$_2$CH$_2$ | Ph(2-O(CH$_2$)$_2$OEt) | 1.4991 |
| 1-581 | Me | Me | H | H | SO$_2$CH(Me) | Ph | 120–121 |
| 1-582 | Me | Me | H | H | SCH(Me) | Ph | 59–60 |
| 1-583 | Me | Me | H | H | SO$_2$CH$_2$ | Ph(2-Me, 6-MeO) | 92–93 |
| 1-584 | Me | Me | H | H | SO$_2$CH$_2$ | Ph(2-Me, 3-Pr-i, 6-MeO) | 108–109 |
| 1-585 | Me | Me | H | H | SO$_2$CH$_2$ | Ph(2-OEt.6-CF$_3$) | 88–89 |
| 1-586 | Me | Me | H | H | SO$_2$CH$_2$ | Ph(2-CH$_2$OEt) | 1.5318 |
| 1-587 | Me | Me | H | H | SO$_2$CH$_2$ | Ph(2-OCOMe) | 87–89 |
| 1-588 | Me | Me | H | H | SO$_2$CH$_2$ | Ph(2-OCH$_2$Ph) | 120–123 |
| 1-589 | Me | Me | H | H | SO$_2$CH$_2$ | Ph(2-OCH$_2$CH═CH$_2$) | 71–73 |
| 1-590 | Me | Me | H | H | SO$_2$CH$_2$ | Ph(2-Cl, 6-OCH$_2$CH═CH$_2$) | Unable to measure |
| 1-591 | Me | Me | H | H | SO$_2$CH$_2$ | Ph(2-Cl, 6-OCH$_2$C≡CH) | 108–111 |
| 1-592 | Me | Me | H | H | SO$_2$CH$_2$ | Ph(2-CO$_2$H) | 182–184 |
| 1-593 | Me | Me | H | H | SO$_2$CH$_2$ | Ph(2-CO$_2$Et) | 1.5332 |
| 1-594 | Me | Me | H | H | SO$_2$CH$_2$ | Ph(2-CO$_2$Pr-n) | 1.5294 |
| 1-595 | Me | Me | H | H | SO$_2$CH$_2$ | Ph(2-CO$_2$Pr-i) | 1.5252 |

TABLE 25

| Compound No. | R$_1$ | R$_2$ | R$_3$ | R$_4$ | Q | Y | Melting point (° C.) or refractive index (n$_D^{20}$) |
|---|---|---|---|---|---|---|---|
| 1-596 | Me | Me | H | H | SO$_2$CH$_2$ | Ph(2-CO$_2$Bu-n) | 1.5262 |
| 1-597 | Me | Me | H | H | SO$_2$CH$_2$ | Ph(2-CO$_2$Bu-s) | 1.5223 |
| 1-598 | Me | Me | H | H | SO$_2$CH$_2$ | Ph(2-CO$_2$Bu-i) | 64–65 |
| 1-599 | Me | Me | H | H | SO$_2$CH$_2$ | Ph(2-CO$_2$CH$_2$CH═CH$_2$) | Unable to measure |
| 1-600 | Me | Me | H | H | SO$_2$CH$_2$ | Ph(2-CO$_2$CH$_2$C≡CH) | 90–91 |
| 1-601 | Me | Me | H | H | SO$_2$CH$_2$ | Ph(2-CO$_2$Pen-c) | 78–79 |
| 1-602 | Me | Me | H | H | SO$_2$CH$_2$ | Ph(2-OEt, 6-Me) | Unable to measure |
| 1-603 | Me | Me | H | H | SO$_2$CH$_2$ | Ph(2-OPr-n, 6-Me) | Unable to measure |
| 1-604 | Me | Me | H | H | SO$_2$CH$_2$ | Ph(2-OPr-i, 6-Me) | 1.5364 |
| 1-605 | Me | Me | H | H | SO$_2$CH$_2$ | Ph(2-OBu-n, 6-Me) | Unable to measure |
| 1-606 | Me | Me | H | H | SO$_2$CH$_2$ | Ph(2-Me, 6-OCH$_2$CH═CH$_2$) | Unable to measure |
| 1-607 | Me | Me | H | H | SO$_2$CH$_2$ | Ph(2-Me, 6-OCH$_2$C≡CH) | Unable to measure |
| 1-608 | Me | Me | H | H | SO$_2$CH$_2$ | Ph(2-OCH$_2$Pr-c) | 1.5379 |
| 1-609 | Me | Me | H | H | SO$_2$CH$_2$ | Ph(2-OPen-c) | 1.5409 |
| 1-610 | Me | Me | H | H | SO$_2$CH$_2$ | Ph(2-OHex-c) | 1.5399 |
| 1-611 | Me | Me | H | H | SO$_2$CH$_2$ | Ph(2-CO$_2$CH$_2$Ph) | 96–97 |
| 1-612 | Me | Me | H | H | SO$_2$CH$_2$ | Ph(2-CO$_2$CH$_2$Ph(2-Cl)) | 1.5631 |
| 1-613 | Me | Me | H | H | SO$_2$CH$_2$ | Ph(2-CO$_2$CH$_2$Ph(3-Cl)) | 1.5661 |
| 1-614 | Me | Me | H | H | SO$_2$CH$_2$ | Ph(2-CO$_2$CH$_2$Ph(4-Cl)) | 1.5642 |

TABLE 25-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-615 | Me | Me | H | H | $SO_2CH_2$ | Ph(2-$CH_2$OBu-n) | 42–43 |
| 1-616 | Me | Me | H | H | $SO_2CH_2$ | Ph(2,3,6-$Me_3$) | 97–99 |
| 1-617 | Me | Et | H | H | $SO_2CH_2$ | Ph(2,3,6-$Me_3$) | 68–70 |
| 1-618 | Me | Me | H | H | $SO_2CH_2$ | Ph(2-Cl, 6-$CO_2$Me) | 136–137 |
| 1-619 | Me | Me | H | H | $SO_2CH_2$ | Ph(2-Cl, 6-$CO_2$Et) | 108–109 |
| 1-620 | Me | Me | H | H | $SO_2CH_2$ | Ph(2-Cl, 6-$CO_2$Pr-n) | 76–77 |

TABLE 26

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-621 | Me | Me | H | H | $SO_2CH_2$ | Ph(2-Cl, 6-$CO_2$Pr-i) | 114–115 |
| 1-622 | Me | Me | H | H | $SO_2CH_2$ | Ph(2-Cl, 6-$CO_2$Bu-n) | 94–95 |
| 1-623 | Me | Me | H | H | $SO_2CH_2$ | Ph(2-Cl, 6-$CO_2$Bu-s) | 94–97 |
| 1-624 | Me | Me | H | H | $SO_2CH_2$ | Ph(2-Cl, 6-$CO_2$Bu-i) | 99–100 |
| 1-625 | Me | Me | H | H | $SO_2CH_2$ | Ph(2-Cl, 6-$CO_2CH_2$Ph) | 121–122 |
| 1-626 | Me | Me | H | H | $SO_2CH_2$ | Ph(2-Cl, 6-$CO_2CH_2$Ph(2-Cl)) | 111–112 |
| 1-627 | Me | Me | H | H | $SO_2CH_2$ | Ph(2-Cl, 6-$CO_2CH_2$Ph(3-Cl)) | 82–83 |
| 1-628 | Me | Me | H | H | $SO_2CH_2$ | Ph(2-Cl, 6-$CO_2CH_2$Ph(4-Cl)) | 111–112 |
| 1-629 | H | $CON(Et)_2$ | H | H | $SCH_2$ | Ph(2,6-$F_2$) | 1.5372 |
| 1-630 | H | $CON(Et)_2$ | H | H | $SOCH_2$ | Ph(2,6-$F_2$) | 1.5374 |
| 1-631 | H | $CON(Et)_2$ | H | H | $SO_2CH_2$ | Ph(2,6-$F_2$) | 1.5122 |
| 1-632 | Me | Me | H | H | $SO_2CH_2$ | Ph(2-Cl, 5-OMe) | 92–93 |
| 1-633 | Me | Me | H | H | $SO_2CH_2$ | Ph(2-Cl, 5-OEt) | 114–115 |
| 1-634 | Me | Me | H | H | $SO_2CH_2$ | Ph(2-Cl, 5-OPr-n) | 95–96 |
| 1-635 | Me | Me | H | H | $SO_2CH_2$ | Ph(2-Cl, 5-OPr-i) | 64–65 |
| 1-636 | Me | Me | H | H | $SO_2CH_2$ | Ph(2-Cl, 5-OBu-n) | 87–88 |
| 1-637 | Me | Me | H | H | $SO_2CH_2$ | Ph(2-Cl, 5-$OCH_2CH=CH_2$) | 66–67 |
| 1-638 | Me | Me | H | H | $SO_2CH_2$ | Ph(2-Cl, 5-$OCH_2C\equiv CH$) | 91–92 |
| 1-639 | Me | Me | H | H | $SO_2CH_2$ | Ph(2-Et, 6-OMe) | 78–79 |
| 1-640 | Me | Me | H | H | $SO_2CH_2$ | Ph(2-Cl, 6-$CO_2$H) | 176–176.5 |
| 1-641 | Me | Me | H | H | $SO_2CH_2$ | Ph(2-F, 6-$CO_2$H) | 176–177 |
| 1-642 | Me | Me | H | H | $SO_2CH_2$ | Ph(2-F, 6-$CO_2$Et) | 67–68 |
| 1-643 | Me | Me | H | H | $SO_2CH_2$ | Ph(2-F, 6-$CO_2$Pr-n) | 55–56 |
| 1-644 | Me | Me | H | H | $SO_2CH_2$ | Ph(2-F, 6-$CO_2$Pr-i) | 92–93 |
| 1-645 | Me | Me | H | H | $SO_2CH_2$ | Ph(2-F, 6-$CO_2$Bu-n) | 94–95 |

TABLE 27

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-646 | Me | Me | H | H | $SO_2CH_2$ | Ph(2-F, 6-$CO_2$Bu-s) | 49–50 |
| 1-647 | Me | Me | H | H | $SO_2CH_2$ | Ph(2-F, 6-$CO_2$Bu-i) | 86–87 |
| 1-648 | Me | Me | H | H | $SO_2CH_2$ | Ph(2-F, 6-$CO_2CH_2$Ph) | 191–192 |
| 1-649 | Me | Me | H | H | $SO_2CH_2$ | Ph(2-F, 6-$CO_2CH_2$Ph(2-Cl)) | 89–90 |
| 1-650 | Me | Me | H | H | $SO_2CH_2$ | Ph(2-F, 6-$CO_2CH_2$Ph(3-Cl)) | 89–90 |
| 1-651 | Me | Me | H | H | $SO_2CH_2$ | Ph(2-F, 6-$CO_2CH_2$Ph(4-Cl)) | 108–109 |
| 1-652 | Me | Et | H | H | $SO_2CH_2$ | Ph(2,3,5,6-$(Me)_4$) | 94–95 |
| 1-653 | Me | Me | H | H | $SO_2CH_2$ | Ph(2-OEt, 6-Et) | 88–90 |
| 1-654 | Me | Me | H | H | $SO_2CH_2$ | Ph(2-OPr-n, 6-Et) | 1.5321 |
| 1-655 | Me | Me | H | H | $SO_2CH_2$ | Ph(2-OPr-i, 6-Et) | 1.5312 |
| 1-656 | Me | Me | H | H | $SO_2CH_2$ | Ph(2-OBu-n, 6-Et) | 43–45 |
| 1-657 | Me | Me | H | H | $SO_2CH_2$ | Ph(2-$OCH_2CH=CH_2$, 6-Et) | 1.545 |
| 1-658 | Me | Me | H | H | $SO_2CH_2$ | Ph(2-$OCH_2C\equiv CH$, 6-Et) | 1.5489 |
| 1-659 | Me | Me | H | H | $SO_2CH_2$ | Ph(2,3,5,6-$F_4$) | 129–131 |
| 1-660 | Me | Et | H | H | $SO_2CH_2$ | Ph(2,3,5,6-$F_4$) | 110–112 |
| 1-661 | Me | Me | H | H | $SO_2CH_2$ | Ph(2-$CO_2$Me, 3-Me) | |
| 1-662 | Me | Et | H | H | $SO_2CH_2$ | Ph(2-$CO_2$Me, 3-Me) | 59–61 |
| 1-663 | Me | Me | H | H | $SO_2CH_2$ | Ph(2-$CO_2$Et, 3-Me) | |
| 1-664 | Me | Et | H | H | $SO_2CH_2$ | Ph(2-$CO_2$Et, 3-Me) | 1.5292 |
| 1-665 | Me | Me | H | H | $SO_2CH_2$ | Ph(2-$CO_2$Bu-i, 3-Me) | |
| 1-666 | Me | Et | H | H | $SO_2CH_2$ | Ph(2-$CO_2$Bu-i, 3-Me) | 1.5192 |
| 1-667 | Me | Me | H | H | $SO_2CH_2$ | Ph(2,5-$Me_2$, 6-OMe) | 117–118 |

TABLE 27-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-668 | Me | Me | H | H | SO$_2$CH$_2$ | Ph(2,5-Me$_2$, 6-OEt) | 1.5309 |
| 1-669 | Me | Me | H | H | SO$_2$CH$_2$ | Ph(2,5-Me$_2$, 6-OPr-n) | 75–76 |
| 1-670 | Me | Et | H | H | SO$_2$CH$_2$ | Ph(2,3,5,6-(Me)$_4$) | |

TABLE 28

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-671 | Me | Me | H | H | SO$_2$CH$_2$ | Ph(2,3,5-(Me)$_3$, 6-OMe) | |
| 1-672 | Me | Me | H | H | SO$_2$CH$_2$ | Ph(2,3,5-(Me)$_3$, 6-OEt) | |
| 1-673 | Me | Me | H | H | SO$_2$CH$_2$ | Ph(2,3,5-(Me)$_3$, 6-OPr-n) | |
| 1-674 | Me | Me | H | H | SO$_2$CH$_2$ | Ph(2,3,5-(Me)$_3$, 6-OPr-i) | |
| 1-675 | Me | Me | H | H | SO$_2$CH$_2$ | Ph(2,5-(Me)$_2$, 3,6-Cl$_2$) | |
| 1-676 | Me | Me | H | H | SO$_2$CH$_2$ | Ph(2,5-(Me)$_2$, 3,6-Br$_2$) | |
| 1-677 | Me | Me | H | H | SO$_2$CH$_2$ | Ph(2,3,6-(Me)$_2$, 5-Cl) | |
| 1-678 | Me | Me | H | H | SO$_2$CH$_2$ | Ph(2,3,6-(Me)$_3$, 5-Br) | |
| 1-679 | Me | Me | H | H | SCH$_2$ | Ph | 1.5521 |
| 1-680 | Me | CH$_2$CO$_2$H | H | H | SO$_2$CH$_2$ | Ph(2,6-F$_2$) | |
| 1-681 | Me | CH$_2$COEt | H | H | SO$_2$CH$_2$ | Ph(2,6-F$_2$) | |
| 1-682 | Me | CH$_2$COMe | H | H | SO$_2$CH$_2$ | Ph(2,6-F$_2$) | |
| 1-683 | Me | CH$_2$CON(Et)$_2$ | H | H | SO$_2$CH$_2$ | Ph(2,6-F$_2$) | |
| 1-684 | Me | CH$_2$CON(Me)$_2$ | H | H | SO$_2$CH$_2$ | Ph(2,6-F$_2$) | |
| 1-685 | Me | CH$_2$CONHEt | H | H | SO$_2$CH$_2$ | Ph(2,6-F$_2$) | |
| 1-686 | Me | CH$_2$CONHMe | H | H | SO$_2$CH$_2$ | Ph(2,6-F$_2$) | |
| 1-687 | Me | CH$_2$COSEt | H | H | SO$_2$CH$_2$ | Ph(2,6-F$_2$) | |
| 1-688 | Me | CH$_2$COSMe | H | H | SO$_2$CH$_2$ | Ph(2,6-F$_2$) | |
| 1-689 | Me | CH$_2$OPh | H | H | SO$_2$CH$_2$ | Ph(2,6-F$_2$) | |
| 1-690 | Me | CH$_2$OPh(2-Me) | H | H | SO$_2$CH$_2$ | Ph(2,6-F$_2$) | |
| 1-691 | Me | CH$_2$OPh(2-OMe) | H | H | SO$_2$CH$_2$ | Ph(2,6-F$_2$) | |
| 1-692 | Me | CH$_2$OPh(3-Me) | H | H | SO$_2$CH$_2$ | Ph(2,6-F$_2$) | |
| 1-693 | Me | CH$_2$OPh(3-OMe) | H | H | SO$_2$CH$_2$ | Ph(2,6-F$_2$) | |
| 1-694 | Me | CH$_2$OPh(4-Me) | H | H | SO$_2$CH$_2$ | Ph(2,6-F$_2$) | |
| 1-695 | Me | CH$_2$OPh(4-OMe) | H | H | SO$_2$CH$_2$ | Ph(2,6-F$_2$) | |

TABLE 29

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-696 | Me | CH$_2$SO$_2$Et | H | H | SO$_2$CH$_2$ | Ph(2,6-F$_2$) | |
| 1-697 | Me | CH$_2$SO$_2$Me | H | H | SO$_2$CH$_2$ | Ph(2,6-F$_2$) | |
| 1-698 | Me | Et | H | H | SCH$_2$ | Ph(2,3,4,5,6-(Me)$_5$) | |
| 1-699 | Me | Et | H | H | SCH$_2$ | Ph(2,3,5-(Me)$_3$) | |
| 1-700 | Me | Et | H | H | SCH$_2$ | Ph(2,3,5-(Me)$_3$, 6-OCH$_2$CF$_3$) | |
| 1-701 | Me | Et | H | H | SCH$_2$ | Ph(2,3,5-(Me)$_3$, 6-OCHF$_2$) | |
| 1-702 | Me | Et | H | H | SCH$_2$ | Ph(2,3,5-(Me)$_3$, 6-OEt) | |
| 1-703 | Me | Et | H | H | SCH$_2$ | Ph(213,5-(Me)$_3$, 6-OMe) | |
| 1-704 | Me | Et | H | H | SCH$_2$ | Ph(2,3,5-(Me)$_3$, 6-OPr-i) | |
| 1-705 | Me | Et | H | H | SCH$_2$ | Ph(2,3,5-(Me)$_3$, 6-OPr-n) | |
| 1-706 | Me | Et | H | H | SCH$_2$ | Ph(213,6-(Me)$_3$, 5-Br) | |
| 1-707 | Me | Et | H | H | SCH$_2$ | Ph(2,3,6-(Me)$_3$, 5-Cl) | |
| 1-708 | Me | Et | H | H | SCH$_2$ | Ph(2,3,6-(Me)$_3$, 5-F) | |
| 1-709 | Me | Et | H | H | SCH$_2$ | Ph(2,3,6-(Me)$_3$, 5-I) | |
| 1-710 | Me | Et | H | H | SCH$_2$ | Ph(2,5-(Me)$_2$, 3,6-Br$_2$) | |
| 1-711 | Me | Et | H | H | SCH$_2$ | Ph(2,5-(Me)$_3$, 3,6-Cl$_2$) | |
| 1-712 | Me | Et | H | H | SO$_2$CH$_2$ | Ph(2,3,4,5,6-(Me)$_5$) | |
| 1-713 | Me | Et | H | H | SO$_2$CH$_2$ | Ph(2,3,5-(Me)$_3$) | |
| 1-714 | Me | Et | H | H | SO$_2$CH$_2$ | Ph(2,3,5-(Me)$_3$, 6-OCH$_2$CF$_3$) | |
| 1-715 | Me | Et | H | H | SO$_2$CH$_2$ | Ph(2,3,5-(Me)$_3$, 6-OCHF$_2$) | |
| 1-716 | Me | Et | H | H | SO$_2$CH$_2$ | Ph(2,3,5-(Me)$_3$, 6-OEt) | |
| 1-717 | Me | Et | H | H | SO$_2$CH$_2$ | Ph(2,3,5-(Me)$_3$, 6-OMe) | |
| 1-718 | Me | Et | H | H | SO$_2$CH$_2$ | Ph(2,3,5-(Me)$_3$, 6-OPr-i) | |
| 1-719 | Me | Et | H | H | SO$_2$CH$_2$ | Ph(2,3,5-(Me)$_3$, 6-OPr-n) | |
| 1-720 | Me | Et | H | H | SO$_2$CH$_2$ | Ph(2,3,6-(Me)$_3$, 5-Br) | |

TABLE 30

| Compound No. | R₁ | R₂ | R₃ | R₄ | Q | Y | Melting point (° C.) or refractive index ($n_D^{20}$) |
|---|---|---|---|---|---|---|---|
| 1-721 | Me | Et | H | H | SO₂CH₂ | Ph(2,3,6-(Me)₃, 5-Cl) | |
| 1-722 | Me | Et | H | H | SO₂CH₂ | Ph(2,3,6-(Me)₃, 5-F) | |
| 1-723 | Me | Et | H | H | SO₂CH₂ | Ph (2,3,6-(Me)₃, ,5-I) | |
| 1-724 | Me | Et | H | H | SO₂CH₂ | Ph(2,5-(Me)₂, 3,6-Br₂) | |
| 1-725 | Me | Et | H | H | SO₂CH₂ | Ph (2,5-(Me)₂, 3,6-Cl₂) | |
| 1-726 | Me | Et | H | H | SOCH₂ | Ph(2,3,4,5,6-(Me)₅) | |
| 1-727 | Me | Et | H | H | SOCH₂ | Ph(2,3,5-(Me)₃) | |
| 1-728 | Me | Et | H | H | SOCH₂ | Ph(2,3,5-(Me)₃, 6-OCH₂CF₃) | |
| 1-729 | Me | Et | H | H | SOCH₂ | Ph(2,3,5-(Me)₃, 6-OCHF₂) | |
| 1-730 | Me | Et | H | H | SOCH₂ | Ph(2,3,5-(Me)₃, 6-OEt) | |
| 1-731 | Me | Et | H | H | SOCH₂ | Ph(2,3,5-(Me)₃, 6-OMe) | |
| 1-732 | Me | Et | H | H | SOCH₂ | Ph(2,3,5-(Me)₃, 6-OPr-i) | |
| 1-733 | Me | Et | H | H | SOCH₂ | Ph(2,3,5-(Me)₃, 6-OPr-n) | |
| 1-734 | Me | Et | H | H | SOCH₂ | Ph(2,3,6-(Me)₃, 5-Br) | |
| 1-735 | Me | Et | H | H | SOCH₂ | Ph(2,3,6-(Me)₃, 5-Cl) | |
| 1-736 | Me | Et | H | H | SOCH₂ | Ph(2,3,6-(Me)₃, 5-F) | |
| 1-737 | Me | Et | H | H | SOCH₂ | Ph(2,3,6-(Me)₃, 5-I) | |
| 1-738 | Me | Et | H | H | SOCH₂ | Ph(2,5-(Me)₂, 3,6-Br₂) | |
| 1-739 | Me | Et | H | H | SOCH₂ | Ph(2,5-(Me)₂, 3,6-Cl₂) | |
| 1-740 | Me | Me | H | H | SCH₂ | Ph(2,3,4,5,6-(Me)₅) | |
| 1-741 | Me | Me | H | H | SCH₂ | Ph(2,3,5-(Me)₃) | |
| 1-742 | Me | Me | H | H | SCH₂ | Ph(2,3,5-(Me)₃, 6-OCH₂CF₃) | |
| 1-743 | Me | Me | H | H | SCH₂ | Ph(2,3,5-(Me)₃, 6-OCHF₂) | |
| 1-744 | Me | Me | H | H | SCH₂ | Ph(2,3,5-(Me)₃, 6-OEt) | |
| 1-745 | Me | Me | H | H | SCH₂ | Ph(2,3,5-(Me)₃, 6-OMe) | |

TABLE 31

| Compound No. | R₁ | R₂ | R₃ | R₄ | Q | Y | Melting point (° C.) or refractive index ($n_D^{20}$) |
|---|---|---|---|---|---|---|---|
| 1-746 | Me | Me | H | H | SCH₂ | Ph(2,3,5-(Me)₃, 6-OPr-i) | |
| 1-747 | Me | Me | H | H | SCH₂ | Ph(2,3,5-(Me)₃, 6-OPr-n) | |
| 1-748 | Me | Me | H | H | SCH₂ | Ph(2,3,5,6-(Me)₄) | |
| 1-749 | Me | Me | H | H | SCH₂ | Ph(2,3,6-(Me)₃, 5-Br) | |
| 1-750 | Me | Me | H | H | SCH₂ | Ph(2,3,6-(Me)₃, 5-Cl) | |
| 1-751 | Me | Me | H | H | SCH₂ | Ph(2,3,6-(Me)₃, 5-F) | |
| 1-752 | Me | Me | H | H | SCH₂ | Ph(2,3,6-(Me)₃, 5-I) | |
| 1-753 | Me | Me | H | H | SCH₂ | Ph(2,3-Me₂) | |
| 1-754 | Me | Me | H | H | SCH₂ | Ph(2,4-Me₂) | |
| 1-755 | Me | Me | H | H | SCH₂ | Ph(2,5-(Me)₂, 3,6-Br₂) | |
| 1-756 | Me | Me | H | H | SCH₂ | Ph(2,5-(Me)₂, 3,6-Cl₂) | |
| 1-757 | Me | Me | H | H | SCH₂ | Ph(2,5-Me₂) | |
| 1-758 | Me | Me | H | H | SCH₂ | Ph(2,6-Me₂) | |
| 1-759 | Me | Me | H | H | SCH₂ | Ph(2-Br) | |
| 1-760 | Me | Me | H | H | SCH₂ | Ph(2-Bu) | |
| 1-761 | Me | Me | H | H | SCH₂ | Ph(2-Bu-i) | |
| 1-762 | Me | Me | H | H | SCH₂ | Ph(2-Bu-s) | |
| 1-763 | Me | Me | H | H | SCH₂ | Ph(2-Bu-t) | |
| 1-764 | Me | Me | H | H | SCH₂ | Ph(2-CF₃) | |
| 1-765 | Me | Me | H | H | SCH₂ | Ph(2-Cl) | |
| 1-766 | Me | Me | H | H | SCH₂ | Ph(2-Et) | |
| 1-767 | Me | Me | H | H | SCH₂ | Ph(2-F) | |
| 1-768 | Me | Me | H | H | SCH₂ | Ph(2-Hex) | |
| 1-769 | Me | Me | H | H | SCH₂ | Ph(2-Me) | |
| 1-770 | Me | Me | H | H | SCH₂ | Ph(2-OCF₃) | |

TABLE 32

| Compound No. | R₁ | R₂ | R₃ | R₄ | Q | Y | Melting point (° C.) or refractive index ($n_D^{20}$) |
|---|---|---|---|---|---|---|---|
| 1-771 | Me | Me | H | H | SCH₂ | Ph(2-OCHF₂) | |
| 1-772 | Me | Me | H | H | SCH₂ | Ph(2-OEt) | |
| 1-773 | Me | Me | H | H | SCH₂ | Ph(2-OHex) | |
| 1-774 | Me | Me | H | H | SCH₂ | Ph(2-OMe) | |
| 1-775 | Me | Me | H | H | SCH₂ | Ph(2-OPr) | |
| 1-776 | Me | Me | H | H | SCH₂ | Ph(2-OPr-i) | |
| 1-777 | Me | Me | H | H | SCH₂ | Ph(2-Pr) | |
| 1-778 | Me | Me | H | H | SCH₂ | Ph(2-Pr-i) | |
| 1-779 | Me | Me | H | H | SCH₂ | Ph(3,4-Me₂) | |
| 1-780 | Me | Me | H | H | SCH₂ | Ph(3,5-Me₂) | |
| 1-781 | Me | Me | H | H | SCH₂ | Ph(3-Br) | |
| 1-782 | Me | Me | H | H | SCH₂ | Ph(3-Bu) | |
| 1-783 | Me | Me | H | H | SCH₂ | Ph(3-Bu-i) | |
| 1-784 | Me | Me | H | H | SCH₂ | Ph(3-Bu-s) | |
| 1-785 | Me | Me | H | H | SCH₂ | Ph(3-Bu-t) | |
| 1-786 | Me | Me | H | H | SCH₂ | Ph(3-CF₃) | |
| 1-787 | Me | Me | H | H | SCH₂ | Ph(3-Cl) | |
| 1-788 | Me | Me | H | H | SCH₂ | Ph(3-Et) | |
| 1-789 | Me | Me | H | H | SCH₂ | Ph(3-F) | |
| 1-790 | Me | Me | H | H | SCH₂ | Ph(3-Hex) | |
| 1-791 | Me | Me | H | H | SCH₂ | Ph(3-Me) | |
| 1-792 | Me | Me | H | H | SCH₂ | Ph(3-OCF₃) | |
| 1-793 | Me | Me | H | H | SCH₂ | Ph(3-OCHF₂) | |
| 1-794 | Me | Me | H | H | SCH₂ | Ph(3-OEt) | |
| 1-795 | Me | Me | H | H | SCH₂ | Ph(3-OHex) | |

TABLE 33

| Compound No. | R₁ | R₂ | R₃ | R₄ | Q | Y | Melting point (° C.) or refractive index ($n_D^{20}$) |
|---|---|---|---|---|---|---|---|
| 1-796 | Me | Me | H | H | SCH₂ | Ph(3-OMe) | |
| 1-797 | Me | Me | H | H | SCH₂ | Ph(3-OPr) | |

TABLE 33-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-798 | Me | Me | H | H | $SCH_2$ | Ph(3-OPr-i) | |
| 1-799 | Me | Me | H | H | $SCH_2$ | Ph(3-Pr) | |
| 1-800 | Me | Me | H | H | $SCH_2$ | Ph(3-Pr-i) | |
| 1-801 | Me | Me | H | H | $SCH_2$ | Ph(4-Br) | |
| 1-802 | Me | Me | H | H | $SCH_2$ | Ph(4-Bu) | |
| 1-803 | Me | Me | H | H | $SCH_2$ | Ph(4-Bu-i) | |
| 1-804 | Me | Me | H | H | $SCH_2$ | Ph(4-Bu-s) | |
| 1-805 | Me | Me | H | H | $SCH_2$ | Ph(4-Bu-t) | |
| 1-806 | Me | Me | H | H | $SCH_2$ | Ph(4-$CF_3$) | |
| 1-807 | Me | Me | H | H | $SCH_2$ | Ph(4-Cl) | |
| 1-808 | Me | Me | H | H | $SCH_2$ | Ph(4-Et) | |
| 1-809 | Me | Me | H | H | $SCH_2$ | Ph(4-F) | |
| 1-810 | Me | Me | H | H | $SCH_2$ | Ph(4-Hex) | |
| 1-811 | Me | Me | H | H | $SCH_2$ | Ph(4-Me) | |
| 1-812 | Me | Me | H | H | $SCH_2$ | Ph(4-$OCF_3$) | |
| 1-813 | Me | Me | H | H | $SCH_2$ | Ph(4-$OCHF_2$) | |
| 1-814 | Me | Me | H | H | $SCH_2$ | Ph(4-OEt) | |
| 1-815 | Me | Me | H | H | $SCH_2$ | Ph(4-OHex) | |
| 1-816 | Me | Me | H | H | $SCH_2$ | Ph(4-OMe) | |
| 1-817 | Me | Me | H | H | $SCH_2$ | Ph(4-OPr) | |
| 1-818 | Me | Me | H | H | $SCH_2$ | Ph(4-OPr-i) | |
| 1-819 | Me | Me | H | H | $SCH_2$ | Ph(4-Pr) | |
| 1-820 | Me | Me | H | H | $SCH_2$ | Ph(4-Pr-i) | |

TABLE 34

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-821 | Me | Me | H | H | $SO_2CH_2$ | Ph(2,3,4,5,6-$(Me)_5$) | |
| 1-822 | Me | Me | H | H | $SO_2CH_2$ | Ph(2,3,5-$(Me)_3$) | |
| 1-823 | Me | Me | H | H | $SO_2CH_2$ | Ph(2,3,5-$(Me)_3$, 6-$OCH_2CF_3$) | |
| 1-824 | Me | Me | H | H | $SO_2CH_2$ | Ph(2,3,5-$(Me)_3$, 6-$OCHF_2$) | |
| 1-825 | Me | Me | H | H | $SO_2CH_2$ | Ph(2,3,6-$(Me)_3$, 5-F) | |
| 1-826 | Me | Me | H | H | $SO_2CH_2$ | Ph(2,3,6-$(Me)_3$, 5-I) | |
| 1-827 | Me | Me | H | H | $SOCH_2$ | Ph(2,3,4,5,6-$(Me)_5$) | |
| 1-828 | Me | Me | H | H | $SOCH_2$ | Ph(2,3,5-$(Me)_3$) | |
| 1-829 | Me | Me | H | H | $SOCH_2$ | Ph(2,3,5-$(Me)_3$, 6-$OCH_2CF_3$) | |
| 1-830 | Me | Me | H | H | $SOCH_2$ | Ph(2,3,5-$(Me)_3$, 6-$OCHF_2$) | |
| 1-831 | Me | Me | H | H | $SOCH_2$ | Ph(2,3,5-$(Me)_3$, 6-OEt) | |
| 1-832 | Me | Me | H | H | $SOCH_2$ | Ph(2,3,5-$(Me)_3$, 6-OMe) | |
| 1-833 | Me | Me | H | H | $SOCH_2$ | Ph(2,3,5-$(Me)_3$, 6-OPr-i) | |
| 1-834 | Me | Me | H | H | $SOCH_2$ | Ph(2,3,5-$(Me)_3$, 6-OPr-n) | |
| 1-835 | Me | Me | H | H | $SOCH_2$ | Ph(2,3,5,6-$(Me)_4$) | |
| 1-836 | Me | Me | H | H | $SOCH_2$ | Ph(2,3,6-$(Me)_3$, 5-Br) | |
| 1-837 | Me | Me | H | H | $SOCH_2$ | Ph(2,3,6-$(Me)_3$, 5-Cl) | |
| 1-838 | Me | Me | H | H | $SOCH_2$ | Ph(2,3,6-$(Me)_3$, 5-F) | |
| 1-839 | Me | Me | H | H | $SOCH_2$ | Ph(2,3,6-$(Me)_3$, 5-I) | |
| 1-840 | Me | Me | H | H | $SOCH_2$ | Ph(2,3-$Me_2$) | |
| 1-841 | Me | Me | H | H | $SOCH_2$ | Ph(2,4-$Me_2$) | |
| 1-842 | Me | Me | H | H | $SOCH_2$ | Ph(2,5-$(Me)_2$, 3,6-$Br_2$) | |

TABLE 34-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-843 | Me | Me | H | H | $SOCH_2$ | Ph(2,5-$(Me)_2$, 3,6-$Cl_2$) | |
| 1-844 | Me | Me | H | H | $SOCH_2$ | Ph(2,5-$Me_2$) | |
| 1-845 | Me | Me | H | H | $SOCH_2$ | Ph(2,6-$Me_2$) | |

TABLE 35

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-846 | Me | Me | H | H | $SOCH_2$ | Ph(2-Br) | |
| 1-847 | Me | Me | H | H | $SOCH_2$ | Ph(2-Bu) | |
| 1-848 | Me | Me | H | H | $SOCH_2$ | Ph(2-Bu-i) | |
| 1-849 | Me | Me | H | H | $SOCH_2$ | Ph(2-Bu-s) | |
| 1-850 | Me | Me | H | H | $SOCH_2$ | Ph(2-Bu-t) | |
| 1-851 | Me | Me | H | H | $SOCH_2$ | Ph(2-$CF_3$) | |
| 1-852 | Me | Me | H | H | $SOCH_2$ | Ph(2-Cl) | |
| 1-853 | Me | Me | H | H | $SOCH_2$ | Ph(2-Et) | |
| 1-854 | Me | Me | H | H | $SOCH_2$ | Ph(2-F) | |
| 1-855 | Me | Me | H | H | $SOCH_2$ | Ph(2-Hex) | |
| 1-856 | Me | Me | H | H | $SOCH_2$ | Ph(2-Me) | |
| 1-857 | Me | Me | H | H | $SOCH_2$ | Ph(2-$OCF_3$) | |
| 1-858 | Me | Me | H | H | $SOCH_2$ | Ph(2-$OCHF_2$) | |
| 1-859 | Me | Me | H | H | $SOCH_2$ | Ph(2-OEt) | |
| 1-860 | Me | Me | H | H | $SOCH_2$ | Ph(2-OHex) | |
| 1-861 | Me | Me | H | H | $SOCH_2$ | Ph(2-OMe) | |
| 1-862 | Me | Me | H | H | $SOCH_2$ | Ph(2-OPr) | |
| 1-863 | Me | Me | H | H | $SOCH_2$ | Ph(2-OPr-i) | |
| 1-864 | Me | Me | H | H | $SOCH_2$ | Ph(2-Pr) | |
| 1-865 | Me | Me | H | H | $SOCH_2$ | Ph(2-Pr-i) | |
| 1-866 | Me | Me | H | H | $SOCH_2$ | Ph(3,4-$Me_2$) | |
| 1-867 | Me | Me | H | H | $SOCH_2$ | Ph(3,5-$Me_2$) | |
| 1-868 | Me | Me | H | H | $SOCH_2$ | Ph(3-Br) | |
| 1-869 | Me | Me | H | H | $SOCH_2$ | Ph(3-Bu) | |
| 1-870 | Me | Me | H | H | $SOCH_2$ | Ph(3-Bu-i) | |

TABLE 36

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-871 | Me | Me | H | H | $SOCH_2$ | Ph(3-Bu-s) | |
| 1-872 | Me | Me | H | H | $SOCH_2$ | Ph(3-Bu-t) | |
| 1-873 | Me | Me | H | H | $SOCH_2$ | Ph(3-$CF_3$) | |
| 1-874 | Me | Me | H | H | $SOCH_2$ | Ph(3-Cl) | |
| 1-875 | Me | Me | H | H | $SOCH_2$ | Ph(3-Et) | |
| 1-876 | Me | Me | H | H | $SOCH_2$ | Ph(3-F) | |
| 1-877 | Me | Me | H | H | $SOCH_2$ | Ph(3-Hex) | |
| 1-878 | Me | Me | H | H | $SOCH_2$ | Ph(3-Me) | |
| 1-879 | Me | Me | H | H | $SOCH_2$ | Ph(3-$OCF_3$) | |
| 1-880 | Me | Me | H | H | $SOCH_2$ | Ph(3-$OCHF_2$) | |
| 1-881 | Me | Me | H | H | $SOCH_2$ | Ph(3-OEt) | |
| 1-882 | Me | Me | H | H | $SOCH_2$ | Ph(3-OHex) | |
| 1-883 | Me | Me | H | H | $SOCH_2$ | Ph(3-OMe) | |
| 1-884 | Me | Me | H | H | $SOCH_2$ | Ph(3-OPr) | |
| 1-885 | Me | Me | H | H | $SOCH_2$ | Ph(3-OPr-i) | |
| 1-886 | Me | Me | H | H | $SOCH_2$ | Ph(3-Pr) | |
| 1-887 | Me | Me | H | H | $SOCH_2$ | Ph(3-Pr-i) | |
| 1-888 | Me | Me | H | H | $SOCH_2$ | Ph(4-Br) | |
| 1-889 | Me | Me | H | H | $SOCH_2$ | Ph(4-Bu) | |
| 1-890 | Me | Me | H | H | $SOCH_2$ | Ph(4-Bu-i) | |
| 1-891 | Me | Me | H | H | $SOCH_2$ | Ph(4-Bu-s) | |
| 1-892 | Me | Me | H | H | $SOCH_2$ | Ph(4-Bu-t) | |

TABLE 36-continued

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-893 | Me | Me | H | H | SOCH$_2$ | Ph(4-CF$_3$) | |
| 1-894 | Me | Me | H | H | SOCH$_2$ | Ph(4-Cl) | |
| 1-895 | Me | Me | H | H | SOCH$_2$ | Ph(4-Et) | |

TABLE 37

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-896 | Me | Me | H | H | SOCH$_2$ | Ph(4-F) | |
| 1-897 | Me | Me | H | H | SOCH$_2$ | Ph(4-Hex) | |
| 1-898 | Me | Me | H | H | SOCH$_2$ | Ph(4-Me) | |
| 1-899 | Me | Me | H | H | SOCH$_2$ | Ph(4-OCF$_3$) | |
| 1-900 | Me | Me | H | H | SOCH$_2$ | Ph(4-OCHF$_2$) | |
| 1-901 | Me | Me | H | H | SOCH$_2$ | Ph(4-OEt) | |
| 1-902 | Me | Me | H | H | SOCH$_2$ | Ph(4-OHex) | |
| 1-903 | Me | Me | H | H | SOCH$_2$ | Ph(4-OMe) | |
| 1-904 | Me | Me | H | H | SOCH$_2$ | Ph(4-OPr) | |
| 1-905 | Me | Me | H | H | SOCH$_2$ | Ph(4-OPr-i) | |
| 1-906 | Me | Me | H | H | SOCH$_2$ | Ph(4-Pr) | |
| 1-907 | Me | Me | H | H | SOCH$_2$ | Ph(4-Pr-i) | |
| 1-908 | Me | Me | H | CH$_2$Pr-c | SO$_2$CH$_2$ | Ph(2,6-F$_2$) | |
| 1-909 | Me | Me | H | CH$_2$CF$_3$ | SO$_2$CH$_2$ | Ph(2,6-F$_2$) | |
| 1-910 | Me | Me | H | CH$_2$OMe | SO$_2$CH$_2$ | Ph(2,6-F$_2$) | |
| 1-911 | Me | Me | H | CH$_2$Pr-c | SOCH$_2$ | Ph(2,6-F$_2$) | |
| 1-912 | Me | Me | H | CH$_2$CF$_3$ | SOCH$_2$ | Ph(2,6-F$_2$) | |
| 1-913 | Me | Me | H | CH$_2$OMe | SOCH$_2$ | Ph(2,6-F$_2$) | |
| 1-914 | Me | Me | H | CH$_2$Pr-c | SCH$_2$ | Ph(2,6-F$_2$) | |
| 1-915 | Me | Me | H | CH$_2$CF$_3$ | SCH$_2$ | Ph(2,6-F$_2$) | |
| 1-916 | Me | Me | H | CH$_2$OMe | SCH$_2$ | Ph(2,6-F$_2$) | |
| 1-917 | Me | Me | H | Pr-c | SCH$_2$ | Ph(2,6-F$_2$) | |
| 1-918 | Me | Me | H | Pr-c | SOCH$_2$ | Ph(2,6-F$_2$) | |
| 1-919 | Me | Me | H | Pr-c | SO$_2$CH$_2$ | Ph(2,6-F$_2$) | |
| 1-920 | Me | Me | H | H | SO$_2$CH$_2$ | CH$_2$OCH$_2$C≡CH | |

TABLE 38

| Compound No. | $R_1$ | $R_2$ | $R_3$ | $R_4$ | Q | Y | Melting point (° C.) or refractive index ($n_D^{20}$) |
|---|---|---|---|---|---|---|---|
| 1-921 | Me | Me | H | H | SO$_2$CH$_2$ | Ph(2-OC$_2$H$_4$CO$_2$Me) | |
| 1-922 | Me | Me | H | H | SO$_2$CH$_2$ | Ph(2-OC$_2$H$_4$COMe) | |
| 1-923 | Me | Me | H | H | SO$_2$CH$_2$ | Ph(2-CO$_2$Ph) | |
| 1-924 | Me | Me | H | H | SCH$_2$ | Ph(2,3,5-(Me)$_3$, 6-F) | |
| 1-925 | Me | Me | H | H | SCH$_2$ | Ph(2,3,5-(Me)$_3$, 6-Cl) | |
| 1-926 | Me | Me | H | H | SCH$_2$ | Ph(2,3,5-(Me)$_3$, 6-Br) | |
| 1-927 | Me | Et | H | H | SCH$_2$ | Ph(2,3,5-(Me)$_3$, 6-F) | |
| 1-928 | Me | Et | H | H | SCH$_2$ | Ph(2,3,5-(Me)$_3$, 6-Cl) | |
| 1-929 | Me | Et | H | H | SCH$_2$ | Ph(2,3,5-(Me)$_3$, 6-Br) | |
| 1-930 | Me | Me | H | H | SOCH$_2$ | Ph(2,3,5-(Me)$_3$, 6-F) | |
| 1-931 | Me | Me | H | H | SOCH$_2$ | Ph(2,3,5-(Me)$_3$, 6-Cl) | |
| 1-932 | Me | Me | H | H | SOCH$_2$ | Ph(2,3,5-(Me)$_3$, 6-Br) | |
| 1-933 | Me | Et | H | H | SOCH$_2$ | Ph(2,3,5-(Me)$_3$, 6-F) | |
| 1-934 | Me | Et | H | H | SOCH$_2$ | Ph(2,3,5-(Me)$_3$, 6-Cl) | |
| 1-935 | Me | Et | H | H | SOCH$_2$ | Ph(2,3,5-(Me)$_3$, 6-Br) | |
| 1-936 | Me | Me | H | H | SO$_2$CH$_2$ | Ph(2,3,5-(Me)$_3$, 6-F) | |
| 1-937 | Me | Me | H | H | SO$_2$CH$_2$ | Ph(2,3,5-(Me)$_3$, 6-Cl) | |
| 1-938 | Me | Me | H | H | SO$_2$CH$_2$ | Ph(2,3,5-(Me)$_3$, 6-Br) | |
| 1-939 | Me | Et | H | H | SO$_2$CH$_2$ | Ph(2,3,5-(Me)$_3$, 6-F) | |
| 1-940 | Me | Et | H | H | SO$_2$CH$_2$ | Ph(2,3,5-(Me)$_3$, 6-Cl) | |
| 1-941 | Me | Et | H | H | SO$_2$CH$_2$ | Ph(2,3,5-(Me)$_3$, 6-Br) | |

TABLE 39

![structure]

| Compound No. | $R_1$ | $R_2$ | $R_3$ | $R_4$ | Q—Y | Melting point (° C.) or refractive index ($n_D^{20}$) |
|---|---|---|---|---|---|---|
| 2-1 | Me | Me | H | H | $SO_2Me$ | 82–84 |
| 2-2 | Me | Me | H | H | $SO_2Et$ | 59–60 |
| 2-3 | Me | Me | H | H | $SO_2Pr$ | |
| 2-4 | Me | Me | H | H | $SO_2Pr$-i | |
| 2-5 | Me | Me | H | H | $SO_2Bu$ | |
| 2-6 | Me | Me | H | H | $SO_2Bu$-i | |
| 2-7 | Me | Me | H | H | $SO_2Bu$-s | |
| 2-8 | Me | Me | H | H | $SO_2Bu$-t | |
| 2-9 | Me | Me | H | H | $SO_2Hex$ | |
| 2-10 | Me | Me | H | H | $SO_2C_8H_{17}$ | |
| 2-11 | Me | Me | H | H | $SO_2C_{10}H_{21}$ | |
| 2-12 | Me | Et | H | H | $SO_2Me$ | 1.4771 |
| 2-13 | Me | Et | H | H | $SO_2Et$ | 1.4759 |
| 2-14 | Me | Et | H | H | $SO_2Pr$ | 1.4742 |
| 2-15 | Me | Et | H | H | $SO_2Pr$-i | 1.4752 |
| 2-16 | Me | Et | H | H | $SO_2Bu$ | 1.4711 |
| 2-17 | Me | Et | H | H | $SO_2Bu$-i | 1.4696 |
| 2-18 | Me | Et | H | H | $SO_2Bu$-s | 1.4750 |
| 2-19 | Me | Et | H | H | $SO_2Bu$-t | 30–31.5 |
| 2-20 | Me | Et | H | H | $SO_2Hex$ | |
| 2-21 | Me | Et | H | H | $SO_2C_8H_{17}$ | 1.4685 |
| 2-22 | Me | Et | H | H | $SO_2C_{10}H_{21}$ | 1.4705 |
| 2-23 | Me | Pr-c | H | H | $SO_2CH_2$ | 1.4921 |
| 2-24 | Me | H | Me | H | $SO_2Me$ | 1.4778 |
| 2-25 | Me | —$(CH_2)_4$— | | H | $SO_2Me$ | 1.5016 |
| 2-26 | H | —$(CH_2)_5$— | | H | $SO_2Me$ | 1.5122 |
| 2-27 | H | —$(CH_2)_6$— | | H | $SO_2Me$ | 1.5135 |
| 2-28 | —$(CH_2)_2$— | | H | H | $SO_2Me$ | 65–67 |
| 2-29 | —$(CH_2)_3$ | | H | H | $SO_2Me$ | 72–73 |

The present compound represented by the general formula [I] can be produced according to the processes shown below. However, the production process is not restricted to these.
<Production Process 1>Steps 1 to 4

[wherein L is a leaving group such as halogen atom, phenylsulfonyl group which may be substituted with $C_1$ to $C_4$ alkyl group (e.g. p-toluenesulfonyl group), $C_1$ to $C_4$ alkylsulfonyl group (e.g. methylsulfonyl group) or the like (chlorine atom is preferred); and $R_1$, $R_2$, $R_3$, $R_4$, $R_5$, $R_6$, Y and m have the same definitions as given above].

The above production process is explained in detail on each step.

(Step 1)

A compound represented by the general formula [II] is reacted with a mercaptan derivative represented by the general formula [III] in the presence of a base in an appropriate solvent or without using any solvent (preferably in an appropriate solvent), or with a salt (which is a sodium salt or a potassium salt) of a mercaptan derivative represented by the general formula [III] in an appropriate solvent, whereby an intended sulfide derivative represented by the general formula [IV] can be obtained.

The solvent can be exemplified by ethers such as diethyl ether, diethoxyethane, dioxane, tetrahydrofuran (THF) and the like; halogenated hydrocarbons such as dichloromethane, chloroform, carbon tetrachloride, dichloroethane, chlorobenzene, dichlorobenzene and the like; amides such as N,N-dimethylacetamide, N,N-dimethylformamide (DMF), N-methyl-2-pyrrolidinone and the like; sulfur compounds such as dimethyl sulfoxide (DMSO), sulfolane and the like; aromatic hydrocarbons such as benzene, toluene, xylene and the like; alcohols such as methanol, ethanol, propanol, isopropanol, butanol, tert-butanol and the like; ketones such as acetone, 2-butanone and the like; nitriles such as acetonitrile and the like; water; and mixtures thereof.

The base can be exemplified by metal hydrides such as sodium hydride and the like; alkali metal amides such as sodium amide, lithium diisopropylamide and the like; organic bases such as pyridine, triethylamine, 1,8-diazabicyclo[5.4.0]-7-undecene and the like; inorganic bases such as alkali metal hydroxide (e.g. sodium hydroxide or potassium hydroxide), alkaline earth metal hydroxide (e.g. calcium hydroxide or magnesium hydroxide), alkali metal carbonate (e.g. sodium carbonate or potassium carbonate), alkali metal bicarbonate (e.g. sodium hydrogen-

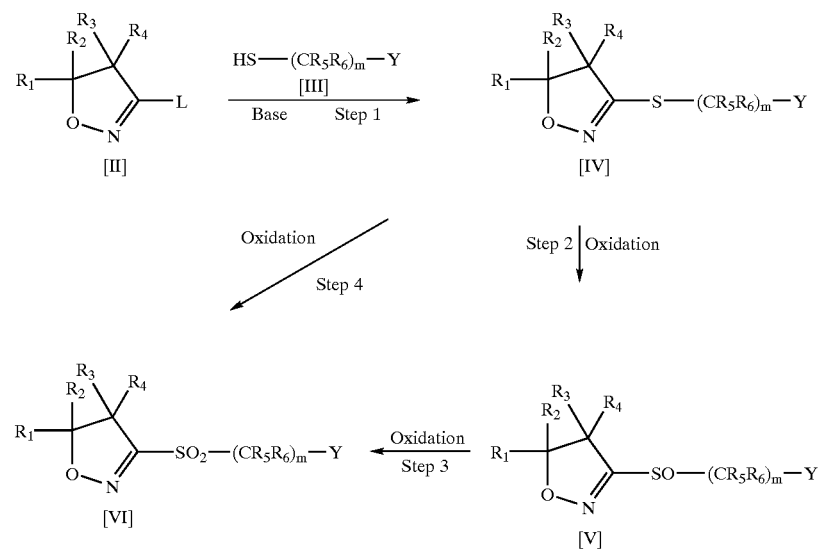

carbonate or potassium hydrogencarbonate) and the like; and alcohol metal salts such as sodium methoxide, potassium tert-butoxide and the like.

The reaction temperature is any temperature between 0° C. and the reflux temperature of the reaction system, preferably a temperature between 10 and 100° C. The reaction time differs depending upon the compounds used but is 0.5 to 24 hours.

(Step 2)

In the oxidation reaction of the sulfide derivative represented by the general formula [IV], the sulfide derivative of the general formula [IV] is reacted with an oxidizing agent (for example, an organic peroxide such as m-chloroperbenzoic acid, performic acid or peracetic acid, or an inorganic peroxide such as hydrogen peroxide, potassium permanganate or sodium periodate) in an appropriate solvent, whereby an intended sulfoxide derivative represented by the general formula [V] can be obtained.

The solvent can be exemplified by halogenated hydrocarbons such as dichloromethane, chloroform, dichloroethane, carbon tetrachloride, chlorobenzene, dichlorobenzene and the like; ethers such as dioxane, tetrahydrofuran (THF), dimethoxyethane, diethyl ether and the like; amides such as N,N-dimethylacetamide, N,N-dimethylformamide (DMF), N-methyl-2-pyrrolidinone and the like; alcohols such as methanol, ethanol, propanol, isopropanol, butanol, tert-butanol and the like; ketones such as acetone, 2-butanone and the like; nitriles such as acetonitrile and the like; acetic acid; water; and mixtures thereof.

The reaction temperature is any temperature between 0° C. and the reflux temperature of the reaction system, preferably a temperature between 10 and 60° C. The reaction time differs depending upon the compounds used but is 1 to 72 hours.

(Step 3)

The sulfoxide derivative represented by the general formula [V] is reacted with an oxidizing agent (the same as described in the step 2) in an appropriate solvent (the same as described in the step 2), whereby an intended sulfone derivative represented by the general formula [VI] can be obtained.

The reaction temperature is any temperature between 0° C. and the reflux temperature of the reaction system, preferably a temperature between 10 and 60° C. The reaction time differs depending upon the compounds used but is 1 to 72 hours.

(Step 4)

When, in the oxidation reaction of the sulfide derivative represented by the general formula [IV], the oxidizing agent is used by an appropriate amount, the sulfone derivative represented by the general formula [VI] can be obtained without isolating the sulfoxide derivative represented by the general formula [V].

That is, the sulfide derivative represented by the general formula [IV] is reacted with an oxidizing agent (the same as described in the step 2) in an appropriate solvent (the same as described in the step 2), whereby an intended sulfoxide derivative represented by the general formula [V] can be obtained.

The reaction temperature is any temperature between 0° C. and the reflux temperature of the reaction system, preferably a temperature between 10 and 60° C. The reaction time differs depending upon the compounds used but is 1 to 72 hours.

A compound represented by the genera, formula [II] wherein L is a halogen atom, can be synthesized by the following step 5.

(Step 5)

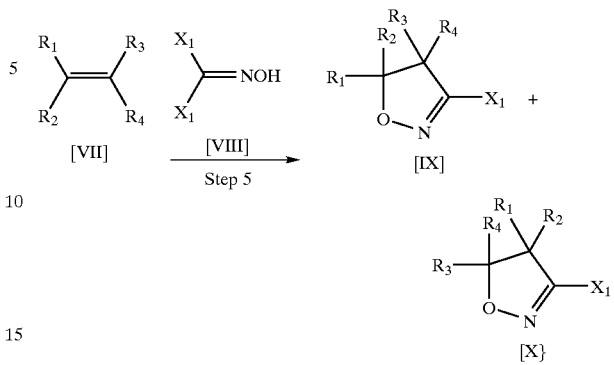

[wherein $X_1$ is a halogen atom (a chlorine atom is preferred), and $R_1$, $R_2$, $R_3$ and $R_4$ have the same definitions as given above].

That is, a compound represented by the general formula [VIII] is reacted with an olefin derivative represented by the general formula [VII] in the presence of a base in an appropriate solvent or without using any solvent (preferably in an appropriate solvent), whereby isoxazoline compounds represented by the general formulas [IX] and [X] can be obtained. When both $R_3$ and $R_4$ are a hydrogen atom, an isoxazoline compound represented by the general formula [IX] is obtained preferentially.

The solvent can be exemplified by ethers such as ethylene glycol dimethyl ether, ethylene glycol diethyl ether, diethyl ether, dioxane, tetrahydrofuran and the like; halogenated hydrocarbons such as dichloroethane, carbon tetrachloride, chlorobenzene, dichlorobenzene and the like; aromatic hydrocarbons such as benzene, toluene, xylene and the like; acetic acid esters such as ethyl acetate, butyl acetate and the like; water; and mixtures thereof.

The base can be exemplified by alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal bicarbonates such as sodium hydrogencarbonate, potassium hydrogencarbonate and the like; alkali metal acetates such as sodium acetate, potassium acetate and the like; alkali metal fluorides such as sodium fluoride, potassium fluoride and the like; and organic bases such as pyridine, triethylamine, 1,8-diazabicyclo[5.4.0]-7-undecene and the like.

The reaction temperature is any temperature between 0° C. and the reflux temperature of the reaction system, preferably a temperature between 10 and 80° C. The reaction time differs depending upon the compounds used but is 0.5 hour to 2 weeks.

Incidentally, the compound represented by the general formula [VII] used in the above step 5 as an intermidiate can be a commercial product or synthesized by a known reaction such as Wittig reaction or the like. The compound represented by the general formula [VIII] can be synthesized by, for example, a method described in Liebigs Annalen der Chemie, p. 985 (1989).

<Production Process 2>Step 6

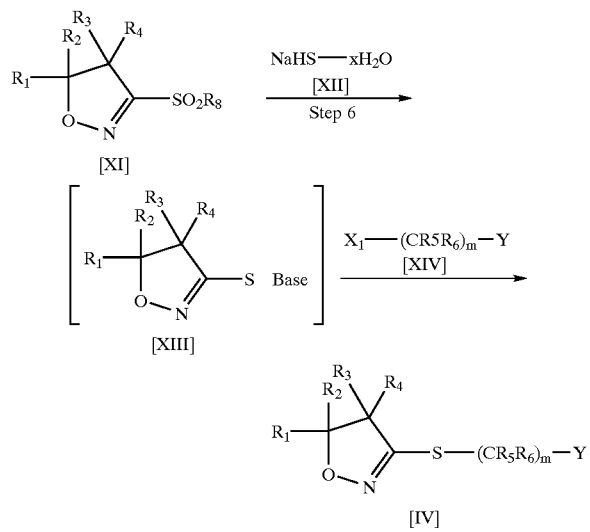

(wherein $X_1$, $R_1$, $R_2$, $R_3$, $R_4$, $R_5$, $R_6$, Y and m have the same definitions as given above; $R_0$ is a $C_1$ to $C_4$ alkyl group or a benzyl group, preferably a lower alkyl group such as methyl group, ethyl group or the like; and base is the same as described in the step 1).

The sulfide derivative represented by the general formula [IV], described in the Production Process 1 can be obtained also by the following process.

That is, a compound represented by the general formula [XI] is reacted with sodium hydrogensulfide hydrate represented by the general formula [XII] in the presence of a base (the same as described in the step 1) in an appropriate solvent or without using any solvent (preferably in an appropriate solvent) (Rongalit may be added in some cases), whereby a mercaptan salt represented by the general formula [XIII] can be obtained in the reaction system. The reaction mixture is reacted with a halogen derivative represented by the general formula [XIV] without isolating the mercaptan salt represented by the general formula [XIII], whereby a sulfide derivative represented by the general formula [IV] can be obtained.

The solvent can be exemplified by ethers such as dioxane, tetrahydrofuran (THF) and the like; halogenated hydrocarbons such as dichloromethane, carbon tetrachloride, chlorobenzene, dichlorobenzene and the like; amides such as N,N-dimethylacetamide, N,N-dimethylformamide (DMF), N-methyl-2-pyrrolidinone and the like; sulfur compounds such as dimethyl sulfoxide (DMSO), sulfolane and the like; aromatic hydrocarbons such as benzene, toluene, xylene and the like; alcohols such as methanol, ethanol, propanol, isopropanol, butanol, tert-butanol and the like; ketones such as acetone, 2-butanone and the like; nitrites such as acetonitrile and the like; water; and mixtures thereof.

The reaction temperature is any temperature between 0° C. and the reflux temperature of the reaction system, preferably a temperature between 10 and 100° C. The reaction time differs depending upon the compounds used but is 0.5 to 24 hours.

The sulfone derivative represented by the general formula [XI] can be produced by the method shown in the Step 1 of the Production Process 1. In this case, the group —(CR$_5$R$_6$)$_n$—Y in the general formula [III] is an alkyl group or a benzyl group.

Next, the method for producing the present compound, the method for formulation with the present compound, and the application are specifically described by way of Examples. The method for producing the intermediate for the present compound is also described.

Example 1

Production Of 3-benzylthio-5,5-dimethyl-2-isoxazoline (Present Compound No. 1-679)

To a solution of 2.8 g (22.5 mmoles) of benzylmercaptan dissolved in 50 ml of dimethylformamide were added, in a nitrogen current, 3.2 g (23.2 mmoles) of anhydrous potassium carbonate and 3.0 g (22.5 mmoles) of 3-chloro-5,5-dimethyl-2-isoxazoline. The mixture was stirred at 100° C. for 2 hours to give rise to a reaction. After the completion of the reaction, the reaction mixture was poured into water, followed by extraction with ethyl acetate. The resulting organic layer was washed with water and an aqueous sodium chloride solution in this order and then dried over anhydrous magnesium sulfate. The resulting solution was subjected to vacuum distillation to remove the solvent contained therein, and the residue was purified by silica gel column chromatography to obtain 3.1 g (yield: 62.0%) of 3-benzylthio-5,5-dimethyl-2-isoxazoline as a yellow oily substance (refractive index $n_D^{20}$=1.5521).
$^1$H-NMR [CDCl$_3$/TMSδ(ppm)]: 7.24–7.39 (5H,m), 4.26 (2H,s), 2.77 (2H,s), 1.40 (6H,s)

<Example 2>

Production Of 5-ethyl-3-(2,6-difluorobenzylsulfinyl)-5-methyl-2-isoxazoline (Present Compound No. 1-199)

To a solution of 4.1 g (15.0 mmoles) of 5-ethyl-3-(2,6-difluorobenzylthio)-5-methyl-2-isoxazoline dissolved in 50 ml of chloroform was added, with ice-cooling, 4.6 g (18.8 mmoles) of m-chloroperbenzoic acid (70%). The mixture was stirred for 1 hour and then at room temperature for 12 hours to give rise to a reaction. After the completion of the reaction, the reaction mixture was poured into water, followed by extraction with chloroform. The resulting organic phase was washed with an aqueous sodium hydrogensulfite solution, an aqueous potassium carbonate solution, water and an aqueous sodium chloride solution in this order, and then dried over anhydrous magnesium sulfate. The resulting solution was subjected to vacuum distillation to remove the solvent contained therein. The residue was purified by silica gel column chromatography (solvent system: hexane-ethyl acetate) to obtain 1.5 g (yield: 34.8%) of 5-ethyl-3-(2,6-difluorobenzylsulfinyl)-5-methyl-2-isoxazloline as a white powder (melting point: 30° C. or less).
$^1$H-NMR [CDCl$_3$/TMSδ(ppm)]: 7.39–7.28 (1H, m), 7.03–6.94 (2H, m), 4.38 (2H, s), 3.04 (1H, ABq, J=17.2, Δυ=85.7 Hz)+3.12 (1H, s) 1.75 (2H, m), 1.44 (3H, s)+1.41 (3H, 3), 0.97 (3H, m)

<Example 3>

Production Of 5-ethyl-3- (2,6-difluorobenzylsulfonyl)-5-methyl-2-isoxazoline (Present Compound No. 1-200)

To a solution of 0.8 g (2.8 mmoles) of 5-ethyl-3-(2,6-difluorobenzylsulfinyl)-5-methyl-2-isoxazoline dissolved in 50 ml of chloroform was added, with ice-cooling, 1.0 g (4.1 mmoles) of m-chloroperbenzoic acid. The mixture was stirred for 1 hour and then at room temperature for 12 hours to give rise to a reaction. After the completion of the reaction, the reaction mixture was poured into water, followed by extraction with chloroform. The resulting organic phase was washed with an aqueous sodium hydrogensulfite solution, an aqueous potassium carbonate solution, water and an aqueous sodium chloride solution in this order, and then dried over anhydrous magnesium sulfate. The resulting solution was subjected to vacuum distillation to remove the solvent contained therein. The residue was purified by silica gel column chromatography (solvent system: hexane-ethyl acetate) to obtain 0.6 g (yield: 75.0%) of 5-ethyl-3-(2,6-difluorobenzylsulfonyl)-5-methyl-2-isoxazloline as a white powder (melting point: 64 to 65° C.).
$^1$H-NMR [CDCl$_3$/TMSδ(ppm)] 7.36–7.46 (1H,m), 6.98–7.04 (2H,m), 4.73 (2H,s), 3.04 (2H, ABq, J=17.2, Δυ-51.1 Hz), 1.77 (2H,q), 1.46 (3H,s), 0.97 (3H,t)

<Example 4>

Production Of 3-(2,6-difluorobenzylsulfonyl)-5,5-dimethyl-2-isoxazoline
(Present Compound No. 1-39)

To a solution of 3.9 g (15.2 mmoles) of 3-(2,6-difluorobenzylthio)-5,5-dimethyl-2-isoxazoline dissolved in 50 ml of chloroform was added, with ice-cooling, 8.5 g (34.5 mmoles) of m-chloroperbenzoic acid. The mixture was stirred for 1 hour and then at room temperature for 12 hours to give rise to a reaction. After the completion of the reaction, the reaction mixture was poured into water, followed by extraction with chloroform. The resulting organic phase was washed with an aqueous sodium hydrogensulfite solution, an aqueous potassium carbonate solution, water and an aqueous sodium chloride solution in this order, and then dried over anhydrous magnesium sulfate. The resulting solution was subjected to vacuum distillation to remove the solvent contained therein. The residue was washed with diisopropyl ether to obtain 3.4 g (yield: 77.3%) of 3-(2,6-difluorobenzylsulfonyl)-5-dimethyl-2-isoxazbline as a white powder (melting point: 110 to 111° C.).
$^1$H-NMR [CDCl$_3$/TMSδ(ppm)]: 7.35–7.45 (1H,m), 6.98–7.03 (2H,m), 4.72 (2H,s), 3.06 (2H,s), 1.51 (6H,s)

<Example 5>

Production Of 3-(2,6-difluorobenzylthio)-5,5-dimethyl-2-isoxazoline
(Present Compound No. 1-38)

To a solution of 5.0 g (28.2 mmoles) of 3-methylsulfonyl-5,5-dimethyl-2-isoxazoline (present compound No. 2-1) dissolved in 50 ml of DMF were added, with ice-cooling, 4.5 g (purity: 70%, 56.1 mmoles) of sodium hydrogensulfide hydrate, 7.8 g (56.4 mmoles) of potassium carbonate and 8.7 g (56.5 mmoles) of Rongalit. The mixture was stirred for 2 hours. Thereto was added 5.8 g (28.0 mmoles) of 2,6-difluorobenzylbenzyl bromide. The mixture was stirred at room temperature for 12 hours to give rise to a reaction. After the completion of the reaction, the reaction mixture was poured into water, followed by extraction with ethyl acetate. The resulting organic phase was washed with an aqueous sodium chloride solution and then dried over anhydrous magnesium sulfate. The resulting solution was subjected to vacuum distillation to remove the solvent contained therein. The residue was purified by silica gel column chromatography (solvent system=hexane-ethyl acetate) to obtain 5.8 g (yield: 80.0%) of 3-(2,6-difluorobenzylthio)-5,5-dimethyl-2-isoxazoline as a white powder (melting point: 77 to 80° C.).
$^1$H-NMR [CDCl$_3$/TMSδ(ppm)]: 7.20–7.28 (1H,m), 6.86–6.93 (2H,m), 4.35 (2H,s), 2.81 (2H,s), 1.43 (6H,s)<

<Example 6>

Production Of 3-methylsulfonyl-5,5-dimethyl-2-isoxazoline (Present Compound No. 2-1)

To a solution of 193.0 g (1.07 M) of 3-chloro-5,5-dimethyl-2-isoxazoline dissolved in 500 ml of DMF was dropwise added, with ice-cooling, 1.0 kg (content=15%, 2.14 M) of an aqueous sodium methanethiolate solution. The mixture was stirred at room temperature for 12 hours to give rise to a reaction. After the completion of the reaction, the reaction mixture was poured into water, followed by extraction with ethyl acetate. The resulting organic phase was washed with an aqueous sodium chloride solution and then dried over anhydrous magnesium sulfate. The resulting solution was subjected to vacuum distillation to remove the solvent contained therein, to obtain 115.0 g (yield: 74.1%) of 3-methylthio-5,5-dimethyl-2-isoxazoline. This residue (141.2 mmoles) was dissolved in 1 liter of chloroform. Thereto was added, with ice-cooling, 392.0 g (1.59 M) of m-chloroperbenzoic acid (purity: 70%), followed by stirring at that temperature for 1 hour and at room temperature for 12 hours to give rise to a reaction. After the completion of the reaction, the precipitated m-chloroperbenzoic acid was removed by filtration. The filtrate was washed with an aqueous sodium hydrogensulfite solution, water, an aqueous sodium hydrogencarbonate solution and an aqueous sodium chloride solution in this order, and then dried over anhydrous magnesium sulfate. The resulting solution was subjected to vacuum distillation to remove the solvent contained therein. The residue was washed with diisopropyl ether to obtain 77.6 g (yield: 59.1%) of 3-methylsulfonyl-5,5-dimethyl-2-isoxazoline as a white powder (melting point: 82 to 84° C.).
$^1$H-NMR [CDCl$_3$/TMSδ(ppm)]: 3.26 (3H,s), 3.12 (2H,s), 1.51 (6H,s)

(Examples Of Production Of Intermediates)

<Reference Example 1>

Production Of 3-chloro-5,5-dimethyl-2-isoxazoline (Compound IX)

534.0 g (4.0 moles) of N-chlorosuccinimide was slowly added, at 65 to 70° C., to a solution of 182.7 g (2.05 moles) of glyoxylic aldoxime dissolved in 2 liters of dimethoxyethane, followed by refluxing for 1 hour with heating. Thereto were added, with ice-cooling, 1,440.0 g (14.4 moles) of potassium hydrogencarbonate and 10 ml of water. To the mixture was added 360.0 g (6.4 moles) of 2-methylpropene, followed by stirring at room temperature for 24 hours to give rise to a reaction. The reaction mixture was poured into water, followed by extraction with isopropyl ether. The resulting organic phase was washed with water and an aqueous sodium chloride solution in this order and then dried over anhydrous magnesium sulfate. The resulting solution was subjected to vacuum distillation to remove the solvent contained therein, to obtain 107.7 g (yield: 40.0%) of 3-chloro-5,5-dimethyl-2-isoxazoline as a yellow viscous liquid.
$^1$H-NMR [CDCl$_3$/TMSδ(ppm)]: 2.93 (2H,s), 1.47 (6H,s)

<Reference Example 2>

Production Of 3-chloro-5-ethyl-5-methyl-2-isoxazoline (Compound IX)

61.9 g (463.4 mmoles) of N-chlorosuccinimide was slowly added, at 60° C., to a solution of 20.6 g (231.7 mmoles) of glyoxylic acid aldoxime dissolved in 500 ml of dimethoxyethane. Then, the mixture was refluxed for 10 minutes with heating. Thereto were added, with ice-cooling, 50 ml (463.4 mmoles) of 2-methyl-1-butene, 98.9 g (1,622 mmoles) of potassium hydrogencarbonate and 10 ml of water, followed by stirring for 12 hours to give rise to a reaction. The reaction mixture was poured into water, followed by extraction with n-hexane. The resulting organic layer was washed with water and an aqueous sodium chloride solution in this order and then dried over anhydrous magnesium sulfate. The resulting solution was subjected to vacuum distillation to remove the solvent contained therein, to obtain 13.9 g (yield: 40.6%) of 3-chloro-5-ethyl-5-methyl-2-isoxazoline as a light yellow viscous liquid.

$^1$H-NMR [CDCl$_3$/TMSδ(ppm)]: 2.91 (2H, Abq, J=17.0, Δυ=46.1 Hz), 1.73 (2H,q), 1.42 (3H,s), 0.96 (3H,t)

Below are shown the properties ($^1$H-NMR [CDCl$_3$/TMSδ (ppm)]) of the present compounds produced according to the Production Process 1 or the Production Process 2.

Present compound 1-602: 6.71–7.23 (3H,m), 4.84 (2H,s), 4.04 (2H,q), 2.81 (2H,s), 2.47 (3H,s), 1.42 (6H,s)

Present compound 1-603: 6.72–7.23 (3H,m), 4.85 (2H,s), 3.93 (2H,t), 2.82 (2H,s), 2.47 (3H,s), 1.83 (2H,m), 1.42 (6H,s), 1.04 (3H,t)

Present compound 1-605: 6.72–7.29 (3H,m), 4.85 (2H,s), 3.98 (2H,t), 2.81 (2H,s), 2.47 (3H,s), 1.80 (2H,m), 1.38 (6H,s), 0.97 (3H,t)

Present compound 1-606: 6.72–7.27 (3H,m), 6.05 (1H,m), 5.43 (1H,d), 5.29 (1H,d), 4.87 (2H,s), 4.57 (2H,d), 2.88 (2H,s), 2.48 (3H,s), 1.44 (6H,s)

Present compound 1-607: 6.92–7.30 (3H,m), 4.84 (2H,s), 4.71 (2H,d), 2.96 (2H,s) 2.52 (1H,s), 2.48 (3H,s), 1.46 (6H,s)

Present compound 1-228: 7.44–7.34 (2H,min), 7.02–6.92 (2H,m), 4.71 (2H,s), 3.86 (3H,s), 2.81 (2H, ABq, J=117.4, Δυ=54.2 Hz), 1.68 (2H,q), 1.36 (3H,s), 0.90 (3H,t)

Present cornpound 1-590: 7.28 (1H,dd), 7.08 (1H,d), 6.86 (1H,d), 6.05 (1H,m), 5.45 (1H,d), 5.32 (1H,d), 4.90 (2H,s), 4.63 (2H,d), 3.00 (2H,s), 1.47 (6H,s)

Present cornpound 1-599: 8.07 (1H,d), 7.47–7.56 (3H,m), 6.05 (1H,m), 5.42 (1H,d), 5.31 (1H,d), 5.31 (2H,s), 4.83 (2H,d), 2.94 (2H,s) 1.43 (6H,s)

The herbicide of the present invention contains, as the active ingredient, an isoxazoline derivative represented by the genera formula [I] or a salt thereof.

In using the compound of the present invention as a herbicide, the present compound may be used by itself. It can also be used in the form of a powder, a wettable powder, an emulsifiable concentrate, fine granules, granules, etc. by blending with a carrier, a surfactant, a dispersant, an adjuvant, etc. all generally used in formulation.

As the carrier used in formulation, there can be mentioned, for example, solid carriers such as talc, bentonite, clay, kaolin, diatomaceous earth, white carbon, vermiculite, calcium carbonate, slaked lime, siliceous sand, ammonium sulfate, urea and the like; and liquid carriers such as isopropyl alcohol, xylene, cyclohexane, methylnaphthalene and the like.

As the surfactant and the dispersant, there can be mentioned, for example, metal salts of alkylbenzenesulfonic acids, metal salts of dinaphthylmethanedisulfonic acid, salts of alcohol sulfates, alkylarylsulfonic acid salts, ligninsulfonic acid salts, polyoxyethylene glycol ether, polyoxyethylene alkyl aryl ethers, monoalkylates of polyoxyethylene sorbitan and the like. As the adjuvant, there can be mentioned, for example, carboxymethyl cellulose, polyethylene glycol and gum arabic. The present herbicide, when used, is diluted to an appropriate concentration and sprayed or applied directly.

The herbicide of the present invention can be used by spraying on plant foliage, application to soil, application on water surface, etc. The amount of the active ingredient used is determined appropriately so as to meet the application purpose. When the present compound is made into a powder or granules, the amount is appropriately determined in a range of 0.01 to 10% by weight, preferably 0.05 to 5% by weight. When the present compound is made into an emulsifiable concentrate or a wettable powder, the amount is appropriately determined in a range of 1 to 90% by weight, 5 to 50% by weight.

The amount of the present herbicide used varies depending upon the kind of the compound used, the target weed, the tendency of weed emergence, the environmental conditions, the type of the herbicide used, etc. When the present herbicide is used per se as in the case of a powder or granules, the amount is appropriately selected in a range of 0.1 g to 5 kg, preferably 1 g to 1 kg per 10 ares in terms of the active ingredient. When the present herbicide is used in a liquid form as in the case of an emulsifiable concentrate or a wettable powder, the amount is appropriately selected in a range of 0.1 to 50,000 ppm, preferably 10 to 10,000 ppm in terms of the active ingredient.

The compound of the present invention may be mixed as necessary with an insecticide, a fungicide, other herbicide, a plant growth-regulating agent, a fertilizer, etc.

Next, formulation from the present compound is described specifically by showing typical examples of formulation. The kinds of compounds and additives and their compounding ratios are not restricted to those shown below and can be varied widely. In the following description, "parts" refer to parts by weight.

<Formulation 1>Wettable Powder 10 parts of a compound (1-5) are mixed with 0.5 part of polyoxyethylene octylphenyl ether, 0.5 part of a sodium salt of a β-naphthalenesulfonic acid-formalin condensate, 20 parts of diatomaceous earth and 69 parts of clay. The mixture is mixed and pulverlized to obtain a wettable powder.

<Formulation 2>Wettable Powder 10 parts of a compound (1-5) are mixed with 0.5 part of polyoxyethylene octylphenyl ether, 0.5 part of a sodium salt of a β-naphthalenesulfonic acid-formalin condensate, 20 parts of diatomaceous earth, 5 parts of white carbon and 64 parts of clay. The mixture is mixed and pulverlized to obtain a wettable powder.

<Formulation 3>Wettable Powder 10 parts of a compound (1-5) are mixed with 0.5 part of polyoxyethylene octylphenyl ether, 0.5 part of a sodium salt of a β-naphthalenesulfonic acid-formalin condensate, 20 parts of diatomaceous earth, 5 parts of white carbon and 64 parts of calcium carbonate. The mixture is mixed and pulverlized to obtain a wettable powder.

<Formulation 4>Emulsifiable Concentrate

To 30 parts of a compound (1-5) are added 60 parts of an equal volume mixture of xylene and isophorone and 10 parts of a surfactant mixture of a polyoxyethylene sorbitan alkylate, a polyoxyethylene alkylaryl polymer and an alkylarylsulfonate. The resulting mixture is stirred sufficiently to obtain an emulsifiable concentrate.

<Formulation 5>Granules

There are mixed 10 parts of a compound (1-5), 80 parts of an extender which is a 1:3 mixture of talc and bentonite, 5 parts of white carbon, 5 parts of a surfactant mixture of a polyoxyethylene sorbitan alkylate, a polyoxyethylene alkylaryl polymer and an alkylarylsulfonate. The resulting mixture is kneaded sufficiently to form a paste. The paste is extruded through the eyes (diameter: 0.7 mm) of a sieve. The extrudate is dried and cut into a length of 0.5 to 1 mm to obtain granules.

Next, Test Examples of the present compound are described to show the effect of the present compound.

<Test Example 1>

Test For Herbicidal Effect By Paddy Field Soil Treatment

A paddy field soil was filled in a plastic pot of 100 cm$^2$ and subjected to puddling. Then, seeds of *Echinochloa oryzicola Vasing.* (Eo) were sowed and water was filled in a depth of 3 cm. Next day, wettable powders produced in accordance with the Formulation 1 were diluted with water and dropped on the water surface. The application amount of each wettable powder was 100 g per 10 ares in terms of the active ingredient. Then, breeding was made in a greenhouse, and the herbicidal effect of each wettable powder was examined at the 21st day from the treatment in accordance with the standard shown in Table 40. The results are shown in Tables 41 to 43.

TABLE 40

| Index | Herbicidal effect (extent of growth inhibition) or phytotoxicity |
|---|---|
| 5 | A herbicidal effect or phytotoxicity of 90% or more |
| 4 | A herbicidal effect or phytotoxicity of 70% to less than 90% |
| 3 | A herbicidal effect or phytotoxicity of 50% to less than 70% |
| 2 | A herbicidal effect or phytotoxicity of 30% to less than 50% |
| 1 | A herbicidal effect or phytotoxicity of 10% to less than 30% |
| 0 | A herbicidal effect or phytotoxicity of 0% to less than 10% |

TABLE 41

| Compound No. | Application amount (active ingredient), g/10 a | Herbicidal effect to Eo |
|---|---|---|
| 1-1 | 100 | 5 |
| 1-2 | 100 | 5 |
| 1-3 | 100 | 5 |
| 1-4 | 100 | 5 |
| 1-5 | 100 | 5 |
| 1-6 | 100 | 5 |
| 1-7 | 100 | 5 |
| 1-8 | 100 | 5 |
| 1-32 | 100 | 5 |
| 1-33 | 100 | 5 |
| 1-34 | 100 | 5 |
| 1-35 | 100 | 5 |
| 1-38 | 100 | 5 |
| 1-39 | 100 | 5 |
| 1-40 | 100 | 5 |
| 1-41 | 100 | 5 |
| 1-42 | 100 | 5 |
| 1-43 | 100 | 5 |
| 1-46 | 100 | 5 |
| 1-49 | 100 | 5 |
| 1-55 | 100 | 5 |
| 1-56 | 100 | 5 |
| 1-58 | 100 | 5 |
| 1-59 | 100 | 5 |
| 1-106 | 100 | 5 |

TABLE 41-continued

| Compound No. | Application amount (active ingredient), g/10 a | Herbicidal effect to Eo |
|---|---|---|
| 1-139 | 100 | 5 |
| 1-142 | 100 | 5 |
| 1-145 | 100 | 5 |
| 1-157 | 100 | 5 |
| 1-158 | 100 | 5 |
| 1-160 | 100 | 5 |
| 1-184 | 100 | 5 |
| 1-185 | 100 | 5 |
| 1-186 | 100 | 5 |
| 1-187 | 100 | 5 |
| 1-188 | 100 | 5 |
| 1-189 | 100 | 5 |
| 1-190 | 100 | 5 |
| 1-191 | 100 | 5 |
| 1-192 | 100 | 5 |
| 1-193 | 100 | 5 |
| 1-194 | 100 | 5 |
| 1-195 | 100 | 5 |
| 1-198 | 100 | 5 |
| 1-199 | 100 | 5 |
| 1-200 | 100 | 5 |
| 1-201 | 100 | 5 |
| 1-202 | 100 | 5 |
| 1-203 | 100 | 5 |
| 1-228 | 100 | 5 |
| 1-229 | 100 | 5 |
| 1-230 | 100 | 5 |
| 1-328 | 100 | 5 |
| 1-329 | 100 | 5 |
| 1-331 | 100 | 5 |
| 1-336 | 100 | 5 |
| 1-363 | 100 | 5 |
| 1-364 | 100 | 5 |
| 1-365 | 100 | 5 |
| 1-366 | 100 | 5 |
| 1-367 | 100 | 5 |
| 1-368 | 100 | 5 |
| 1-377 | 100 | 5 |
| 1-378 | 100 | 5 |
| 1-380 | 100 | 5 |
| 1-381 | 100 | 5 |
| 1-382 | 100 | 5 |
| 1-383 | 100 | 5 |
| 1-384 | 100 | 5 |
| 1-386 | 100 | 4 |
| 1-387 | 100 | 5 |
| 1-388 | 100 | 5 |
| 1-394 | 100 | 5 |
| 1-396 | 100 | 5 |
| 1-397 | 100 | 5 |
| 1-401 | 100 | 5 |
| 1-419 | 100 | 5 |
| 1-456 | 100 | 5 |
| 1-457 | 100 | 5 |

TABLE 42

| Compound No. | Application amount (active ingredient), g/10 a | Herbicidal effect to Eo |
|---|---|---|
| 1-487 | 100 | 5 |
| 1-488 | 100 | 5 |
| 1-489 | 100 | 5 |
| 1-490 | 100 | 5 |
| 1-491 | 100 | 5 |
| 1-492 | 100 | 5 |
| 1-493 | 100 | 5 |
| 1-494 | 100 | 5 |
| 1-495 | 100 | 5 |

TABLE 42-continued

| Compound No. | Application amount (active ingredient), g/10 a | Herbicidal effect to Eo |
|---|---|---|
| 1-496 | 100 | 5 |
| 1-497 | 100 | 5 |
| 1-498 | 100 | 5 |
| 1-499 | 100 | 5 |
| 1-500 | 100 | 5 |
| 1-501 | 100 | 5 |
| 1-502 | 100 | 5 |
| 1-503 | 100 | 5 |
| 1-504 | 100 | 5 |
| 1-505 | 100 | 5 |
| 1-506 | 100 | 5 |
| 1-507 | 100 | 5 |
| 1-508 | 100 | 5 |
| 1-509 | 100 | 5 |
| 1-510 | 100 | 5 |
| 1-511 | 100 | 5 |
| 1-512 | 100 | 5 |
| 1-513 | 100 | 5 |
| 1-514 | 100 | 5 |
| 1-515 | 100 | 5 |
| 1-516 | 100 | 5 |
| 1-517 | 100 | 5 |
| 1-518 | 100 | 5 |
| 1-519 | 100 | 5 |
| 1-520 | 100 | 5 |
| 1-521 | 100 | 5 |
| 1-522 | 100 | 5 |
| 1-523 | 100 | 5 |
| 1-524 | 100 | 5 |
| 1-525 | 100 | 5 |
| 1-526 | 100 | 5 |
| 1-527 | 100 | 5 |
| 1-528 | 100 | 5 |
| 1-529 | 100 | 5 |
| 1-530 | 100 | 5 |
| 1-531 | 100 | 5 |
| 1-532 | 100 | 5 |
| 1-533 | 100 | 5 |
| 1-534 | 100 | 5 |
| 1-535 | 100 | 5 |
| 1-536 | 100 | 5 |
| 1-537 | 100 | 5 |
| 1-538 | 100 | 5 |
| 1-539 | 100 | 5 |
| 1-540 | 100 | 5 |
| 1-541 | 100 | 5 |
| 1-542 | 100 | 5 |
| 1-543 | 100 | 5 |
| 1-544 | 100 | 5 |
| 1-545 | 100 | 5 |
| 1-546 | 100 | 5 |
| 1-547 | 100 | 5 |
| 1-548 | 100 | 5 |
| 1-549 | 100 | 5 |
| 1-550 | 100 | 5 |
| 1-551 | 100 | 5 |
| 1-552 | 100 | 4 |
| 1-553 | 100 | 5 |
| 1-554 | 100 | 5 |
| 1-555 | 100 | 5 |
| 1-556 | 100 | 5 |
| 1-559 | 100 | 5 |
| 1-560 | 100 | 5 |
| 1-561 | 100 | 5 |
| 1-562 | 100 | 5 |
| 1-563 | 100 | 5 |
| 1-564 | 100 | 5 |
| 1-565 | 100 | 5 |
| 1-566 | 100 | 5 |
| 1-567 | 100 | 5 |
| 1-568 | 100 | 5 |

TABLE 43

| Compound No. | Application amount (active ingredient), g/10 a | Herbicidal effect to Eo |
|---|---|---|
| 1-569 | 100 | 5 |
| 1-570 | 100 | 5 |
| 1-571 | 100 | 5 |
| 1-572 | 100 | 5 |
| 1-573 | 100 | 5 |
| 1-574 | 100 | 5 |
| 1-575 | 100 | 5 |
| 1-576 | 100 | 5 |
| 1-579 | 100 | 5 |
| 1-580 | 100 | 5 |
| 1-581 | 100 | 5 |
| 1-583 | 100 | 5 |
| 1-584 | 100 | 5 |
| 1-585 | 100 | 5 |
| 1-586 | 100 | 5 |
| 1-588 | 100 | 5 |
| 1-589 | 100 | 5 |
| 1-590 | 100 | 5 |
| 1-591 | 100 | 5 |
| 1-593 | 100 | 5 |
| 1-594 | 100 | 5 |
| 1-595 | 100 | 5 |
| 1-596 | 100 | 5 |
| 1-597 | 100 | 5 |
| 1-598 | 100 | 5 |
| 1-599 | 100 | 5 |
| 1-600 | 100 | 5 |
| 1-601 | 100 | 5 |
| 1-602 | 100 | 5 |
| 1-603 | 100 | 5 |
| 1-604 | 100 | 5 |
| 1-605 | 100 | 5 |
| 1-606 | 100 | 5 |
| 1-607 | 100 | 5 |
| 1-608 | 100 | 5 |
| 1-609 | 100 | 5 |
| 1-610 | 100 | 5 |
| 1-612 | 100 | 5 |
| 1-613 | 100 | 5 |
| 1-614 | 100 | 5 |
| 1-615 | 100 | 5 |
| 1-616 | 100 | 5 |
| 1-617 | 100 | 5 |
| 1-618 | 100 | 5 |
| 1-619 | 100 | 5 |
| 1-620 | 100 | 5 |
| 1-621 | 100 | 5 |
| 1-622 | 100 | 5 |
| 1-623 | 100 | 5 |
| 1-624 | 100 | 5 |
| 1-625 | 100 | 5 |
| 1-626 | 100 | 5 |
| 1-627 | 100 | 5 |
| 1-628 | 100 | 5 |
| 2-2 | 100 | 5 |
| 2-28 | 100 | 5 |
| 2-29 | 100 | 5 |

<Test Example 2>

Test For Herbicidal Effect By Upland Field Soil Treatment

An upland field soil was filed in a plastic pot of 80 cm². Seeds of *Echinochloa crus-galli* (L.) Beauv. var. *crusgall* (Ec) and *Setaria viridis* (L.) Beauv. (Se) were sowed, followed by covering with the same soil. Wettable powders produced in accordance with the Formulation 1 were diluted with water and sprayed uniformly: on the soil surface using a small sprayer, in an amount of 100 liters per 10 ares so that the amount of each active ingredient became 100 g per 10 ares. Then, breeding was made in a greenhouse, and the herbicidal effect of each wettable powder was examined at the 21st day from the treatment in accordance with the standard shown in Table 40. The results are shown in Tables 44 to 46.

TABLE 44

| Compound No. | Application amount (active ingredient), g/10 a | Herbicidal effect to Ec | Herbicidal effect to Se |
|---|---|---|---|
| 1-1 | 100 | 5 | 5 |
| 1-2 | 100 | 5 | 5 |
| 1-3 | 100 | 5 | 5 |
| 1-4 | 100 | 5 | 5 |
| 1-5 | 100 | 5 | 5 |
| 1-6 | 100 | 5 | 5 |
| 1-7 | 100 | 5 | 5 |
| 1-8 | 100 | 5 | 5 |
| 1-32 | 100 | 5 | 5 |
| 1-33 | 100 | 5 | 5 |
| 1-34 | 100 | 5 | 5 |
| 1-35 | 100 | 5 | 5 |
| 1-38 | 100 | 4 | 4 |
| 1-39 | 100 | 5 | 5 |
| 1-40 | 100 | 5 | 5 |
| 1-41 | 100 | 5 | 5 |
| 1-42 | 100 | 5 | 4 |
| 1-43 | 100 | 5 | 5 |
| 1-46 | 100 | 5 | 5 |
| 1-49 | 100 | 5 | 5 |
| 1-55 | 100 | 5 | 5 |
| 1-56 | 100 | 5 | 5 |
| 1-58 | 100 | 5 | 5 |
| 1-59 | 100 | 5 | 5 |
| 1-106 | 100 | 5 | 5 |
| 1-139 | 100 | 5 | 5 |
| 1-142 | 100 | 5 | 5 |
| 1-145 | 100 | 5 | 5 |
| 1-157 | 100 | 5 | 5 |
| 1-158 | 100 | 5 | 5 |
| 1-160 | 100 | 5 | 5 |
| 1-184 | 100 | 5 | 4 |
| 1-185 | 100 | 5 | 5 |
| 1-186 | 100 | 5 | 5 |
| 1-187 | 100 | 5 | 5 |
| 1-188 | 100 | 5 | 5 |
| 1-189 | 100 | 5 | 5 |
| 1-190 | 100 | 5 | 5 |
| 1-191 | 100 | 5 | 5 |
| 1-192 | 100 | 5 | 5 |
| 1-193 | 100 | 5 | 4 |
| 1-194 | 100 | 5 | 5 |
| 1-195 | 100 | 5 | 5 |
| 1-198 | 100 | 4 | 5 |
| 1-199 | 100 | 5 | 5 |
| 1-200 | 100 | 5 | 5 |
| 1-201 | 100 | 5 | 5 |
| 1-202 | 100 | 5 | 4 |
| 1-203 | 100 | 5 | 4 |
| 1-228 | 100 | 5 | 5 |
| 1-229 | 100 | 5 | 5 |
| 1-328 | 100 | 4 | 4 |
| 1-329 | 100 | 5 | 5 |
| 1-331 | 100 | 5 | 5 |
| 1-336 | 100 | 5 | 5 |
| 1-363 | 100 | 5 | 4 |
| 1-364 | 100 | 5 | 5 |
| 1-366 | 100 | 5 | 5 |
| 1-368 | 100 | 5 | 4 |
| 1-378 | 100 | 5 | 5 |
| 1-380 | 100 | 5 | 4 |
| 1-381 | 100 | 4 | 4 |
| 1-382 | 100 | 5 | 5 |
| 1-383 | 100 | 5 | 4 |
| 1-384 | 100 | 5 | 4 |
| 1-387 | 100 | 5 | 4 |

TABLE 44-continued

| Compound No. | Application amount (active ingredient), g/10 a | Herbicidal effect to Ec | Herbicidal effect to Se |
|---|---|---|---|
| 1-388 | 100 | 5 | 5 |
| 1-394 | 100 | 4 | — |
| 1-396 | 100 | 4 | 5 |
| 1-487 | 100 | 5 | 5 |
| 1-488 | 100 | 5 | 4 |
| 1-489 | 100 | 5 | 5 |
| 1-490 | 100 | 5 | 4 |
| 1-491 | 100 | 5 | 5 |
| 1-492 | 100 | 5 | 5 |
| 1-493 | 100 | 5 | 4 |
| 1-494 | 100 | 5 | 5 |
| 1-495 | 100 | 5 | 5 |
| 1-496 | 100 | 5 | 4 |
| 1-497 | 100 | 5 | 5 |

TABLE 45

| Compound No. | Application amount (active ingredient), g/10 a | Herbicidal effect to Ec | Herbicidal effect to Se |
|---|---|---|---|
| 1-498 | 100 | 5 | 5 |
| 1-499 | 100 | 5 | 5 |
| 1-500 | 100 | 5 | 5 |
| 1-501 | 100 | 5 | 5 |
| 1-502 | 100 | 5 | 5 |
| 1-503 | 100 | 5 | 5 |
| 1-504 | 100 | 5 | 5 |
| 1-505 | 100 | 5 | 5 |
| 1-506 | 100 | 5 | 5 |
| 1-507 | 100 | 5 | 5 |
| 1-508 | 100 | 5 | 5 |
| 1-509 | 100 | 5 | 5 |
| 1-510 | 100 | 5 | 5 |
| 1-511 | 100 | 5 | 5 |
| 1-512 | 100 | 5 | 5 |
| 1-513 | 100 | 5 | 5 |
| 1-514 | 100 | 5 | 5 |
| 1-515 | 100 | 5 | 5 |
| 1-516 | 100 | 5 | 5 |
| 1-517 | 100 | 5 | 5 |
| 1-518 | 100 | 5 | 4 |
| 1-520 | 100 | 5 | 5 |
| 1-521 | 100 | 5 | 5 |
| 1-522 | 100 | 5 | 5 |
| 1-523 | 100 | 5 | 5 |
| 1-524 | 100 | 5 | 5 |
| 1-525 | 100 | 5 | 5 |
| 1-526 | 100 | 5 | 5 |
| 1-527 | 100 | 5 | 5 |
| 1-528 | 100 | 5 | 5 |
| 1-529 | 100 | 5 | 5 |
| 1-530 | 100 | 5 | 5 |
| 1-531 | 100 | 5 | 5 |
| 1-532 | 100 | 5 | 4 |
| 1-534 | 100 | 5 | 5 |
| 1-535 | 100 | 5 | 5 |
| 1-536 | 100 | 5 | 5 |
| 1-537 | 100 | 5 | 5 |
| 1-538 | 100 | 5 | 5 |
| 1-539 | 100 | 5 | 5 |
| 1-540 | 100 | 5 | 5 |
| 1-541 | 100 | 5 | 5 |
| 1-542 | 100 | 5 | 5 |
| 1-543 | 100 | 5 | 5 |
| 1-544 | 100 | 5 | 5 |
| 1-545 | 100 | 5 | 5 |
| 1-546 | 100 | 5 | 4 |

TABLE 45-continued

| Compound No. | Application amount (active ingredient), g/10 a | Herbicidal effect to Ec | Herbicidal effect to Se |
|---|---|---|---|
| 1-547 | 100 | 5 | 5 |
| 1-548 | 100 | 5 | 5 |
| 1-549 | 100 | 5 | 5 |
| 1-550 | 100 | 5 | 5 |
| 1-551 | 100 | 5 | 5 |
| 1-553 | 100 | 5 | 5 |
| 1-554 | 100 | 5 | 5 |
| 1-555 | 100 | 5 | 5 |
| 1-556 | 100 | 5 | 4 |
| 1-559 | 100 | 5 | 5 |
| 1-560 | 100 | 5 | 5 |
| 1-561 | 100 | 5 | 5 |
| 1-562 | 100 | 5 | 5 |
| 1-563 | 100 | 5 | 5 |
| 1-564 | 100 | 5 | 5 |
| 1-565 | 100 | 5 | 5 |
| 1-566 | 100 | 5 | 5 |
| 1-567 | 100 | 5 | 5 |
| 1-568 | 100 | 5 | 5 |
| 1-569 | 100 | 5 | 5 |
| 1-570 | 100 | 5 | 5 |
| 1-571 | 100 | 5 | — |
| 1-572 | 100 | 5 | 5 |
| 1-573 | 100 | 5 | 5 |
| 1-574 | 100 | 5 | 5 |
| 1-576 | 100 | 5 | 5 |
| 1-580 | 100 | 5 | — |
| 1-581 | 100 | 5 | 5 |
| 1-583 | 100 | 5 | 5 |
| 1-585 | 100 | 5 | 5 |
| 1-586 | 100 | 5 | 5 |
| 1-589 | 100 | 5 | 5 |
| 1-590 | 100 | 5 | 5 |

TABLE 46

| Compound No. | Application amount (active ingredient), g/10 a | Herbicidal effect to Ec | Herbicidal effect to Se |
|---|---|---|---|
| 1-591 | 100 | 5 | 5 |
| 1-593 | 100 | 5 | 4 |
| 1-594 | 100 | 5 | 4 |
| 1-595 | 100 | 5 | 5 |
| 1-596 | 100 | 5 | 5 |
| 1-597 | 100 | 5 | 4 |
| 1-599 | 100 | 5 | 5 |
| 1-600 | 100 | 5 | — |
| 1-601 | 100 | 5 | — |
| 1-602 | 100 | 5 | 5 |
| 1-603 | 100 | 5 | 5 |
| 1-604 | 100 | 5 | 5 |
| 1-605 | 100 | 5 | 4 |
| 1-606 | 100 | 5 | 5 |
| 1-607 | 100 | 5 | 5 |
| 1-608 | 100 | 5 | 5 |
| 1-609 | 100 | 5 | 5 |
| 1-610 | 100 | 5 | 5 |
| 1-615 | 100 | 5 | 5 |
| 1-616 | 100 | 5 | — |
| 1-617 | 100 | 5 | 5 |
| 1-618 | 100 | 5 | 5 |
| 1-619 | 100 | 5 | 4 |
| 1-620 | 100 | 5 | 5 |
| 1-621 | 100 | 5 | 4 |
| 1-622 | 100 | 5 | — |
| 2-29 | 100 | 5 | 5 |

<Test Example 3>

Test For Herbicidal Effect By Upland Foliage Treatment

An upland field soil was filed in a plastic pot of 80 cm$^2$. Seeds of *Echinochloa crus-galli* (L.) Beauv. var. *crusgalli* (Ec) were sowed. Breeding was made in a greenhouse for 2 weeks. Wettable powders produced in accordance with the Formulation 1 were diluted with water and sprayed on the whole foliage of plants from above the plants using a small sprayer in an amount of 100 liters per 10 ares so that the amount of each active ingredient became 100 g per 10 ares. Then, breeding was made in the greenhouse, and the herbicidal effect of each wettable powder was examined at the 14th day from the treatment in accordance with the standard shown in Table 40. The results are shown in Tables 47 and 48.

TABLE 47

| Compound No. | Application amount (active ingredient), g/10 a | Herbicidal effect to Ec |
|---|---|---|
| 1-1 | 100 | 5 |
| 1-2 | 100 | 4 |
| 1-3 | 100 | 4 |
| 1-4 | 100 | 4 |
| 1-5 | 100 | 5 |
| 1-6 | 100 | 4 |
| 1-7 | 100 | 4 |
| 1-8 | 100 | 5 |
| 1-32 | 100 | 5 |
| 1-35 | 100 | 4 |
| 1-39 | 100 | 5 |
| 1-40 | 100 | 5 |
| 1-43 | 100 | 5 |
| 1-46 | 100 | 4 |
| 1-49 | 100 | 5 |
| 1-55 | 100 | 4 |
| 1-56 | 100 | 5 |
| 1-58 | 100 | 5 |
| 1-59 | 100 | 5 |
| 1-106 | 100 | 4 |
| 1-139 | 100 | 4 |
| 1-142 | 100 | 4 |
| 1-145 | 100 | 4 |
| 1-157 | 100 | 5 |
| 1-158 | 100 | 5 |
| 1-160 | 100 | 5 |
| 1-184 | 100 | 4 |
| 1-185 | 100 | 5 |
| 1-186 | 100 | 5 |
| 1-187 | 100 | 5 |
| 1-188 | 100 | 4 |
| 1-192 | 100 | 4 |
| 1-193 | 100 | 5 |
| 1-199 | 100 | 4 |
| 1-200 | 100 | 4 |
| 1-201 | 100 | 5 |
| 1-202 | 100 | 4 |
| 1-203 | 100 | 4 |
| 1-229 | 100 | 4 |
| 1-336 | 100 | 5 |
| 1-363 | 100 | 4 |
| 1-364 | 100 | 4 |
| 1-366 | 100 | 4 |
| 1-378 | 100 | 5 |
| 1-380 | 100 | 4 |
| 1-383 | 100 | 4 |
| 1-397 | 100 | 4 |
| 1-487 | 100 | 4 |
| 1-488 | 100 | 4 |
| 1-489 | 100 | 4 |
| 1-490 | 100 | 4 |
| 1-491 | 100 | 4 |

TABLE 47-continued

| Compound No. | Application amount (active ingredient), g/10 a | Herbicidal effect to Ec |
|---|---|---|
| 1-492 | 100 | 4 |
| 1-494 | 100 | 5 |
| 1-495 | 100 | 5 |
| 1-496 | 100 | 5 |
| 1-497 | 100 | 5 |
| 1-498 | 100 | 5 |
| 1-499 | 100 | 5 |
| 1-500 | 100 | 5 |
| 1-501 | 100 | 5 |
| 1-502 | 100 | 5 |
| 1-503 | 100 | 4 |
| 1-504 | 100 | 5 |
| 1-505 | 100 | 5 |
| 1-506 | 100 | 4 |
| 1-507 | 100 | 4 |
| 1-508 | 100 | 4 |
| 1-509 | 100 | 4 |
| 1-510 | 100 | 4 |
| 1-511 | 100 | 5 |
| 1-512 | 100 | 5 |
| 1-513 | 100 | 5 |
| 1-514 | 100 | 5 |
| 1-515 | 100 | 5 |
| 1-516 | 100 | 5 |
| 1-517 | 100 | 5 |
| 1-520 | 100 | 4 |
| 1-521 | 100 | 5 |
| 1-522 | 100 | 5 |

TABLE 48

| Compound No. | Application amount (active ingredient), g/10 a | Herbicidal effect to Ec |
|---|---|---|
| 1-523 | 100 | 5 |
| 1-524 | 100 | 5 |
| 1-525 | 100 | 5 |
| 1-526 | 100 | 5 |
| 1-527 | 100 | 5 |
| 1-528 | 100 | 5 |
| 1-529 | 100 | 5 |
| 1-530 | 100 | 5 |
| 1-531 | 100 | 5 |
| 1-532 | 100 | 4 |
| 1-534 | 100 | 5 |
| 1-535 | 100 | 4 |
| 1-536 | 100 | 4 |
| 1-537 | 100 | 4 |
| 1-538 | 100 | 5 |
| 1-539 | 100 | 5 |
| 1-540 | 100 | 5 |
| 1-541 | 100 | 4 |
| 1-542 | 100 | 4 |
| 1-543 | 100 | 4 |
| 1-544 | 100 | 5 |
| 1-545 | 100 | 5 |
| 1-547 | 100 | 5 |
| 1-548 | 100 | 5 |
| 1-550 | 100 | 5 |
| 1-553 | 100 | 5 |
| 1-554 | 100 | 5 |
| 1-555 | 100 | 4 |
| 1-556 | 100 | 4 |
| 1-559 | 100 | 5 |
| 1-560 | 100 | 4 |
| 1-561 | 100 | 4 |
| 1-562 | 100 | 4 |
| 1-563 | 100 | 4 |
| 1-564 | 100 | 4 |

TABLE 48-continued

| Compound No. | Application amount (active ingredient), g/10 a | Herbicidal effect to Ec |
|---|---|---|
| 1-565 | 100 | 4 |
| 1-566 | 100 | 4 |
| 1-567 | 100 | 4 |
| 1-568 | 100 | 5 |
| 1-569 | 100 | 5 |
| 1-570 | 100 | 5 |
| 1-571 | 100 | 5 |
| 1-572 | 100 | 4 |
| 1-573 | 100 | 5 |
| 1-574 | 100 | 4 |
| 1-576 | 100 | 5 |
| 1-581 | 100 | 4 |
| 1-583 | 100 | 4 |
| 1-584 | 100 | 5 |
| 1-585 | 100 | 5 |
| 1-586 | 100 | 5 |
| 1-589 | 100 | 4 |
| 1-590 | 100 | 4 |
| 1-591 | 100 | 4 |
| 1-593 | 100 | 4 |
| 1-595 | 100 | 4 |
| 1-599 | 100 | 4 |
| 1-602 | 100 | 4 |
| 1-603 | 100 | 4 |
| 1-604 | 100 | 5 |
| 1-606 | 100 | 4 |
| 1-607 | 100 | 5 |
| 1-608 | 100 | 5 |
| 1-609 | 100 | 5 |
| 1-616 | 100 | 5 |

<Test Example 4>

Test For Crop Selectivity By Paddy Field Soil Treatment

A paddy field soil was filled in a plastic pot of 100 cm$^2$ and subjected to puddling. Seeds of Echinochloa oryzicola Vasing. (Eo) were sowed; two-leaf stage seedlings of rice (Or) were transplanted in a depth of 2 cm; and water was filled in a depth of 3 cm. Next day, wettable powders produced in accordance with the Formulation 1 were diluted with water and dropped on the water surface. The application amount of each wettable powder was 100 g per 10 ares in terms of the active ingredient. Then, breeding was made in a greenhouse. At the 21st day from the treatment, the phytotoxicity and herbicidal effect of each wettable powder were examined in accordance with the standard shown in Table 40. The results are shown in Table 49.

TABLE 49

| Compound No. | Application amount of active ingredient g/10 a | Phytotoxicity to Or | Herbicidal effect to Eo |
|---|---|---|---|
| 1-145 | 100 | 0 | 5 |
| 1-190 | 100 | 1 | 5 |
| 1-198 | 100 | 1 | 5 |
| 1-203 | 100 | 1 | 5 |
| 1-228 | 100 | 1 | 5 |
| 1-229 | 100 | 1 | 5 |
| 1-230 | 100 | 0 | 5 |
| 1-328 | 100 | 0 | 5 |
| 1-331 | 100 | 0 | 5 |
| 1-365 | 100 | 1 | 5 |

TABLE 49-continued

| Compound No. | Application amount of active ingredient g/10 a | Phytotoxicity to Or | Herbicidal effect to Eo |
|---|---|---|---|
| 1-367 | 100 | 1 | 5 |
| 1-368 | 100 | 1 | 5 |
| 1-377 | 100 | 0 | 5 |
| 1-384 | 100 | 0 | 5 |
| 1-386 | 100 | 0 | 4 |
| 1-394 | 100 | 1 | 5 |
| 1-401 | 100 | 0 | 5 |
| 1-419 | 100 | 1 | 5 |
| 1-456 | 100 | 0 | 5 |
| 1-457 | 100 | 1 | 5 |
| 1-503 | 100 | 0 | 5 |
| 1-518 | 100 | 1 | 5 |
| 1-519 | 100 | 0 | 5 |
| 1-520 | 100 | 1 | 5 |
| 1-549 | 100 | 1 | 5 |
| 1-552 | 100 | 1 | 4 |
| 1-556 | 100 | 0 | 5 |
| 1-574 | 100 | 1 | 5 |
| 1-579 | 100 | 1 | 5 |
| 1-580 | 100 | 1 | 5 |
| 1-584 | 100 | 1 | 5 |
| 1-588 | 100 | 1 | 5 |
| 1-590 | 100 | 1 | 5 |
| 1-594 | 100 | 1 | 5 |
| 1-596 | 100 | 1 | 5 |
| 1-597 | 100 | 1 | 5 |
| 1-598 | 100 | 1 | 5 |
| 1-599 | 100 | 1 | 5 |
| 1-601 | 100 | 1 | 5 |
| 1-605 | 100 | 1 | 5 |
| 1-610 | 100 | 1 | 5 |
| 1-612 | 100 | 0 | 5 |
| 1-613 | 100 | 0 | 5 |
| 1-614 | 100 | 0 | 5 |
| 1-615 | 100 | 1 | 5 |
| 1-620 | 100 | 1 | 5 |
| 1-622 | 100 | 1 | 5 |
| 1-623 | 100 | 1 | 5 |
| 1-624 | 100 | 1 | 5 |
| 1-625 | 100 | 1 | 5 |
| 1-626 | 100 | 0 | 5 |
| 1-627 | 100 | 1 | 5 |
| 1-628 | 100 | 0 | 5 |
| 2-2 | 100 | 0 | 5 |
| 2-29 | 100 | 1 | 5 |

<Test Example 5>

Test For Herbicidal Effect During Breeding Period By Paddy Field Water Treatment A paddy field soil was filled in a plastic pot of 100 cm² and subjected to puddling. Seeds of *Monochoria vaginalis* Presl (Mo) and *Scirpus juncoides* Roxb. subsp. *juncoides* Roxb. (Sc) were sowed; water was filled in a depth of 3 cm; and breeding was made. When Mo reached a 1-leaf stage and Sc reached a 2-leaf stage, wettable powders produced in accordance with the Formulation 1 were diluted with water and dropped on the water surface. The application amount of each wettable powder was 100 g per 10 ares in terms of the active ingredient. Then, breeding was made in a greenhouse. At the 30th day from the treatment, the herbicidal effect of each wettable powder was examined in accordance with the standard shown in Table 40. The results are shown in Table 51. Incidentally, the details of comparative compounds 1 and 2 are shown in Table 50.

TABLE 50

| Compound | Structural formula | Patent No. and Compound No. |
|---|---|---|
| Comparative compound 1 | [structure: chloromethyl-methyl-isoxazoline sulfonyl ethylbenzyl] | JP-A-8-225548 and 2012 |
| Comparative compound 2 | [structure: chloromethyl-methyl-isoxazoline sulfonyl fluorobenzyl] | JP-A-8-225548 and 2059 |
| Comparative compound 3 | [structure: chloromethyl-methyl-isoxazoline sulfonyl chlorobenzyl] | JP-A-8-225548 and 2034 |

TABLE 51

| Compound No. | Application amount of active ingredient g/10 a | Herbicidal effect to Mo | Herbicidal effect to Sc |
|---|---|---|---|
| 1-8 | 25 | 5 | 4 |
| 1-39 | 25 | 5 | 5 |
| 1-49 | 25 | 5 | 5 |
| 1-58 | 25 | 4 | 5 |
| 1-157 | 25 | 5 | 5 |
| 1-382 | 25 | 5 | 4 |
| 1-547 | 25 | 5 | 5 |
| 1-567 | 25 | 5 | 5 |
| Comparative compound 1 | 25 | 1 | 1 |
| Comparative compound 2 | 25 | 1 | 1 |

<Test Example 6>

Test for herbicidal effect to broadleaf weeds by upland field soil treatment

An upland field soil was filled in a plastic pot of 80 cm². Seeds of *Polygonum lapathifolium* L. subsp. *nodosum* (Pers.) Kitam. (Po) and *Chenopodium album* L. (Ch) were sowed, followed by covering with the same soil. Wettable powders produced in accordance with the Formulation 1 were diluted with water and sprayed uniformly on the soil surface using a small sprayer, in an amount of 100 liters per 10 ares so that the amount of each active ingredient became 100 g per 10 ares. Then, breeding was made in a greenhouse. At the 30th day from the treatment, the herbicidal effect of each wettable powder was examined in accordance with the standard shown in Table 40. The results are shown in Table 52. Incidentally, the details of comparative compounds 1 and 3 are shown in Table 50.

TABLE 52

| Compound No. | Application amount of active ingredient g/10 a | Herbicidal effect to Po | Herbicidal effect to Ch |
|---|---|---|---|
| 1-2 | 25 | — | 4 |
| 1-39 | 25 | 4 | 5 |
| 1-46 | 25 | 5 | 4 |
| 1-498 | 25 | 5 | 5 |
| 1-499 | 25 | 5 | 4 |
| 1-500 | 25 | 5 | 4 |
| 1-501 | 25 | 5 | 5 |
| 1-523 | 25 | 5 | 5 |
| 1-526 | 25 | 5 | 5 |
| 1-532 | 25 | 5 | 5 |
| 1-534 | 25 | 5 | 5 |
| 1-555 | 25 | 5 | 4 |
| 1-573 | 25 | 5 | 5 |
| Comparative 1 | 25 | 0 | 0 |
| Comparative 3 | 25 | 1 | 0 |

Industrial Applicability

The compound represented by the general formula [I] according to the present invention shows an excellent herbicidal effect, at a low application amount over a wide period, from before germination to growth, to various weeds causing problems in upland fields, for example, Gramineae weeds [e.g. *Echinochloa crus-galli* (L.) *Beauv.* var. *crus-galli*, *Digitaria ciliaris* (Retz.) *Koeler*, *Setaria viridis* (L.) *Beauv.*, *Poa annua* L., *Sorghum halepense* (L.) *Pers.*, *Alopecurus aequalis* Sobol. var. *amurensis* (Komar.) *Ohwi*, and wild oats], broadleaf weeds [*Polygonum lapathifolium* L. *nodosum* (Pers.) *Kitam.*, *Amaranthus viridis* L., *Chenopodium album* L., *Stellaria media* (L.) *Villars*, *Abutilon avicennae*, *Sida spinosa*, *cassia obtusifolia*, *Ambrosia artemisiifolia* L. var. *elatior* (L.) Desc., and morning glory], and perennial or annual cyperaceous weeds [e.g. *Cyperus rotundus* L., *cyperus esculentus*, *Kyllinga brevifolia* Rottb. subsp. *leiolepis* (Fraxch. et Savat.) T. Koyama, *Cyperus microiria* Steud., and *Cyperus iria* L.].

Further, the present compound shows a herbicidal effect, at a low application amount over a wide period from before germination to growth, also to weeds emerging in paddy fields, i.e. annual weeds [e.g. *Echinochloa oryzicola* Vasing., *Cyperus difformis* L., *Monochoria vaginalis* (Burm. f.) Presl. var. *plantaginea* (Roxb.) Solms-Laub., and *Lindernia pyxidara* L.] and perennial weeds [e.g. *Cyperus serotinus* Rottb., *Eleocharis kuroguwai* Ohwi, and *Scirpus juncoides* Roxb. subsp. *hotarui* (Ohwi) T. Koyama].

The herbicide of the present invention has high safety to crops, particularly to rice, wheat, barley, corn, grain sorghum, soybean, cotton, sugar beat, lawn, fruit trees, etc.

What is claimed is:

1. An isoxazoline derivative represented by the following general formula [I] or a salt thereof:

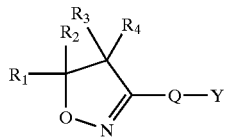

[I]

wherein Q is a group represented by $-S(O)_n-(CR_5R_6)_m-$ (wherein n is 0 or an integer of 1 to 2, m is an integer of 1 to 3, and $R_5$ and $R_6$ are each independently a hydrogen atom, a cyano group, an alkoxycarbonyl group or a $C_1$ to $C^6$ alkyl group);

$R_1$ and $R_2$ are each independently a hydrogen atom, a $C_1$ to $C_8$ alkyl group [which may be substituted with $C_3$ to $C_8$ cycloalkyl group, $C_1$ to $C_6$ alkoxy group, $C_1$ to $C_6$ alkylcarbonyl group, $C_1$ to $C_6$ alkylthio group, $C_1$ to $C_6$ alkylsulfinyl group, $C_1$ to $C_6$ alkylsulfonyl group, $C_1$ to $C_6$ alkylamino group, di($C_1$ to $C_6$ alkyl)amino group, cyano group, $C_1$ to $C_6$ alkoxycarbonyl group, $C_1$ to $C_6$ alkylaminocarbonyl group, di($C_1$ to $C_6$ alkyl) aminocarbonyl group, ($C_1$ to $C_6$ alkylthio)carbonyl group, carboxyl group, optionally substituted benzyloxy group, optionally substituted phenoxy group, or optionally substituted phenyl group], a $C_3$ to $C_8$ cycloalkyl group, a $C_1$ to $C_6$ alkoxycarbonyl group, a $C_3$ to $C_8$ alkylaminocarbonyl group, a di ($C_1$ to $C_6$ alkyl) aminocarbonyl group, a $C_1$ to $C_6$ alkylthiocarbonyl group, a carboxyl group or an optionally substituted phenyl group;

$R_3$ and $R_4$ are each independently a hydrogen atom, a $C_1$ to $C_8$ alkyl group (which may be substituted with 1 to 3 same or different, $C_3$ to $C_8$ cycloalkyl groups or $C_1$ to $C_6$ alkoxy groups) or a $C_3$ to $C_8$ cycloalkyl group; and Y is a phenyl group substituted with 1 to 5 same or different $R_7$; each $R_7$ is a hydrogen atom, a $C_1$ to $C_6$ alkyl group [which may be substituted with 1 to 3 same or different halogen atoms, $C_1$ to $C_6$ alkoxy groups, hydroxyl groups, $C_1$ to $C_6$ alkylthio groups, $C_1$ to $C_6$ alkylsulfinyl groups, $C_1$ to $C_6$ alkylsulfonyl groups, $C_1$ to $C_6$ alkylamino groups, di($C_1$ to $C_6$)alkylamino groups, cyano groups or optionally substituted phenoxy groups], a $C_1$ to $C_6$ alkoxy group (which may be substituted with 1 to 3 same or different halogen atoms, $C_1$ to $C_6$ alkoxy groups, $C_2$ to $C_6$ alkenyl groups, $C_1$ to $C_6$ alkynyl groups, $C_1$ to $C_6$ alkoxycarbonyl groups, $C_1$ to $C_6$ alkylcarbonyl groups or $C_3$ to $C_8$ cycloalkyl groups), a $C_2$ to $C_6$ alkenyl group, a $C_3$ to $C_8$ cycloalkyloxy group, a $C_1$ to $C_6$ alkylthio group (which may be substituted with 1 to 3 same or different halogen atoms or $C_1$ to $C_6$ alkoxy groups), a $C_1$ to $C_6$ alkylsulfinyl group (which may be substituted with 1 to 3 same or different halogen atoms or $C_1$ to $C_6$ alkoxy groups), a $C_1$ to $C_6$ alkylsulfonyl group (which may be substituted with 1 to 3 same or different halogen atoms or $C_1$ to $C_6$ alkoxy groups), an optionally substituted benzyloxy group, an amino group [which may be substituted with $C_1$ to $C_6$ alkyl group, $C_1$ to $C_6$ alkylsulfonyl group, $C_1$ to $C_6$ alkylcarbonyl($C_1$ to $C_6$ alkyl) group or $C_1$ to $C_6$ alkylsulfonyl ($C_1$ to $C_6$ alkyl) group], a di($C_1$ to $C_6$ alkyl)amino group, a halogen atom, a cyano group, a nitro group, a $C_1$ to $C_6$ alkoxycarbonyl group, a $C_3$ to $C_8$ cycloalkyloxycarbonyl group, a carboxyl group, a $C_2$ to $C_6$ alkenyloxycarbonyl group, a $C_2$ to $C_6$ alkynyloxycarbonyl group, an optionally substituted benzyloxycarbonyl group, an optionally substituted phenoxycarboriyl group or a $C_1$ to $C_6$ alkylcarbonyloxy group; provided that compounds wherein $R_{11}$ $R_2$, $R_3$ and $R_4$ are hydrogen at the same time are excluded.

2. An isoxazoline derivative or a salt thereof according to claim 1, wherein in the general formula [I], Q is a group represented by $-S(O)_n-(CR_5R_6)_m-$ (wherein n is 0 or an integer of 1 to 2, m is 1, and $R_5$ and $R_6$ are a hydrogen atom);

$R_1$ and $R_2$ are each independently a hydrogen atom, a $C_1$ to $C_8$ alkyl group (which may be substituted with $C_3$ to $C_8$ cycloalkyl group or $C_1$ to $C_6$ alkoxy group) or a $C_3$ to $C_8$ cycloalkyl group;

$R_3$ and $R_4$ are each independently a hydrogen atom or a $C_1$ to $C_8$ alkyl group (which may be substituted with 1 to 3 same or different, $C_3$ to $C_8$ cycloalkyl groups or $C_1$ to $C_6$ alkoxy groups); and Y is a phenyl group substituted with 1 to 5 same or different $R_7$; each $R_7$ is a hydrogen atom, a $C_1$ to $C_6$ alkyl group [which may be substituted with 1 to 3 same or different halogen atoms, $C_1$ to $C_6$ alkoxy groups, hydroxyl groups, $C_1$ to $C_6$ alkylthio groups, $C_1$ to $C_6$ alkylsulfinyl groups, $C_1$ to $C_6$ alkylsulfonyl groups, $C_1$ to $C_6$ alkylamino groups, $C_1$ to $C_6$ dialkylamino groups, cyano groups or optionally substituted phenoxy groups], a $C_1$ to $C_6$ alkoxy group (which may be substituted with 1 to 3 same or different halogen atoms, $C_1$ to $C_6$ alkoxy groups, $C_2$ to $C_6$ alkenyl groups, $C_2$ to $C_6$ alkynyl groups, $C_1$ to $C_6$ alkoxycarbonyl groups, $C_1$ to $C_6$ alkylcarbonyl groups or $C_3$ to $C_8$ cycloalkyl groups), a $C_3$ to $C_8$ cycloalkyloxy group or a halogen atom; provided that compounds wherein $R_1$, $R_2$, $R_3$ and $R_4$ are hydrogen at the same time are excluded.

3. An isoxazoline derivative or a salt thereof according to claim 1, wherein in the general formula [I], Q is a group represented by $-S(O)_n-(CR_5R_6)_m-$ (wherein n is 0 or an integer of 1 to 2, m is 1, and $R_5$ and $R_6$ are a hydrogen atom);

$R_1$ and $R_2$ are a $C_1$ to $C_8$ alkyl group;

$R_3$ and $R_4$ are a hydrogen atom;

Y is a phenyl group substituted with 1 to 5 same or different $R_7$; each $R_7$ is a hydrogen atom, a $C_1$ to $C_6$ alkyl group (which may be substituted with 1 to 3 same or different halogen atoms or $C_1$ to $C_6$ alkoxy groups), a $C_1$ to $C_6$ alkoxy group (which may be substituted with 1 to 3 same or different halogen atoms or $C_1$ to $C_6$ alkoxy groups), or a halogen atom.

4. A herbicidal formulation containing, as the active ingredient, an isoxazoline derivative or its salt set forth in claim 1.

5. A herbicidal formulation containing, as the active ingredient, an isoxazoline derivative or its salt set forth in claim 2.

6. A herbicidal formulation containing, as the active ingredient, an isoxazoline derivative or its salt set forth in claim 3.

7. An isoxazoline compound or a salt according to claim 1, wherein m is 1; and $R_1$ and $R_2$ are each independently a hydrogen atom, a $C_1$ to $C_8$ alkyl group [which may be substituted with $C_1$ to $C_H$ cycloalkyl group, $C_1$ to $C_6$ alkoxy group, $C_1$ to $C_6$ alkylcarbonyl group, $C_1$ to $C_6$ alkylthio group, $C_1$ to $C_6$ alkylsulfinyl group, $C_1$ to $C_6$ alkylsulfonyl group, $C_1$ to $C_6$ alkylamino group, di($C_1$ to $C_6$ alkyl)amino group, cyano group, $C_1$ to $C_6$ alkoxycarbonyl group, $C_1$ to $C_6$ alkylaminocarbonyl group, di($C_1$ to $C_6$ alkyl)aminocarbonyl group, ($C_1$ to $C_6$ alkylthio)carbonyl group, carboxyl group, optionally substituted benzyloxy group, optionally substituted phenoxy group, or optionally substituted phenyl group], a $C_3$ to $C_8$ cycloalkyl group, a $C_1$ to $C_6$ alkoxycarbonyl group, a $C_1$ to $C_6$ alkylaminocarbonyl group, a di($C_1$ to $C_6$ alkyl)aminocarbonyl group, a ($C_1$ to $C_6$ alkylthio)carbonyl group, a carboxyl group or an, optionally substituted pheryl group.

8. An isoxazoline compound or a salt according to claim 1, wherein m is 1;

$R_5$ and $R_6$ are each independently a hydrogen atom or a $C_1$ to $C_6$ alkyl group;

$R_1$ and $R_2$ are cash independently a hydrogen atom, a $C_1$ to $C_H$ alkyl group [which may be substituted with $C_3$ to $C_8$ cycloalkyl group or $C_1$ to $C_6$ alkoxy group], or a $C_3$ to $C_8$ cycloalkyl group; and $R_3$ and $R_4$ are each independently a hydrogen atom or a $C_1$ to $C_8$ alkyl group [which may be substituted with 1 to 3 same or different, $C_3$ to $C_8$ cycloalkyl group or $C_1$ to $C_6$ alkoxy group].

9. An isoxazoline compound or a salt according to claim 1, wherein m is 1;

$R_3$ and $R_6$ are each independently a hydrogen atom or a $C_1$ to $C_6$ alkyl group;

$R_1$ and $R_2$ are each independently a hydrogen atom, a $C_1$ to $C_8$ alkyl group which may be substituted with $C_3$ to $C_8$ cycloalkyl group, or a $C_3$ to $C_8$ oycloalkyl group; and $R_3$ and $R_4$ are each independently a hydrogen atom or a $C_1$ to $C_8$ alkyl group.

10. An isoxazoline compound or a salt according to claim 1, wherein m is 1;

$R_5$ and $R_6$ are each independently a hydrogen atom or a $C_1$ to $C_6$ alkyl group;

$R_1$ and $R_2$ are each independently a hydrogen atom, a $C_1$ to $C_8$ alkyl group which may be substituted with $C_3$ to $C_8$ cycloalkyl group, or a $C_3$ to $C_8$ cycloalkyl group;

$R_3$ and $R_4$ are each independently a hydrogen atom or a $C_1$ to $C_8$ alkyl group; and Y is a hydrogen atom, a $C_1$ to $C_{10}$ alkyl group which may be substituted with 1 to 3 same or different halogen atoms, or a phenyl group substituted with 1 to 5 same or different $R_7$; $R_7$ is a hydrogen atom, a $C_1$ to $C_6$ alkyl group which may be substituted with 1 to 3 same or different halogen atoms, a $C_1$ to $C_6$ alkoxy group [which may be substituted with 1 to 3 same or different halogen atoms, $C_2$ to $C_6$ alkenyl group, $C_2$ to $C_6$ alkynyl group, or $C_3$ to $C_6$ cycloalkyl group], a $C_3$ to $C_8$ cycloalkyloxy group, a $C_1$ to $C_6$ alkylthio group [which may be substituted with 1 to 3 same or different halogen atoms or $C_1$ to $C_6$ alkoxy group], a halogen atom, a cyano group, a nitro group, a $C_1$ to $C_6$ alkoxycarbonyl group, or a $C_3$ to $C_8$ cycloalkyloxycarbonyl group.

11. An isoxazoline compound or a salt according to claim 1, wherein

Q is a group represented by $-S(O)_n-(CR_5R_6)_m-$ (wherein n is 2, m is 1 and $R_5$ and $R_6$ are a hydrogen atom);

$R_1$ and $R_2$ are each independently a $C_1$ to $C_3$ alkyl group;

$R_3$ and $R_4$ are a hydrogen atom; and

Y is a phenyl group substituted with 1 to 5 same or different $R_7$; $R_7$ is a hydrogen atom, a $C_1$ to $C_6$ alkyl group which may be substituted with 1 to 3 same or different halogen atoms or a $C_1$ to $C_6$ alkoxy group, a $C_1$ to $C_6$ alkoxy group which may be substituted with 1 to 3 same or different halogen atoms or a $C_1$ to $C_6$ alkoxy group, or a halogen atom.

12. An isoxazoline compound or a salt according to claim 1, wherein

Q is a group represented by $-S(O)_n-(CR_5R_6)_m-$ (wherein n is 2, m is 1 and $R_5$ and $R_6$ are a hydrogen atom);

$R_1$ and $R_2$ are a methyl group;

$R_3$ and $R_4$ are a hydrogen atom; and

Y is a phenyl group substituted with 1 to 5 same or different $R_7$; $R_7$ is a hydrogen atom, a $C_1$ to $C_6$ alkyl group which may be substituted with 1 to 3 same or different halogen atoms, a $C_1$ to $C_6$ alkoxy group which may be substituted with 1 to 3 same or different halogen atoms, or a halogen atom.

13. An isoxazoline compound or a salt according to claim 1, wherein

Q is a group represented by —S(O)$_n$—(CR$_5$R$_6$)$_m$— (wherein n is 2, m is 1 and R5 and R6 are a hydrogen atom);

R$_1$ and R$_2$ are a methyl group;

R$_3$ and R$_4$ are a hydrogen atom; and

Y is a phenyl group substituted with 1 to 5 same or different R$_7$; R$_7$ is a hydrogen atom, a $C_1$ to $C_3$ alkyl group which may be substituted with 1 to 3 same or different halogen atoms, a $C_1$ to $C_3$ alkoxy group which may be substituted with 1 to 3 same or different halogen atoms, or a halogen atom.

14. An isoxazoline compound or a salt according to claim 1, wherein n is 2, m is 1 and R$_5$ and R$_6$ are a hydrogen atom;

R$_1$ and R$_2$ are each independently a $C_1$ to $C_3$ alkyl group; and

Y is a phenyl group substituted with 1 to 5 same or different R$_7$; R$_7$ is a hydrogen atom, a halogen atom, a $C_1$ to $C_3$ alkyl group, a $C_1$ to $C_3$ alkoxy group, a $C_1$ to $C_3$ haloalkyl group or a $C_1$ to $C_3$ haloalkoxy group.

15. An isoxazoline compound or a salt according to claim 14, wherein

R$_1$ and R$_2$ are a methyl group; and

R$_7$ is a is a hydrogen atom, F, Cl, Br, a $C_1$ to $C_3$ alkyl group, a $C_1$ to $C_3$ alkoxy group, a $C_1$ to $C_3$ fluoroalkyl group, a $C_1$ to $C_3$ chloroalkyl group, a $C_1$ to $C_3$ fluoroalkoxy group or a $C_1$ to $C_3$ chloroalkoxy group.

16. A herbicidal formulation containing, as the active ingredient, an isoxazoline derivative or its salt set forth in claim 7.

17. A herbicidal formulation containing, as the active ingredient, an isoxazoline derivative or its salt set forth in claim 8.

18. A herbicidal formulation containing, as the active ingredient, an isoxazoline derivative or its salt set forth in claim 9.

19. A herbicidal formulation containing, as the active ingredient, an isoxazoline derivative or its salt set forth in claim 10.

20. A herbicidal formulation containing, as the active ingredient, an isoxazoline derivative or its salt set forth in claim 11.

21. A herbicidal formulation containing, as the active ingredient, an isoxazoline derivative or its salt set forth in claim 12.

22. A herbicidal formulation containing, as the active ingredient, an isoxazoline derivative or its salt set forth in claim 13.

23. A herbicidal formulation containing, as the active ingredient, an isoxazoline derivative or its salt set forth in claim 14.

24. A herbicidal formulation containing, as the active ingredient, an isoxazoline derivative or its salt set forth in claim 15.

25. An isoxazoline compound or salt according to claim 1, wherein

Q is a group represented by —S(O)$_n$—(CR$_5$R$_6$)$_m$- (wherein n is 2, m is 1 and R$_5$ and R$_6$ are a hydrogen atom);

R$_1$ and R$_2$ are methyl group;

R$_3$ and R$_4$ are a hydrogen atom; and

Y is a phenyl group substituted with 1 to 5 same or different R$_7$; R$_7$ is a hydrogen atom, a chlorine atom or a $C_1$ to $C_3$ alkoxy group.

26. An isoxazoline compound or salt according to claim 1, wherein

Q is a group represented by —S(O)$_n$—(CR$_5$R$_6$)$_m$- (wherein n is 2, m is 1 and R$_5$ and R$_6$ are a hydrogen atom);

R$_1$ and R$_2$ are methyl group;

R$_1$ and R$_4$ are a hydrogen atom; and

Y is a phenyl group substituted with 1 to 5 same or different R$_7$; R$_7$ is a hydrogen atom, a chlorine atom or a $C_1$ to $C_3$ fluoroalkoxy group.

27. An isoxazoline compound or salt according to claim 1, wherein

Q is a group represented by —S(O)$_n$—(CR$_5$R$_6$)$_m$- (wherein n is 2, m is 1 and R$_5$ and R$_6$ are a hydrogen atom);

R$_1$ and R$_2$ are methyl group;

R$_3$ and R$_4$ are a hydrogen atom; and

Y is a phenyl group substituted with 1 to 5 same or different R$_7$; R$_7$ is a hydrogen atom, a chlorine atom or a 2-propynyloxy group.

* * * * *

UNITED STATES PATENT AND TRADEMARK OFFICE
CERTIFICATE OF CORRECTION

PATENT NO. : 6,841,519 B1
APPLICATION NO. : 10/049039
DATED : January 11, 2005
INVENTOR(S) : Masao Nakatani et al.

It is certified that error appears in the above-identified patent and that said Letters Patent is hereby corrected as shown below:

Title page, item (57) Abstract, "——$S(O)_n$——$(CR_5R_6)_m$-" should be -- -$S(O)_n$-$(CR_5R_6)_m$- --.
Column 1, line 45, "——$S(O),$——$(CR_5R_6)_m$-" should be -- -$S(O)_n$-$(CR_5R_6)_m$- --.
Column 1, line 50, "R1" should be --$R_1$--.
Column 4, line 20, "——$S(O)_n$-$(CR_5R_6)_m$-" should be --$S(O)_n$-$(CR_5R_6)_m$- --.
Column 11, Table 9, row Compound No. 1-206, column $R_2$, "EL" should be --Et--.
Column 21, Table 20, row Compound No. 1-494, column Y, "Ph(2-Cl, 6-P)" should be --Ph(2-Cl, 6-F)--.
Column 21, Table 21, row Compound No. 1-510, column Melting point (°C) or refractive index ($n_D^{20}$), "121-126" should be --124-126--.
Column 23, Table 22, row Compound No. 1-527, column Melting point (°C) or refractive index ($n_D^{20}$), "69-90" should be --89-90--.
Column 23, Table 22, row Compound No. 1-531, column Y, "Ph(2,3,4,5,6-$F_2$)" should be --Ph(2,3,4,5,6-$F_5$)--.
Column 24, Table 23, row Compound No. 1-553, column Y, "Ph(2-Pr, 6-F)" should be --Ph(2-Br, 6-F)--.
Column 29, Table 28, row Compound No. 1-677, column Y, "Ph(2,3,6-$(Me)_2$, 5-Cl)" should be --Ph(2,3,6-$(Me)_3$, 5-Cl)--.
Column 29, Table 29, row Compound No. 1-703, column Y, "Ph(213,5-$(Me)_3$, 6-OMe)" should be --Ph(2,3,5-$(Me)_3$, 6-OMe)--.
Column 29, Table 29, row Compound No. 1-706, column Y, "Ph(213,6-$(Me)_3$, 5-Br)" should be --Ph(2,3,6-$(Me)_3$, 5-Br)--.
Column 29, Table 29, row Compound No. 1-711, column Y, "Ph(2,5$(Me)_3$, 3,6-$Cl_2$)" should be --Ph(2,5$(Me)_2$, 3,6-$Cl_2$)--.
Column 35, Table 37, row Compound No. 1-920, column Y, should be --$CH_2OCH_2C{\equiv}CH$--. Line number 40 obscures this text.

UNITED STATES PATENT AND TRADEMARK OFFICE
CERTIFICATE OF CORRECTION

PATENT NO.       : 6,841,519 B1                                           Page 2 of 4
APPLICATION NO.  : 10/049039
DATED            : January 11, 2005
INVENTOR(S)      : Masao Nakatani et al.

It is certified that error appears in the above-identified patent and that said Letters Patent is hereby corrected as shown below:

Column 35, Table 38 should be:

TABLE 38

| Compound No. | $R_1$ | $R_2$ | $R_3$ | $R_4$ | Q | Y | Melting point (°C) or refractive index ($n_D^{20}$) |
|---|---|---|---|---|---|---|---|
| 1-921 | Me | Me | H | H | $SO_2CH_2$ | $Ph(2-OC_2H_4CO_2Me)$ | |
| 1-922 | Me | Me | H | H | $SO_2CH_2$ | $Ph(2-OC_2H_4COMe)$ | |
| 1-923 | Me | Me | H | H | $SO_2CH_2$ | $Ph(2-CO_2Ph)$ | |
| 1-924 | Me | Me | H | H | $SCH_2$ | $Ph(2,3,5-(Me)_3, 6-F)$ | |
| 1-925 | Me | Me | H | H | $SCH_2$ | $Ph(2,3,5-(Me)_3, 6-Cl)$ | |
| 1-926 | Me | Me | H | H | $SCH_2$ | $Ph(2,3,5-(Me)_3, 6-Br)$ | |
| 1-927 | Me | Et | H | H | $SCH_2$ | $Ph(2,3,5-(Me)_3, 6-F)$ | |
| 1-928 | Me | Et | H | H | $SCH_2$ | $Ph(2,3,5-(Me)_3, 6-Cl)$ | |
| 1-929 | Me | Et | H | H | $SCH_2$ | $Ph(2,3,5-(Me)_3, 6-Br)$ | |
| 1-930 | Me | Me | H | H | $SOCH_2$ | $Ph(2,3,5-(Me)_3, 6-F)$ | |
| 1-931 | Me | Me | H | H | $SOCH_2$ | $Ph(2,3,5-(Me)_3, 6-Cl)$ | |
| 1-932 | Me | Me | H | H | $SOCH_2$ | $Ph(2,3,5-(Me)_3, 6-Br)$ | |
| 1-933 | Me | Et | H | H | $SOCH_2$ | $Ph(2,3,5-(Me)_3, 6-F)$ | |
| 1-934 | Me | Et | H | H | $SOCH_2$ | $Ph(2,3,5-(Me)_3, 6-Cl)$ | |
| 1-935 | Me | Et | H | H | $SOCH_2$ | $Ph(2,3,5-(Me)_3, 6-Br)$ | |
| 1-936 | Me | Me | H | H | $SO_2CH_2$ | $Ph(2,3,5-(Me)_3, 6-F)$ | |
| 1-937 | Me | Me | H | H | $SO_2CH_2$ | $Ph(2,3,5-(Me)_3, 6-Cl)$ | |
| 1-938 | Me | Me | H | H | $SO_2CH_2$ | $Ph(2,3,5-(Me)_3, 6-Br)$ | |
| 1-939 | Me | Et | H | H | $SO_2CH_2$ | $Ph(2,3,5-(Me)_3, 6-F)$ | |
| 1-940 | Me | Et | H | H | $SO_2CH_2$ | $Ph(2,3,5-(Me)_3, 6-Cl)$ | |
| 1-941 | Me | Et | H | H | $SO_2CH_2$ | $Ph(2,3,5-(Me)_3, 6-Br)$ | |

Column 39, line 65, "genera," should be --general--.
Column 41, lines 1 to 23 (<Production Process 2> Step 6), "$X_1$——$(CR5R_6)_m$—Y" should be --$X_1$——$(CR_5R_6)_m$—Y--.
[XIV]                    [XIV]
Column 41, line 25, "$R_0$" should be --$R_8$--.
Column 41, lines 63 to 64, "——$(CR_5R_6)_n$——Y" should be -- -$(CR_5R_6)_m$-Y--.
Column 42, lines 50 to 51, "5-ethyl-3-(2,6-difluorobenzylsulfinyl)-5-methyl-2-isoxazloline" should be --5-ethyl-3-(2,6-difluorobenzylsulfinyl)-5-methyl-2-isoxazoline--.
Column 42, line 54, "Δυ" should be --Δv--.
Column 42, line 54, "(1H, s) 1.75" should be --(1H, s), 1.75--.
Column 42, line 55, "(3H, 3)" should be --(3H, s)--.

UNITED STATES PATENT AND TRADEMARK OFFICE
CERTIFICATE OF CORRECTION

PATENT NO. : 6,841,519 B1
APPLICATION NO. : 10/049039
DATED : January 11, 2005
INVENTOR(S) : Masao Nakatani et al.

It is certified that error appears in the above-identified patent and that said Letters Patent is hereby corrected as shown below:

Column 43, lines 10 to 11, "5-ethyl-3-(2,6-difluorobenzylsulfonyl)-5-methyl-2-isoxazloline" should be --5-ethyl-3-(2,6-difluorobenzylsulfinyl)-5-methyl-2-isoxazoline--.
Column 43, line 15, "$\Delta\upsilon$-51.1 Hz" should be --$\Delta v$=51.1 Hz--.
Column 43, lines 36 to 37, "3-(2,6-difluorobenzylsulfonyl)-5,5-dimethyl-2-isoxazbline" should be --3-(2,6-difluorobenzylsulfonyl)-5,5-dimethyl-2-isoxazoline--.
Column 43, line 67, "(6H, s)<" should be --(6H, s)--.
Column 44, line 6, "193.0 g" should be --143.0 g--.
Column 44, line 18, "(141.2 mmoles)" should be --(741.2 mmoles)--.
Column 45, line 16, "$\Delta\upsilon$" should be --$\Delta v$--.
Column 45, line 34, "(2H,min)" should be --(2H,m)--.
Column 45, line 35, "J=117.4" should be --J=17.4--.
Column 45, line 36, "$\Delta\upsilon$" should be --$\Delta v$--.
Column 50, line 65, "uniformly: on" should be --uniformly on--.
Column 56, lines 40 to 41, "Echinochloa oryzicola Vasing. (Eo)" should be --*Echinochloa oryzicola Vasing.* (Eo)--.
Column 59, lines 65 to 66, "——$S(O)_n$——$(CR_5R_6)_m$-" should be -- -$S(O)_n$-$(CR_5R_6)_m$- --.
Column 60, line 2, "$C^6$" should be --$C_6$--.
Column 60, line 15, "$C_3$ to $C_8$" should be --$C_1$ to $C_6$--.
Column 60, lines 34 to 35, "$C_1$ to $C_6$ alkynyl groups" should be --$C_2$ to $C_6$ alkynyl groups--.
Column 60, lines 55 to 56, "phenoxycarboriyl" should be --phenoxycarbonyl--.
Column 60, line 57, "$R_{11}$" should be --$R_1$,--.
Column 60, line 61, "——$S(O)_n$——$(CR_5R_6)_m$-" should be -- -$S(O)_n$-$(CR_5R_6)_m$- --.
Column 61, line 23, "——$S(O)_n$——$(CR_5R_6)_m$-" should be -- -$S(O)_n$-$(CR_5R_6)_m$- --.
Column 61, line 27, "$R_1$" should be --$R_4$--.
Column 61, lines 48 to 49, "$C_1$ to $C_H$ cycloalkyl" should be --$C_3$ to $C_8$ cycloalkyl--.
Column 61, line 62, "or an, optionally" should be --or an optionally--.
Column 61, line 63, "pheryl" should be --phenyl--.
Column 62, line 1, "cash" should be --each--.
Column 62, line 2, "$C_H$" should be --$C_8$--.
Column 62, line 11, "$R_3$" should be --$R_5$--.
Column 62, line 15, "oycloalkyl" should be --cycloalkyl--.

UNITED STATES PATENT AND TRADEMARK OFFICE
CERTIFICATE OF CORRECTION

PATENT NO. : 6,841,519 B1
APPLICATION NO. : 10/049039
DATED : January 11, 2005
INVENTOR(S) : Masao Nakatani et al.

It is certified that error appears in the above-identified patent and that said Letters Patent is hereby corrected as shown below:

Column 62, line 38, "$C_3$ to $C_6$ cycloalkyl" should be --$C_3$ to $C_8$ cycloalkyl--.
Column 62, line 45, "——$S(O)_n$——$(CR_5R_6)_m$-" should be -- -$S(O)_n$-$(CR_5R_6)_m$- --.
Column 62, line 51, "different" should be --different $R_7$;--.
Column 62, line 52, "$R_7$; $R_7$" should be --$R_7$--.
Column 62, line 61, "——$S(O)_n$——$(CR_5R_6)_m$-" should be -- -$S(O)_n$-$(CR_5R_6)_m$- --.
Column 63, line 7, "——$S(O)_n$——$(CR_5R_6)_m$—" should be -- -$S(O)_n$-$(CR_5R_6)_m$- --.
Column 63, line 8, "R5 and R6" should be --$R_5$ and $R_6$--.
Column 63, line 32, "is a is a" should be --is a--.
Column 64, line 17, "——$S(O)_n$——$(CR_5R_6)_m$-" should be -- -$S(O)_n$-$(CR_5R_6)_m$- --.
Column 64, line 27, "——$S(O)_n$——$(CR_5R_6)_m$-" should be -- -$S(O)_n$-$(CR_5R_6)_m$- --.
Column 64, line 31, "$R_1$ and $R_4$" should be --$R_3$ and $R_4$--.
Column 64, line 37, "——$S(O)_n$——$(CR_5R_6)_m$-" should be -- -$S(O)_n$-$(CR_5R_6)_m$- --.

Signed and Sealed this

Twenty-first Day of October, 2008

JON W. DUDAS
*Director of the United States Patent and Trademark Office*